United States Patent
Wang et al.

(10) Patent No.: US 10,551,371 B2
(45) Date of Patent: Feb. 4, 2020

(54) SYSTEM AND METHOD FOR MONITORING CARDIOMYOCYTE BEATING, VIABILITY AND MORPHOLOGY AND FOR SCREENING FOR PHARMACOLOGICAL AGENTS WHICH MAY INDUCE CARDIOTOXICITY OR MODULATE CARDIOMYOCYTE FUNCTION

(75) Inventors: Xiaobo Wang, San Diego, CA (US); Wei Ouyang, San Diego, CA (US); Nan Li, San Diego, CA (US); Biao Xi, San Diego, CA (US); Yama A. Abassi, San Diego, CA (US); Xiao Xu, San Diego, CA (US)

(73) Assignee: ACEA Biosciences, Inc., San Diego, CA (US)

( * ) Notice: Subject to any disclaimer, the term of this patent is extended or adjusted under 35 U.S.C. 154(b) by 564 days.

(21) Appl. No.: 12/774,709

(22) Filed: May 5, 2010

(65) Prior Publication Data
US 2011/0039294 A1  Feb. 17, 2011

Related U.S. Application Data

(63) Continuation-in-part of application No. 12/435,569, filed on May 5, 2009, now Pat. No. 9,709,548, and a
(Continued)

(51) Int. Cl.
*G01N 33/487* (2006.01)

(52) U.S. Cl.
CPC .............................. *G01N 33/48735* (2013.01)

(58) Field of Classification Search
CPC .. G01N 33/48; G01N 33/483; G01N 33/4833; G01N 33/4836; G01N 33/487;
(Continued)

(56) References Cited

U.S. PATENT DOCUMENTS 2,656,508 A   10/1953   Coulter
3,259,842 A    7/1966   Coulter et al.
(Continued)

FOREIGN PATENT DOCUMENTS

EP   1138758   10/2001
EP   1195432    4/2002
(Continued)

OTHER PUBLICATIONS

Berdondini et al., High-density electrode array for imaging in vitro electrophysiological activity, Biosensors and Bioelectronics 21 (2005) p. 167-174.*
(Continued)

*Primary Examiner* — Robert J Eom
(74) *Attorney, Agent, or Firm* — Wagenknecht IP Law Group PC

(57) ABSTRACT

Devices and methods for performing extracellular recording of cells, such as excitable cells, cardiomyocytes, and cardiomyocyte precursor cells is provided. An exemplary device includes a nonconductive substrate forming or provided as a base of one or more wells; a recording electrode positioned on the substrate within the well, wherein the recording electrode is accessible to cells when a cell sample is added to the device; and a reference electrode positioned within the well in a cell-free zone, the cell-free zone characterized as free from contact with cells when the cell sample is added to the device, thereby preventing contact between cells and the reference electrode.

21 Claims, 65 Drawing Sheets

Related U.S. Application Data continuation-in-part of application No. 11/235,938, filed on Sep. 27, 2005, now Pat. No. 7,732,127, which is a continuation-in-part of application No. 11/197,994, filed on Aug. 4, 2005, now Pat. No. 7,468,255, which is a continuation-in-part of application No. 11/055,639, filed on Feb. 9, 2005, now Pat. No. 7,560,269, which is a continuation-in-part of application No. 10/987,732, filed on Nov. 12, 2004, now Pat. No. 7,192,752, said application No. 11/235,938 is a continuation-in-part of application No. 11/198,831, filed on Aug. 4, 2005, now Pat. No. 8,263,375, said application No. 10/987,732 is a continuation-in-part of application No. 10/705,615, filed on Nov. 10, 2003, now Pat. No. 7,459,303.

(60) Provisional application No. 61/191,684, filed on Sep. 11, 2008, provisional application No. 61/126,533, filed on May 5, 2008, provisional application No. 61/323,782, filed on Apr. 13, 2010, provisional application No. 61/310,557, filed on Mar. 4, 2010, provisional application No. 61/175,566, filed on May 5, 2009, provisional application No. 60/519,567, filed on Nov. 12, 2003, provisional application No. 60/630,131, filed on Nov. 22, 2004, provisional application No. 60/630,071, filed on Nov. 22, 2004, provisional application No. 60/613,872, filed on Sep. 27, 2004, provisional application No. 60/613,749, filed on Sep. 27, 2004, provisional application No. 60/630,809, filed on Nov. 24, 2004, provisional application No. 60/633,019, filed on Dec. 3, 2004, provisional application No. 60/647,159, filed on Jan. 26, 2005, provisional application No. 60/653,904, filed on Feb. 17, 2005, provisional application No. 60/673,678, filed on Apr. 21, 2005, provisional application No. 60/689,422, filed on Jun. 10, 2005.

(58) Field of Classification Search
CPC ....... G01N 33/48707; G01N 33/48721; G01N 33/48735
USPC .......................................................... 422/83
See application file for complete search history.

(56) References Cited

U.S. PATENT DOCUMENTS

| | | |
|---|---|---|
| 3,743,581 A | 7/1973 | Cady et al. |
| 3,890,201 A | 6/1975 | Cady |
| 4,072,578 A | 2/1978 | Cady et al. |
| 4,225,410 A | 9/1980 | Pace |
| 4,686,190 A | 8/1987 | Cramer et al. |
| 4,920,047 A | 4/1990 | Giaever et al. |
| 5,001,048 A | 3/1991 | Taylor et al. |
| 5,134,070 A | 7/1992 | Casnig |
| 5,187,096 A | 2/1993 | Giaever et al. |
| 5,218,312 A | 6/1993 | Moro |
| 5,247,827 A | 9/1993 | Shah |
| 5,278,048 A | 1/1994 | Parce et al. |
| 5,284,753 A | 2/1994 | Goodwin |
| 5,514,555 A | 5/1996 | Springer et al. |
| 5,563,067 A | 10/1996 | Sugihara et al. |
| 5,601,997 A | 2/1997 | Tchao et al. |
| 5,622,872 A | 4/1997 | Ribi |
| 5,626,734 A | 5/1997 | Docoslis et al. |
| 5,643,742 A | 7/1997 | Malin et al. |
| 5,725,563 A | 3/1998 | Klotz |
| 5,766,934 A | 6/1998 | Guiseppi-Elie |
| 5,800,467 A | 9/1998 | Park et al. |
| 5,801,055 A | 9/1998 | Henderson |
| 5,810,725 A | 9/1998 | Sugihara et al. |
| 5,824,494 A | 10/1998 | Feldberg |
| 5,851,489 A | 12/1998 | Wolf et al. |
| 5,981,268 A | 11/1999 | Kovacs et al. |
| 6,033,628 A | 3/2000 | Kaltenbach |
| 6,051,422 A | 4/2000 | Kovacs et al. |
| 6,132,683 A | 10/2000 | Sugihara et al. |
| 6,169,394 B1 | 1/2001 | Frazier et al. |
| 6,232,062 B1 | 5/2001 | Keyyem et al. |
| 6,235,520 B1 | 5/2001 | Malin et al. |
| 6,280,586 B1 | 8/2001 | Wolf et al. |
| 6,288,527 B1 | 9/2001 | Sugihara et al. |
| 6,368,795 B1 | 4/2002 | Hefti |
| 6,368,851 B1 | 4/2002 | Baumann et al. |
| 6,376,233 B1 | 4/2002 | Wolf et al. |
| 6,377,057 B1 | 4/2002 | Borkholder et al. |
| 6,440,662 B1 | 8/2002 | Gerwen et al. |
| 6,448,030 B1 | 9/2002 | Rust et al. |
| 6,448,794 B1 | 9/2002 | Cheng et al. |
| 6,461,808 B1 | 10/2002 | Bodner et al. |
| 6,472,144 B2 | 10/2002 | Malin et al. |
| 6,485,905 B2 | 11/2002 | Hefti |
| 6,492,175 B1 | 12/2002 | Muller et al. |
| RE37,977 E | 2/2003 | Sugihara et al. |
| 6,535,822 B2 | 3/2003 | Mansky et al. |
| 6,566,079 B2 | 5/2003 | Hefti |
| 6,573,063 B2 | 6/2003 | Hochman |
| 6,596,499 B2 | 7/2003 | Jalink |
| 6,626,902 B1 | 9/2003 | Kucharczyk et al. |
| 6,627,461 B2 | 9/2003 | Chapman et al. |
| 6,630,359 B1 | 10/2003 | Caillat et al. |
| 6,637,257 B2 | 10/2003 | Sparks |
| 6,638,743 B2 | 10/2003 | Baumann et al. |
| RE38,323 E | 11/2003 | Sugihara et al. |
| 6,649,402 B2 | 11/2003 | Van der Weide et al. |
| 6,686,193 B2 | 2/2004 | Maher et al. |
| 6,716,620 B2 | 4/2004 | Bashir et al. |
| 6,723,523 B2 | 4/2004 | Lynes et al. |
| 6,803,229 B2 | 10/2004 | Martin et al. |
| 6,835,552 B2 | 12/2004 | Miles et al. |
| 6,846,639 B2 | 1/2005 | Miles et al. |
| 6,852,525 B1 | 2/2005 | Cantor |
| 6,998,249 B1 | 2/2006 | McKim et al. |
| 7,010,347 B2 | 3/2006 | Schecter |
| 7,192,752 B2 | 3/2007 | Xu et al. |
| 7,208,279 B2 | 4/2007 | Gilchrist et al. |
| 7,294,334 B1 | 11/2007 | Michal et al. |
| 7,399,631 B2 | 7/2008 | Giaever et al. |
| 7,459,303 B2 | 12/2008 | Wang et al. |
| 7,468,255 B2 | 12/2008 | Xu et al. |
| 7,470,533 B2 | 12/2008 | Xu et al. |
| 7,476,827 B1 | 1/2009 | Bhuller et al. |
| 7,510,699 B2 | 3/2009 | Black et al. |
| 7,553,448 B2 | 6/2009 | Kumar et al. |
| 7,560,269 B2 | 7/2009 | Wang et al. |
| 7,732,127 B2 | 6/2010 | Wang et al. |
| 7,842,246 B2 | 11/2010 | Wohlstadler et al. |
| 7,876,108 B2 | 1/2011 | Abassi et al. |
| 8,026,080 B2 | 9/2011 | Wang et al. |
| 8,041,515 B2 | 10/2011 | Wang et al. |
| 8,206,903 B2 | 6/2012 | Bassi et al. |
| 8,263,375 B2 | 9/2012 | Abassi et al. |
| 8,344,742 B2 | 1/2013 | Abassi et al. |
| 8,420,363 B2 | 4/2013 | Wang et al. |
| 8,916,357 B2 | 12/2014 | Abassi et al. |
| 8,921,041 B2 | 12/2014 | Wang et al. |
| 9,399,787 B2 | 7/2016 | Abassi et al. |
| 9,612,234 B2 | 4/2017 | Li et al. |
| 9,625,472 B2 | 4/2017 | Xu et al. |
| 9,709,548 B2 | 7/2017 | Wang et al. |
| 10,067,121 B2 | 9/2018 | Abassi et al. |
| 2002/0032531 A1 | 3/2002 | Mansky et al. |
| 2002/0076690 A1 | 6/2002 | Miles et al. |
| 2002/0086280 A1 | 7/2002 | Lynes et al. |
| 2002/0090649 A1 | 7/2002 | Chan et al. |
| 2002/0110847 A1 | 8/2002 | Baumann et al. |
| 2002/0150886 A1 | 10/2002 | Miles et al. |
| 2003/0032000 A1 | 2/2003 | Liu et al. |
| 2003/0072549 A1 | 4/2003 | Facer et al. |
| 2003/0104512 A1 | 6/2003 | Freeman et al. |

(56) References Cited

U.S. PATENT DOCUMENTS

| | | |
|---|---|---|
| 2003/0116447 A1 | 6/2003 | Surridge et al. |
| 2003/0143625 A1 | 7/2003 | Martin et al. |
| 2003/0157587 A1 | 8/2003 | Gomez et al. |
| 2003/0166015 A1 | 9/2003 | Zarowitz et al. |
| 2003/0211500 A1 | 11/2003 | Woosley |
| 2004/0091397 A1 | 5/2004 | Picard |
| 2004/0106095 A1 | 6/2004 | Thomson et al. |
| 2004/0146849 A1 | 7/2004 | Huang et al. |
| 2005/0014130 A1 | 1/2005 | Liu et al. |
| 2005/0153425 A1 | 7/2005 | Xu et al. |
| 2005/0182447 A1 | 8/2005 | Schecter |
| 2005/0287065 A1 | 12/2005 | Suddarth et al. |
| 2006/0023559 A1 | 2/2006 | Xu et al. |
| 2006/0050596 A1 | 3/2006 | Abassi et al. |
| 2006/0057771 A1 | 3/2006 | Kovacs et al. |
| 2006/0121446 A1 | 6/2006 | Abassi et al. |
| 2006/0161073 A1 | 7/2006 | Singer et al. |
| 2006/0216203 A1 | 9/2006 | Fuller et al. |
| 2006/0240490 A1 | 10/2006 | Lee |
| 2007/0042347 A1 | 2/2007 | Rosen et al. |
| 2007/0087333 A1 | 4/2007 | Gruters et al. |
| 2007/0212423 A1 | 9/2007 | Epstein et al. |
| 2008/0190783 A1 | 8/2008 | Hyland |
| 2008/0286750 A1 | 11/2008 | Xu et al. |
| 2009/0017465 A1 | 1/2009 | Xu et al. |
| 2009/0142790 A1 | 6/2009 | Fang et al. |
| 2009/0241698 A1 | 10/2009 | Biksacky |
| 2010/0029506 A1 | 2/2010 | Wang et al. |
| 2011/0231103 A1 | 9/2011 | Fang |
| 2011/0300569 A1 | 12/2011 | Li et al. |
| 2012/0142031 A1 | 6/2012 | Xu et al. |
| 2012/0295253 A1 | 11/2012 | Abassi et al. |
| 2012/0322050 A1 | 12/2012 | Abassi et al. |
| 2013/0123136 A1 | 5/2013 | Abassi et al. |
| 2014/0203818 A1 | 6/2014 | Wang et al. |
| 2015/0125894 A1 | 5/2015 | Laing |
| 2015/0185206 A1 | 7/2015 | Abassi et al. |
| 2015/0231634 A1 | 8/2015 | Szita et al. |
| 2017/0205391 A1 | 7/2017 | Li et al. |
| 2017/0269062 A1 | 9/2017 | Abassi et al. |
| 2017/0315131 A1 | 11/2017 | Xu et al. |
| 2017/0370907 A1 | 12/2017 | Abassi et al. |
| 2018/0246079 A1 | 8/2018 | Wang et al. |

FOREIGN PATENT DOCUMENTS

| | | |
|---|---|---|
| EP | 1 040 345 B1 | 3/2006 |
| EP | 2213721 | 8/2010 |
| EP | 2291645 | 9/2015 |
| WO | 1996/01836 | 1/1996 |
| WO | 1999/66329 | 12/1999 |
| WO | 2000/37628 | 6/2000 |
| WO | 2000/70343 | 11/2000 |
| WO | 2000/71669 | 11/2000 |
| WO | 2001/25769 | 4/2001 |
| WO | 2001/038873 | 5/2001 |
| WO | 2001/79529 | 10/2001 |
| WO | 2002/004943 | 1/2002 |
| WO | 2002/042766 | 5/2002 |
| WO | 2003/016887 | 2/2003 |
| WO | 2004/010103 | 1/2004 |
| WO | 2005/005979 | 1/2005 |
| WO | 2005/047482 | 5/2005 |
| WO | 2005/077104 | 8/2005 |
| WO | 2006/017762 | 2/2006 |
| WO | 2009/137440 | 11/2009 |
| WO | 2010/129725 | 11/2010 |
| WO | 2011/146531 | 11/2011 |
| WO | 2012/043820 | 4/2012 |
| WO | 2014/085727 | 6/2014 |
| WO | 2017/068421 A1 | 4/2017 |
| WO | 2017/087945 A1 | 5/2017 |

OTHER PUBLICATIONS

Yang et al., A novel microfluidic impedance assay for monitoring endothelin-induced cardiomyocyte hypertrophy, Biosensors and Bioelectronics 22 (2007) p. 1688-1693.*

Chang, Bin-Wha, et al. "Impedimetric monitoring of cell attachment on interdigitated microelectrodes." Sensors and Actuators B: Chemical 105.2 (2005): 159-163.*

Klauke, Norbert, Godfrey L. Smith, and Jon Cooper. "Extracellular recordings of field potentials from single cardiomyocytes." Biophysical journal 91.7 (2006): 2543-2551.*

Bauman et al., Microelectronic sensor system for microphysical application on living cells, Sensors and Actuators, 1999:77-89.

Berens et al., The role of extracelluar matrix in human astrocytoma migration and proliferation studied in a microliter scale assay, Clin. Exp. Metastasis, 1994; 12(6):405-415.

Bieberich et al., Neuronal differentiation and synapse formation of PC12 and embryonic stem cells on interdigitated microelectrode arrays: Contact structures for neuron-to-electrode signal transmission (NEST), Biosensors and Bioelectronics 2004; 19:923-931.

Burnett et al., Fluorescent imaginng of electrically stimulated cells, Journal of Biomolecular Screening 2003; 8(6):660-667.

Cady et al., Electrical Impedance Measurements: Rapid Method for Detecting and Monitoring Microorganisms, J. Clin. Mirobiol., 1978; 7(3):265-272.

Ehret et al., Monitoring of cellular behaviour by impedance measurements on interdigitated electrode structures, Biosensors and Bioelectronics 1997; 12(1):29-41.

Ehret et al., On-line control of cellular adhesion with impedance measurements using interdigitated electrode structures, Med. Biol. Eng. Comput., 1998; 36:365-370.

Giaever et al., Micromotion of mammalian cells measured electrically, Proc. Natl. Acad. Sci. USA, 1991; 8(Sept.):7896-7900.

Giaever et al., Monitoring fibroblast behavior in tissue culture with an applied electric field, Proc. Natl. Acad. Sci. USA; 1984; 81(June):3761-3764.

Henning et al., Approach to a mutliparametric sensor-chip-based tumor chemosensitivity assay, Anti-Cancer Drugs 2001; 12:21-32.

Hidalgo et al., Characterization of the human colon carcinoma cell line (Caco-2) as a model system for intestinal epithelial Permeability, 1989; 96:736-749.

Hug, Thomas, Biophysical methods for monitoring cell-substrate interactions in drug discovery, Assay and Drug Development Technologies, 2003; 1(3):479-488.

Kleinman et al., Basement membrane complexes with biological activity, Biochemistry 1986; 25(2):312-318.

Kowolenko et al., Measurement of macrophage adherence and spreading with weak electric fields, Journal of Immunological Methods, 1990; 127:71-77.

Lo et al., Monitoring motion of confluent cells in tissue culture, Experimental Cell Research 1983; 204:102-109.

Luong et al., Monitoring motility, spreading and mortality of adherent insect cells using an impedance sensor, Anal. Chem 2001; 73(8):1844-1848.

Neher, Erwin, Molecular biology meets microelectronics, Nature Biotechnology, 2001; 19:114.

Ong et al., Remote query resonant-circuit sensors for monitoring of bacterial growth: Application to food quality control, Sensors 2002; 2:219-232.

Pancrazio et al., Portable cell-based biosensor system for toxin detection, Sensors and Actuators 1998; 53:179-185.

Slaughter et al., Artificial neural network for temporal impedance recognition of neurotoxins, 2006 International Joint Conference on Neural Networks 2006; Jul. 16-21, 2001-2008.

Stenger et al., Detection of physiologically active compounds using cell-based biosensors, Trends in Biotechnology, 2001; 19(8):304-309.

Wang et al., A theoretical method of electrical field analysis for dielectrophoretic electrode arrays using Green's theorem, J. Phys. D: Appl. Phys 1996; 29:1649-1660.

Wegener et al., Electric cell-substrate impedance sensing (ECIS) as noninvasive means to monitor the kinetics of cell spreading to artificial surfaces, Experimental Cell Research 2000; 259:158-166.

(56) References Cited

OTHER PUBLICATIONS

Wolf et al., Monitoring of cellular signalling and metabolism with modular sensor-technique: The PhysioControl-Microsystem (PCM), Biosensors and Bioelectronics 1998; 13:501-509.
Xiao et al., Assessment of cytotoxicity using electric cell-substrate impedance sensing: Concentration and time response function approach, Anal. Chem 2002, 74:5748-5753.
Xiao et al., An in-depth analysis of electric cell-substrate impedance sensing to study the attachment and spreading of mammalian cells, Anal. Chem 2002; 74(6):1333-1339.
Xiao et al., On-line monitoring of cell growth and cytotoxicity using electric cell-substrate impedance sensing (ECIS), Biotechnol, Prog, 2003; 19:1000-1005.
Aravanis et al. "A genetically engineered cell-based biosensor for functional classification of agents." Biosensors & Bioelectronics, 2001, 16:571-577.
Baumann et al. "Microelectronic sensor system for microphysiological application on living cells." Sensors & Accuators, 1999, B55:77-89.
Becker et al. "Separation of human breast cancer cells from blood by differential dielectric affinity." Cell Biology, 1995, 92:960-964.
Berens et al. "The role of extracellular matrix in human astrocytoma migration and proliferation studied in a microliter scale assay." Clin. Exp. Metastasis, 1994, 12:405-415.
Bergveld, P. "A critical evaluation of direct electrical protein detection methods." Biosensors & Bioelectronics. 6:55-72 (1991).
Burns et al. "Neutrophil Transendothelial Migration Is Independent of Tight Junctions and Occurs Preferentially at Tricellular Corners." Journal of Immunology, 1997, 2893-2903.
Ciambrone et al. "Cellular Dielectric Spectroscopy: A Powerful New Approach to Label-Free Cellular Analysis." J. Biomo. Screening, 2004, 9(6):467-480.
Duan et al. "Separation-Free Sandwich Enzyme Immunoassays Using Microporous Gold Electrodes and Self-Assembled Monolayer/Immobilized Capture Antibodies." Anal. Chem., 1994, 66:1369-1377.
Gutmann et al. "Evidence for Different ABC-Transporters in Caco-2 Cells Modulating Drug Uptake." Pharmaceutical Research, 1999, 16(3):402-407.
Hug, Thomas S. "Biophysical Methods for Monitoring Cell-Substrate Interactions in Drug Discovery." Assay and Drug Dev. Tech., 2003, 1(3):479-488.
Lin and Huang. "Electroporation microchips for in vitro gene transfection." J. Micromech. Microeng., 2001,11:542-547.
Lin et al. "Simulation and experimental demonstration of the electric field assisted electroporation microchip for in vitro gene delivery enhancement." Min. for Chem., Bio., & Bioeng., 2004, 4:104-108.
Lo et al. "Impedance Analysis of MDCK cells measured by electric cell-substrate impedance sensing." Biophysical Journal, 1995, 69:2800-2807.
Mitra et al. "Electric measurements can be used to monitor the attachment and spreading of cells in tissue culture." Biotechniques, 1991, 11(4):504-510.
Miyata et al. "New Wound-Healing Model Using Cultured Corneal Endothelial Cells." Jpn. J. Opthalmol., 1990, 34:257-266.
Mohr et al. "Performance of a thin film microelectrode array for monitoring electrogenic cells in vitro." Sensors and Actuators, 1996, B34:265-269.
Nerurkar et al. "The Use of Surfactants to Enhance the Permeability of Peptides Through Caco-2 Cells by Inhibition of an Apically Polarized Efflux System" Pharmaceutical Research, 1996,13(4):528-534.
"Molecular Viewer" New Products page. Science, 298:2409 (2002).
"Cell Migration Studies with TECAN Systems." TECAN., Sep. 1999, [retrieved from the internet] http://www.tecan.com/migration_introl.pdf, 10 pgs.
"Detect Cell Migration and Invasion in a Homogeneous Fluorescent Assay System." BD Biosciences, [retrieved from the internet] http://www.bdbiosciences.com/discovery_labware/Products/inserts/BD_Falcon_HTS_fluoroblok_inserts/individual_fluoroblok_inserts/index.html, 2004.
"Neuro Probe AA96, AB96, AC96 Chemotaxis Chambers." Neuro Probe, [retrieved from the internet] http://www.neuroprobe.com/protocol/pt_96a.html, 5 pgs.
"Automated Cell Monitoring Instrument." Applied BioPhysics, 2002, [retrieved from the internet] http://www.biophysics.com/pages/front.html, 1 page.
Yamauchi et al. "Spatially and temporally controlled gene transfer by electroporation into adherent cells on plasmid DNA-loaded electrodes." Nuc. Acids Res., 2004, 32(22):1-8.
Yang et al. "Celli Separation on Microfabricated Electrodes Using dielectrophoretic/Gravitational field-flow Fractionation." Anal. Chem., 1999, 71:911-918.
Connolly et al. "An extracellular microelectrode array for monitoring electrogenic cells in culture." Biosensors & Bioelectronics, 1990, 5:223-234.
Falk et al. "A 48-well Micro Chemotaxis Assembly for Rapid and Accurate Measurement of Leukocyte Migration." J. Immunol. Meth., 1980, 33:239-247.
Fuhr et al. "Positioning and Manipulation of Cells and Microparticles Using Miniaturized Electric Field Traps and Travelling Waves." Sensors and Materials 7(2):131-146 (1995).
Hadjout et al., Automated Real-Time Measurement of Chemotactic Cell Motility Biotechniques 31:1130-1138 (2001).
Huang et al., Dielectrophoretic Cell Separation and Gene Expression Profiling on Microelectronic Chip Arrays. Anal. Chem. 74:3362-3371 (2002).
Keese et al., Real-time impedance assay to follow the invasive activities of metastatic cells in culture. Biotechniques, 2002, 33:842-850.
Larsen et al. "Somatic Cell Counting with Silicon Apertures." Micro Total Analysis Systems, 2000, 103-106.
Lo et al. "pH Changes in pulsed $CO_2$ incubators cause periodic changes in cell morphology." Experimental Cell Research, 213:391-397 (1994).
Wegener et al. "Electric cell-substrate impedance sensing system (ECIS) as a noninvasive means to monitor the kinetics of cell spreading to artificial surfaces." Eur. J. Physiol., 1999, 437:925-934.
Banach et al. "Development of Electrical Activity in Cardiac Myocyte Aggregates Derived from Mouse Embryonic Stem Cells." Am J Physiol Heart Circ Physiol, 2003, 284: H2114-H2123.
Hescheler et al. "Determination of Electrical Properties of ES Cell-derived Cardiomyocytes Using MEAs." Journal of Electrocardiology, 2004, vol. 37, Suppl.
Horvath et al. "Monitoring of Living Cell Attachment and Spreading Using Reverse Symmetry Waveguide Sensing." Applied Physics Letters, 2005, 86:071101.
Berdondini et al. "High-density electrode array for imaging in vitro electrophysiological activity." Biosensors and Bioelectronics, 2005, 21:167-174.
Chang et al. "Impedimetric monitoring of cell attachment on interdigitated microelectrodes." Sensors and Actuators, 2005, B 105:159-163.
Yang et al. "A novel microfluidic impedance assay for monitoring endothelin-induced cardiomyocyte hypertrophy." Biosensors and Bioelectronics, 2007, 22:1688-1693.
PCT/US2009/033801 International Search Report and Written Opinion dated Jul. 9, 2010.
PCT/US2009/042787 International Search Report and Written Opinion dated Jun. 24, 2009.
PCT/US2011/036877 International Search Report dated Sep. 2, 2011.
PCT/US2013/072439 International Search Report dated Feb. 19, 2014.
PCT/US2005/034561 International Preliminary Report on Patentability dated Mar. 27, 2007.
PCT/US2005/034561 International Search Report dated Sep. 27, 2006.
PCT/US2005/027943 International Preliminary Report on Patentability dated Apr. 11, 2007.

(56) References Cited

OTHER PUBLICATIONS

PCT/US2005/027943 International Search Report and Written Opinion dated Mar. 21, 2007.
PCT/US2004/037696 International Search Report dated May 16, 2005.
PCT/US2005/04481 International Search Report dated Sep. 12, 2005.
EP05722991 Extended European Search Report dated Apr. 3, 2009.
EP11193882 Extended European Search Report dated Apr. 5, 2012.
EP13171137 Extended European Search Report dated Aug. 16, 2013.
EP05786773 Extended European Search Report dated Mar. 21, 2013.
EP05852157 Extended European Search Report dated Sep. 13, 2011.
EP058122680 Extended European Search Report dated Sep. 7, 2011.
EP03748948 Extended European Search Report dated Mar. 12, 2007.
CA2556219 Office Action dated Aug. 9, 2010.
CA2575573 Office Action dated Apr. 4, 2012.
EP09743420 European Search Report dated Nov. 26, 2013.
Kloss et al. "Microcavity array (MCA)-based biosensor chip for functional drug screening of 3D tissue models" Biosensors and Bioelectronics, 2008, 23:1473-1480.
Oka et al. "A new planar multielectrode array for extracellular recording: application to hippocampal acute slice." Journal of Neuroscience Methods, 1999, 93:61-67, Elsevier Science, B.V.
Qiu et al. "Real-Time Monitoring Primary Cardiomyocyte Adhesion Based on Electrochemical Impedance Spectroscopy and Electrical Cell-Substrate Impedance Sensing" Anal. Chem., 2008, 80:990-996.
Yu et al. "Real-Time Monitoring of Morphological Changes in Living Cells by Electronic Cell Sensor Arrays: An Approach to Study G Protein-Coupled Receptors" Anal. Chem., 2006, 78:35-43.
Xing et al. "Dynamic Monitoring of Cytotoxicity on Microelectronic Sensors" Chem. Res. Toxicol., 2005, 18(2):154-161.
Blagbrough et al. "Polyamines and novel polyamine conjugates interact with DNA in ways that can be exploited in non-viral gene therapy." Biochemical Society Transactions, 2003, 31, Part 2, pp. 397-406.
Bonetta, Laura. "The inside scoop-evaluating gene delivery methods." Nature Methods, Nov. 2005, 2(11):875-883.
Hapala, Ivan. "Breaking the Barrier: Methods for Reversible Permeabilization of Cellular Membranes." Critical Reviews in Biotechnology, 1997, 17(2):105-122.
Loffert et al. "Multiplex PCR with QIAGEN: TAq DNA Plymerase and PCR Buffer." QIAGENews, 1994, 4:15-18.
Luan and Li. "Clustering of time-course gene expression data using a mixed-effects model with B-splines." Bioinformatics, 2003, 19(4):474-482.
Nicoazzi et al. "Cationic Lipids for Transfection." Current Medicinal Chemistry, 2003, 10:1263-1277.
Rabow et al. "Mining the National Cancer Institute's Tumor-Screening Database: Identification of Compounds with Similar Cellular Activities." J. Med. Chem., 2002, 45:818-840.
Steinem et al. "Impedance and shear wave resonance analysis of ligand-receptor interactions at functionalized surfaces and of cell monolayers." Biosensors & Bioelectronics, 1997, 12(8):787-808.
Patolsky et al., Detection of single-base Dna mutations by enzyme-amplified electronic transduction. Nature Biotechnology 19:253-257 (2001).
Pethig et al., Positive and negative dielectrophoretic collection of colloidal particles using interdigitated castellated microelectrodes. Appl. Phys. 24:881-888 (1992).
Richards et al., A Modified Microchamber Method for Chemotaxis and Chemokinesis. Immunological Communications 13 (1):49-62.
Rishpon et al., An Amperometric Enzyme-channeling Immunosensor. Biosensors & Bioelectronicsd, 12(3):195-204 (1997).
Simpson et al. "Whole-cell biocomputing." Trends in Biotechnology, 2001, 19(9):317-323.
Sohn et al. "Capacitance cytometry: Measuring biological cells one by one." Proc. Nat. Acad. Sci., 2000, 97(20):10687-10690.
Svetlicic et al. "Charge Displacement by adhesion and spreading of a cell." Bioelectrochemistry, 2000, 53:79-86.
Tiruppathi et al. "Electrical method for detection of endothelial cell shape change in time: assessment of endothelial barrier function." Proc Natl Acad Sci USA, 1992, 89:7919-7923.
Wang et al. "Selective Dielectrophoretic confinement of bioparticles in potential energy wells." Appl. Phys., 1993, 26:1278-1285.
Wang et al. "Cell Separation by Dielectrophoretic Field-flow-fractionation." Anal. Chem., 2000, 72:832-839.
Wang et al. "Dielectrophoretic Manipulation of Cells with Spiral Electrodes." Biophysical Journal, 1997, 72:1887-1899.
Wang et al. "Separation of Polystyrene Microbeads Using Dielectrophoretic/Gravitational Field-Flow-Fractionation." Biophysical Journal, 1998, 74:2689-2701.
Wang et al. "Electronic Manipulation of Cells on Microchip-Based Devices." In Biochip Technology (eds), pp. 135-159, Harwood Academic Publishers, PA, USA.
Warburg Ueber die Polarisationscapacitat des Platins. Ann. Phys., 6:125-135 (1901).
Wegener et al., Use of electrochemical impedance measurements to monitor beta-adrenergic stimulation of bovine aortic endothelial cells, Eur. J. Physiol., 437:925-934 (1999).
10772804.0 Extended European Search Report dated Oct. 27, 2017.
Lo et al. "Abstract C1.00268: Effect of cMet Inhibitor on HGF-Induced Ovarian Carcinoma Cell Migration," American Physical Societal March Meeting, 2010, Portland, Oregon, vol. 55, No. 2, poster session.
Oka et al. "A New Planar Multielectrode Array for Extracellular Recording: Application to Hippocampal Acute Slice." Journal of Neuroscience Methods, 1999, 93:61-67.
HP 4284A Precision LCR Meter Operation Manual, Aug. 1998, Hewlett Packard, 6th Edition, p. 1-460.
Fusenig et al. "The Need for a Worldwide Consensus for Cell Line Authentication: Experience Implementing a Mandatory Requirement at the Internation Journal of Cancer". PLOS Biologiy, Apr. 17, 2017, 15(4) p. e2001438 pp. 1-13.
Lin et al. "Simulation and Experimental Demonstration of the Electric Field Assisted Electroporation Microchip for In Vitro Gene Delivery Enhancement." Miniaturisation for Chemistry, Biology & Bioengineerin., 2004, 4:104-108.
Sohn et al. "Capacitance Cytometry: Measuring Biological Cells One by One." Proceedings of the National Academy of Sciences, 2000, 97(20):10687-10690.
PCT/US2016/063066 ISR and WO dated Jan. 30, 2017.
PCT/US2018/044774 ISR and WO dated Oct. 23, 2018.

* cited by examiner

Titration of ES-derived cardiomyocytes using the ACEA RT-CES system

Figure 2. Treatment of ES-derived cardiomyocytes with a cytotoxic compound of Sodium dichromate dehydrate.

Figure 3. Detection of morphological changes associated with ES-derived cardiomyocytes induced by isoproteranol, a β2 adrenergic receptor agonist, using the RT-CES system Figure 5. Detection of cardiomyocyte beating using the ACEA RT-CES system at different time periods along the growth and differentiative curve of ES-derived cardiomyocytes seeded in ACEA E-Plates. The time resolution between adjacent points in Figures 5A, 5B and 5C is about 40 milli-seconds. In another words, a second shown in Figures 5A, 5B and 5C is equivalent to 40 milli-seconds.

Fig. 5A

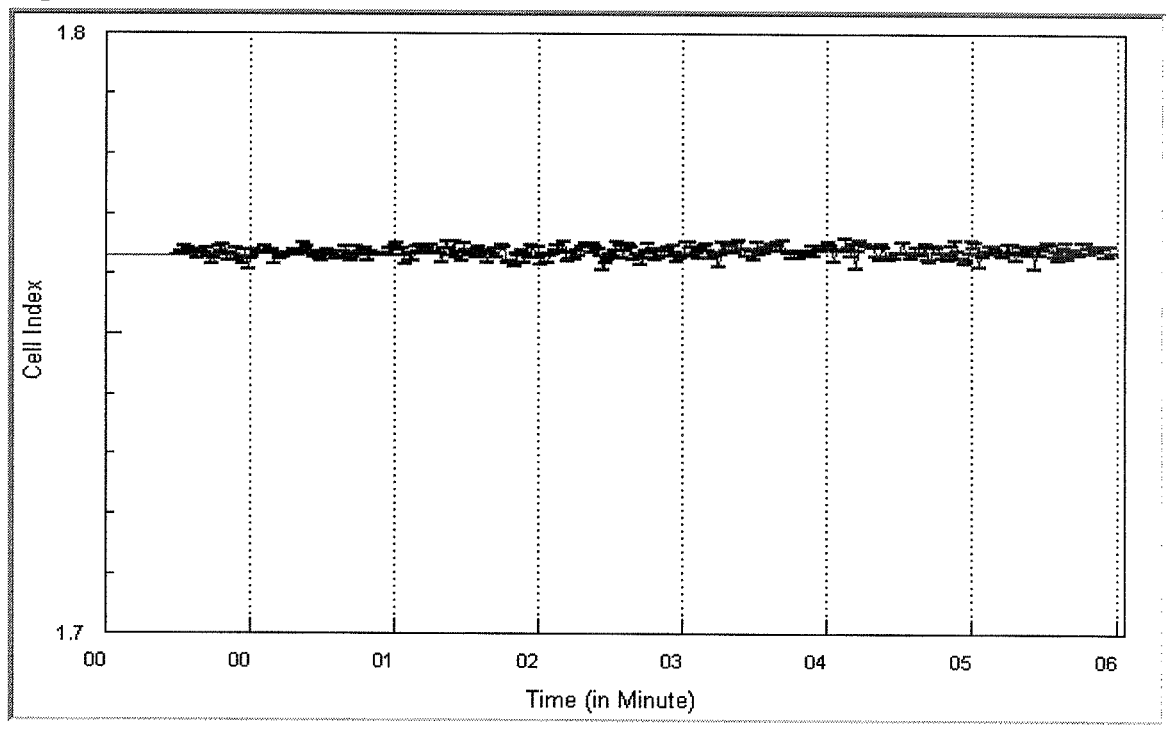

Figure 7. Detection of cardiomyocyte beating using the ACEA RT-CES system for the mouse cardiomyocytes treated with 4.4 uM sotalol. In Figures 7C and 7D, the time resolution between two adjacent points is 40 milli-seconds. In another word, a second in Figures 7C and 7D is equivalent to 40-milli-second.

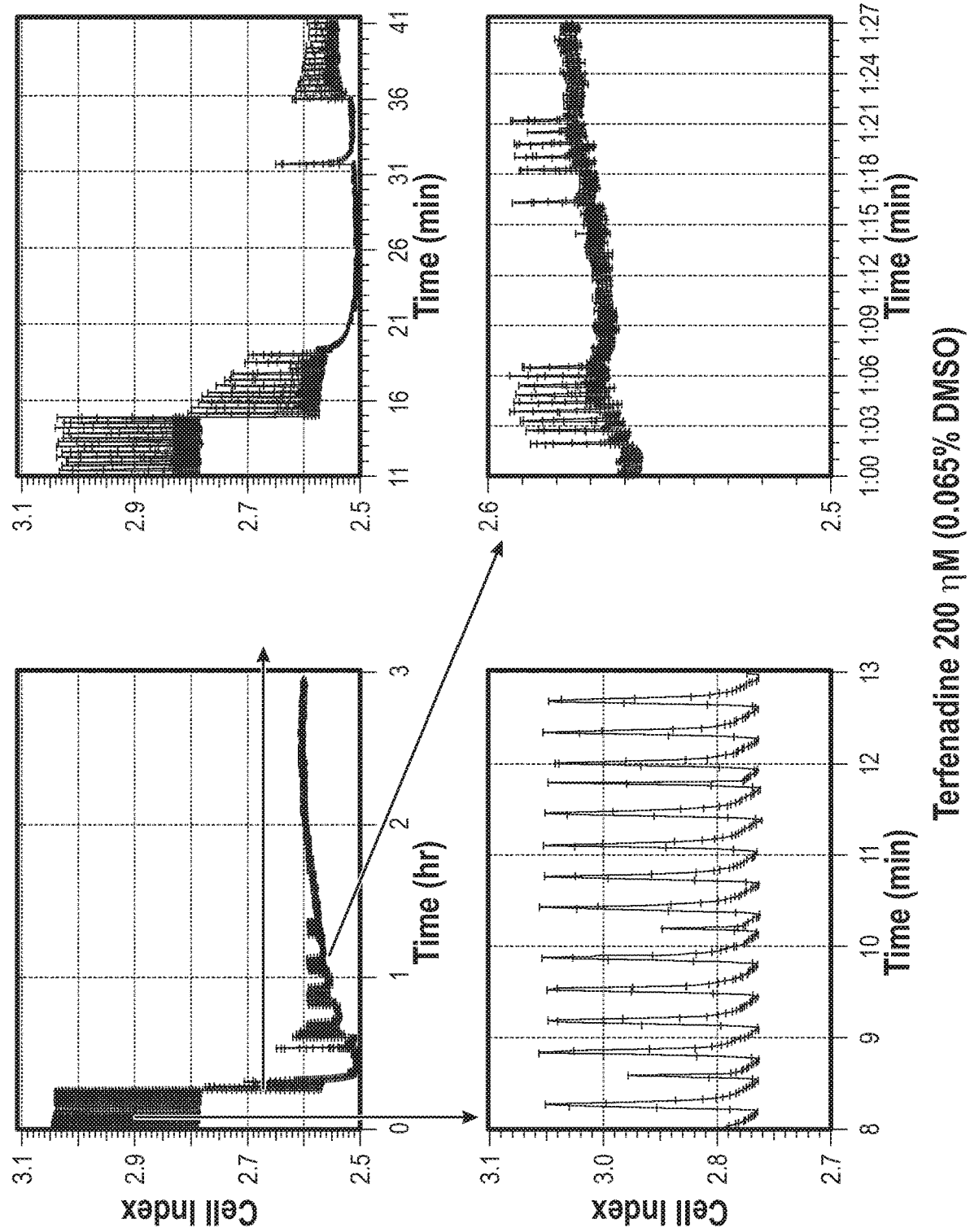

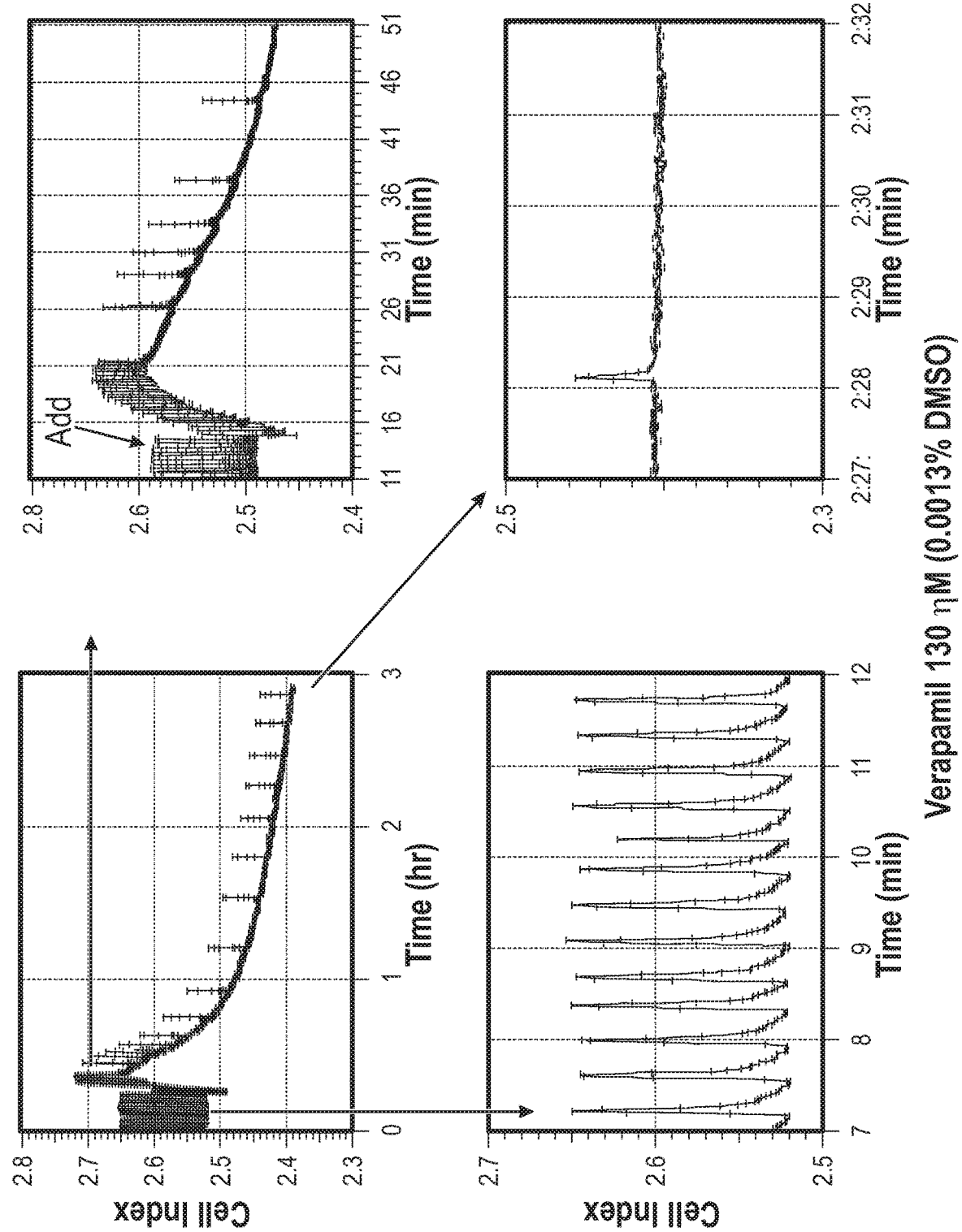

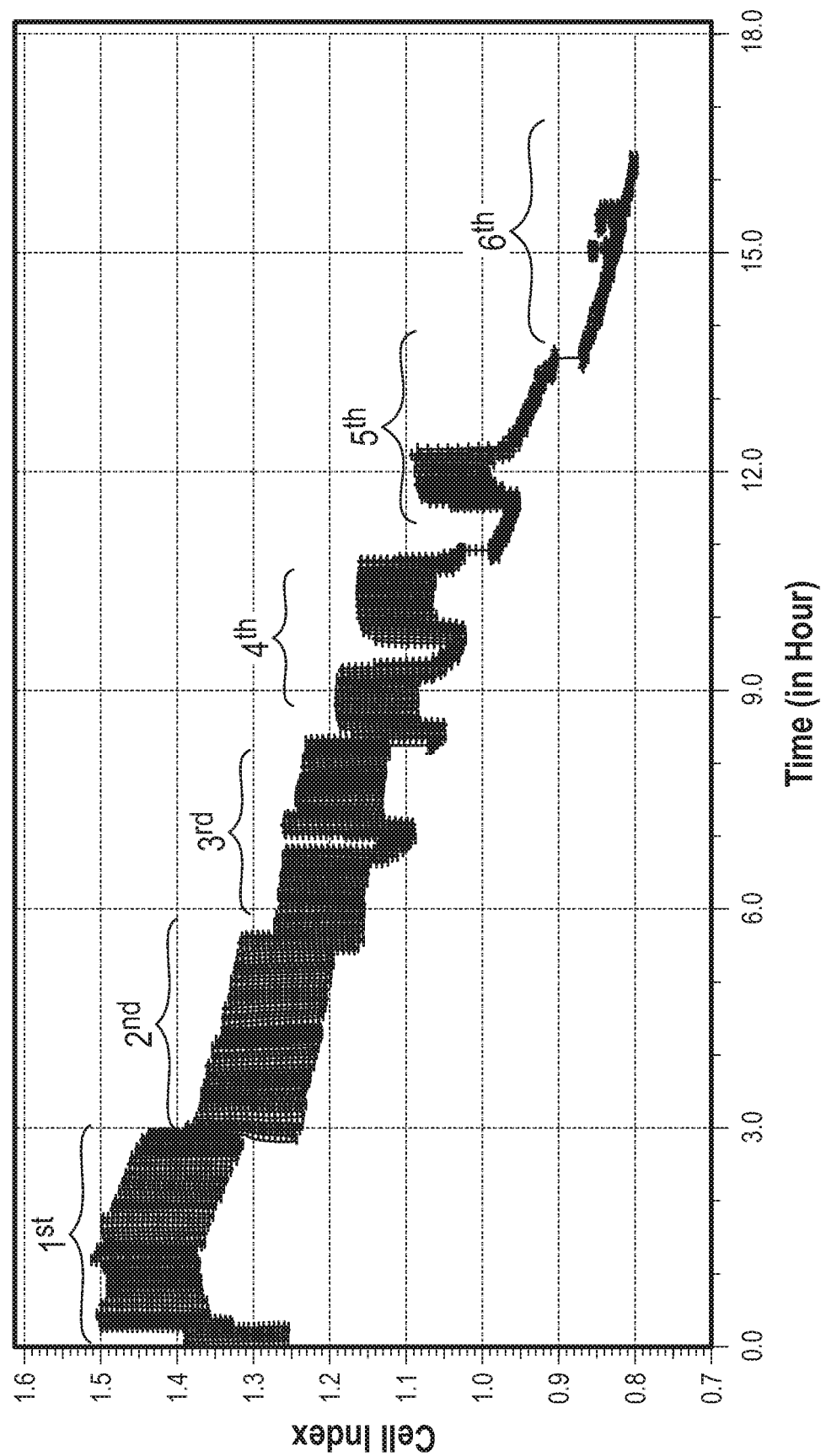
FIG. 9J Refecoxib 13.3 μM

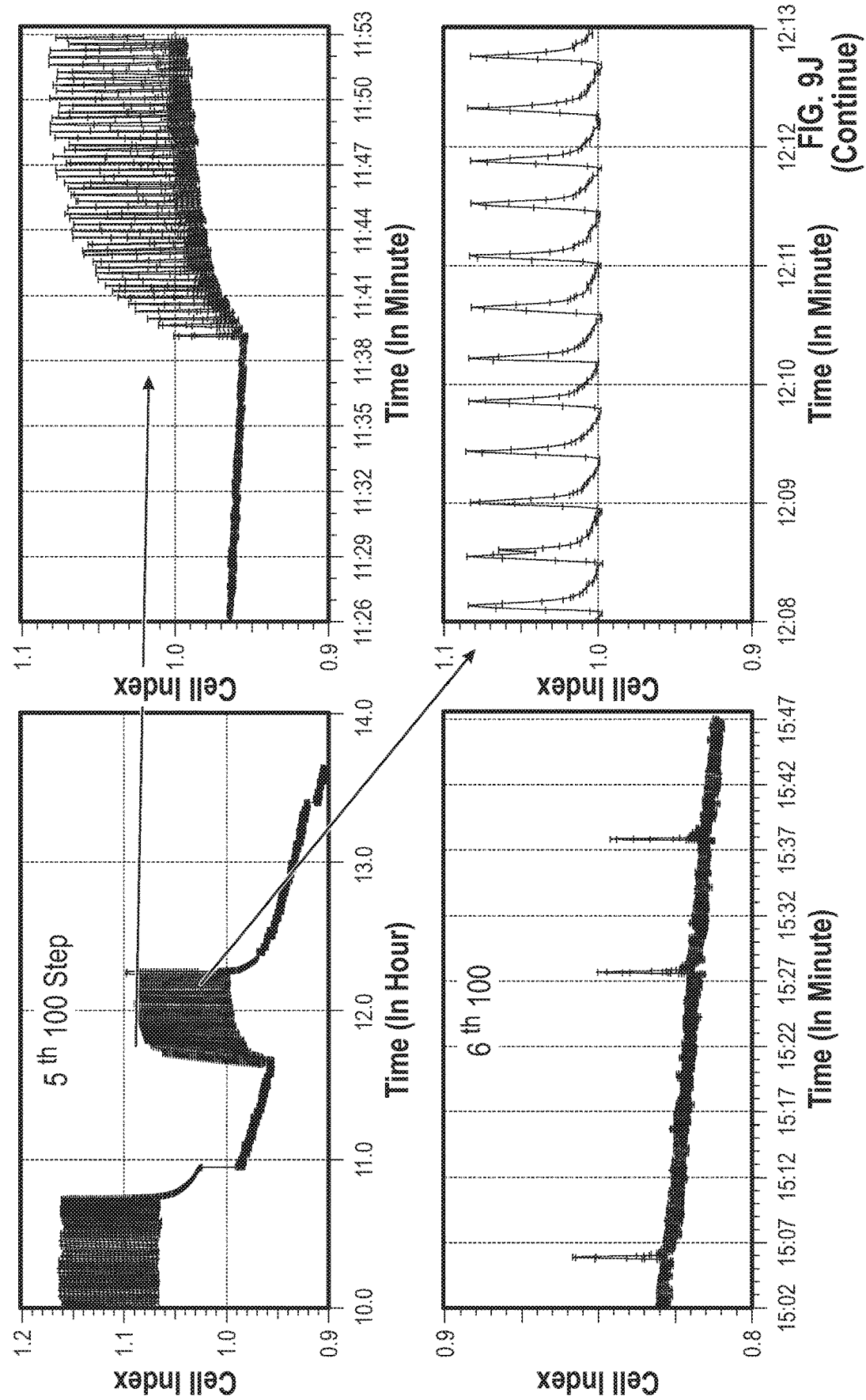
FIG. 9J (Continue)

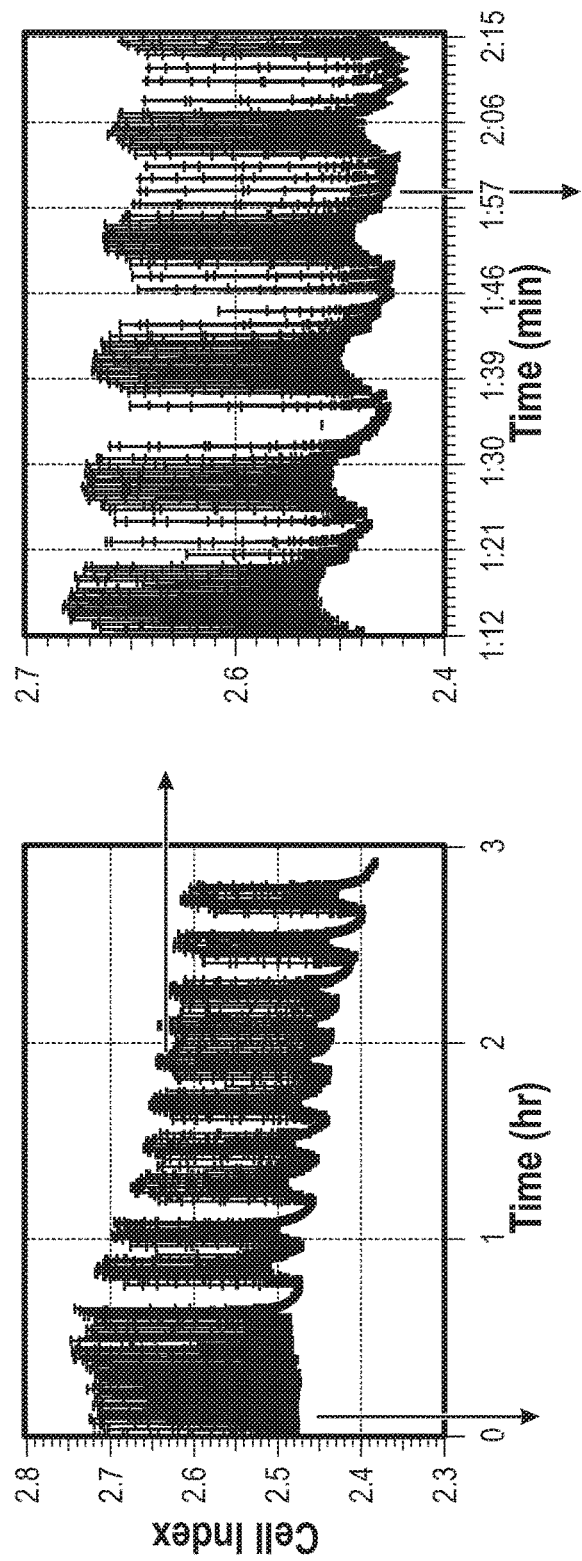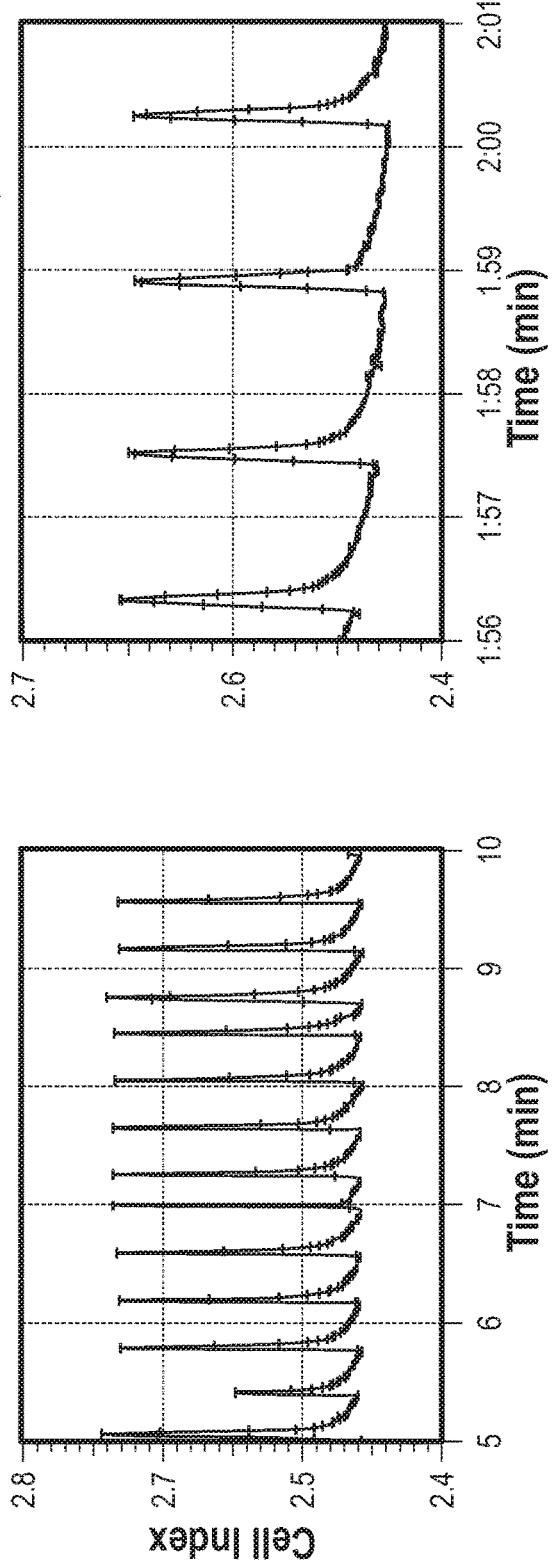
FIG. 9K
Celecoxib 4.4 μM

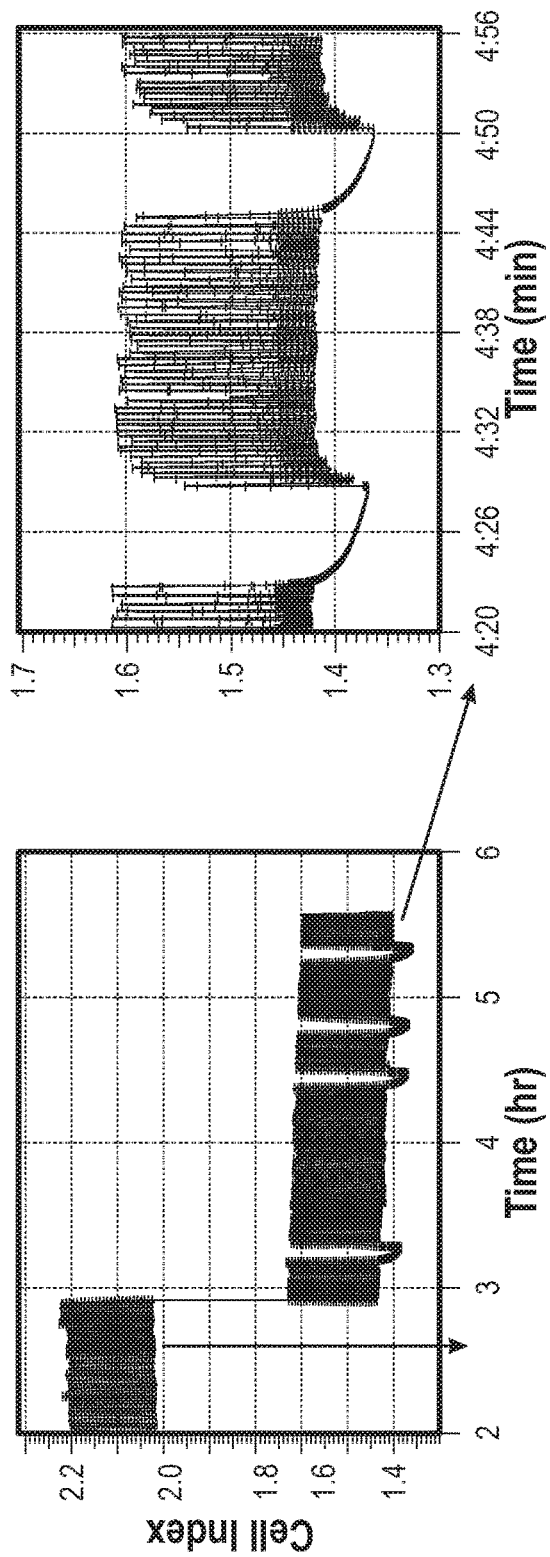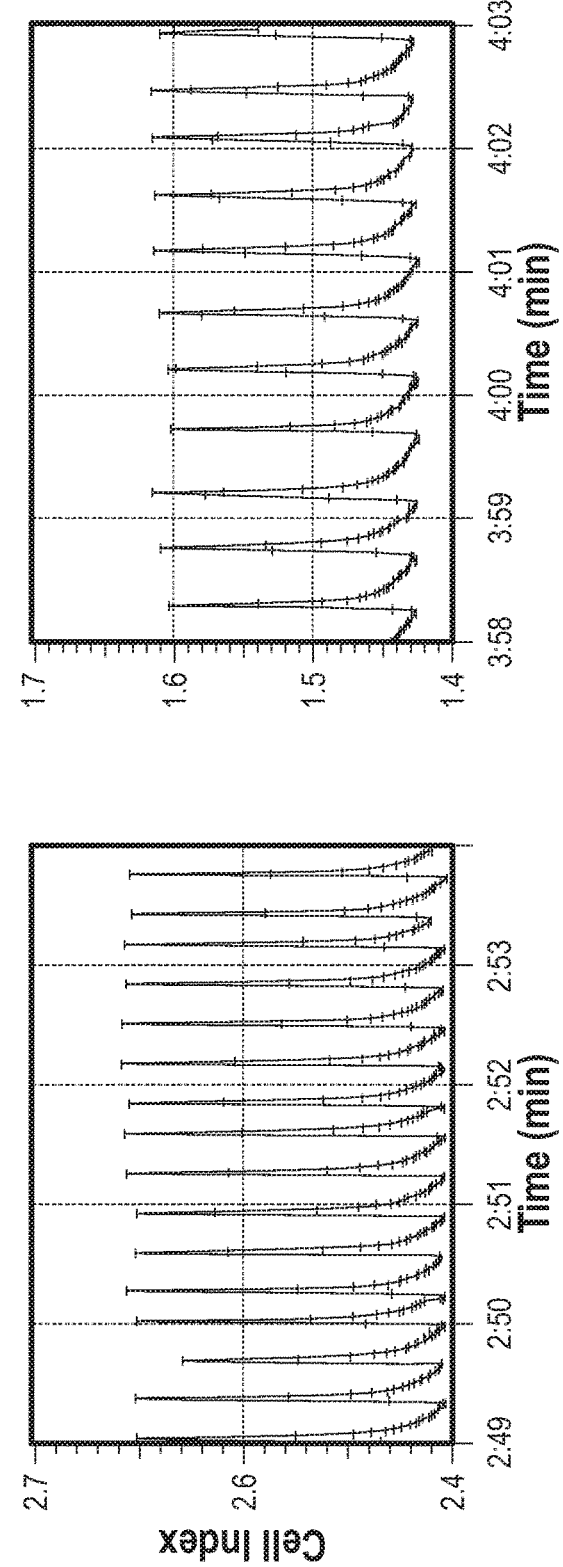
FIG. 9L

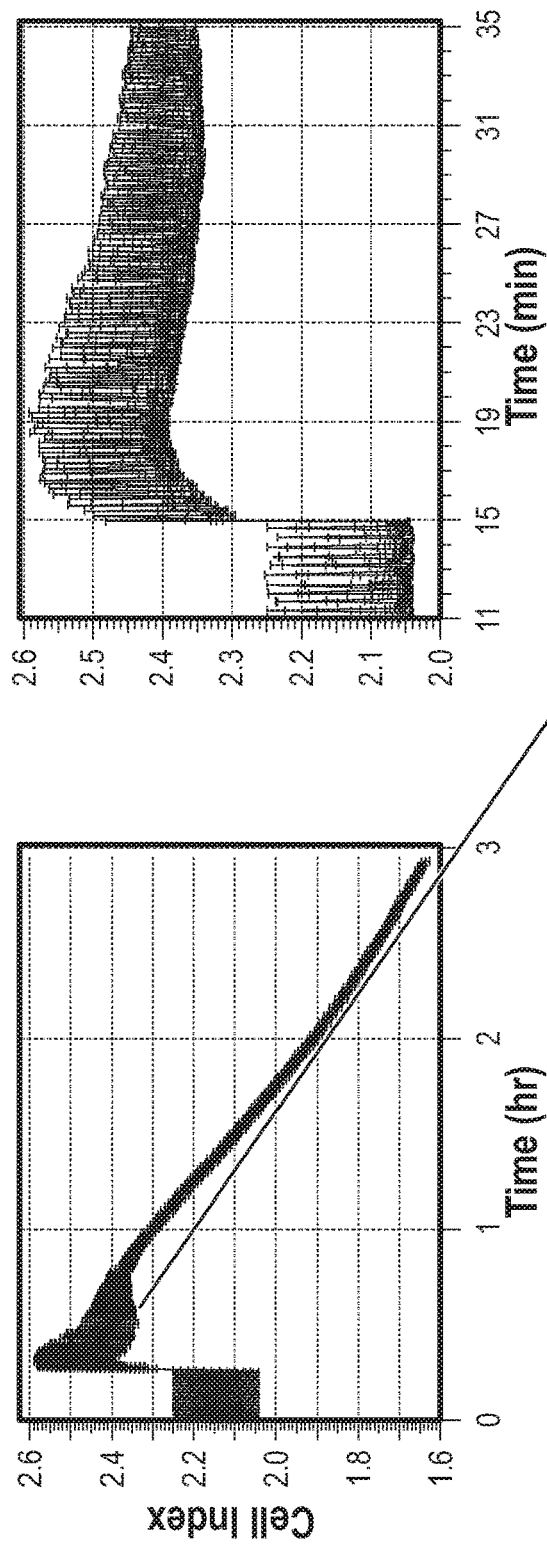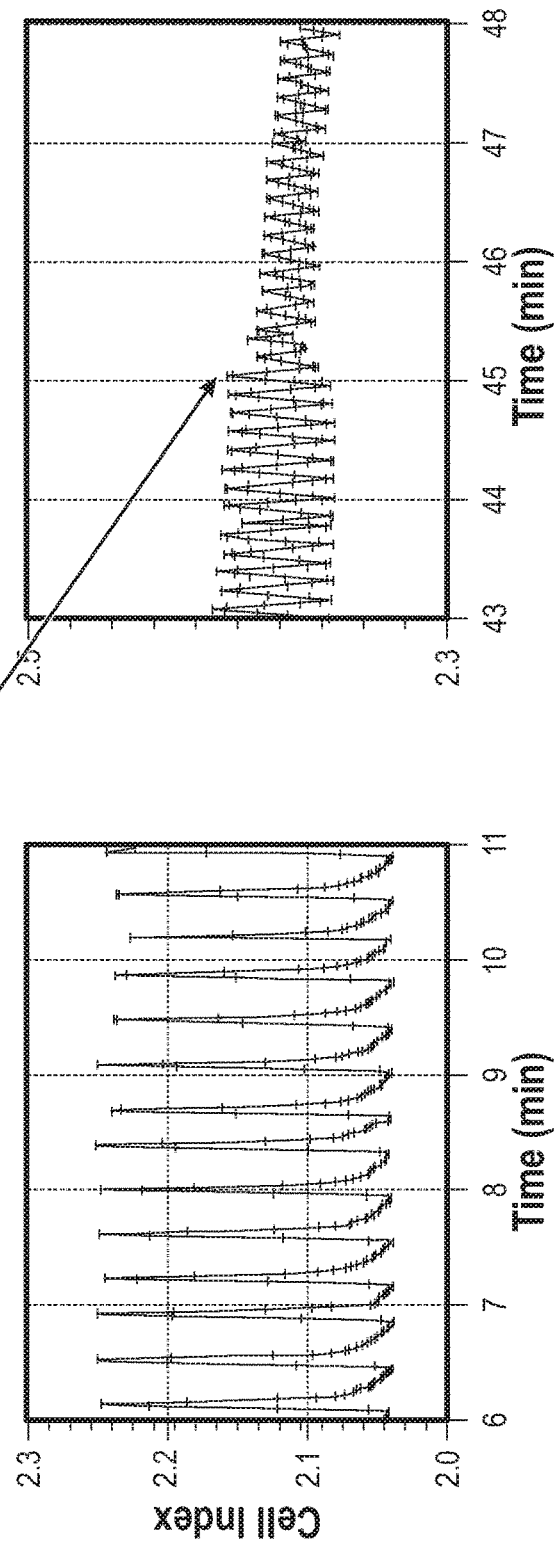
FIG. 9Q

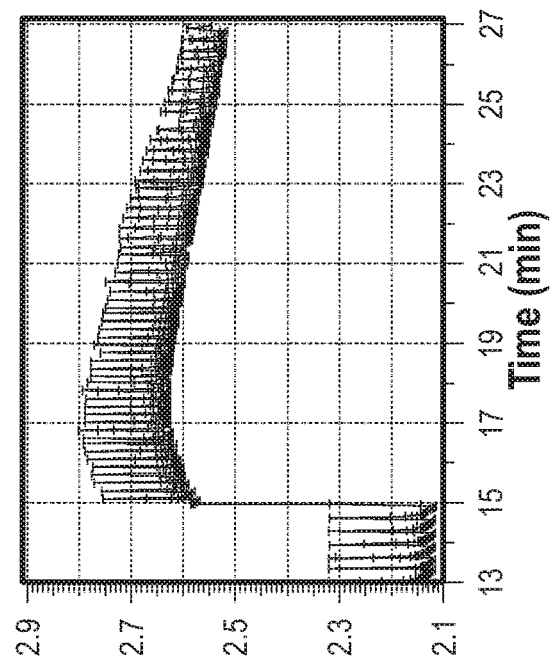
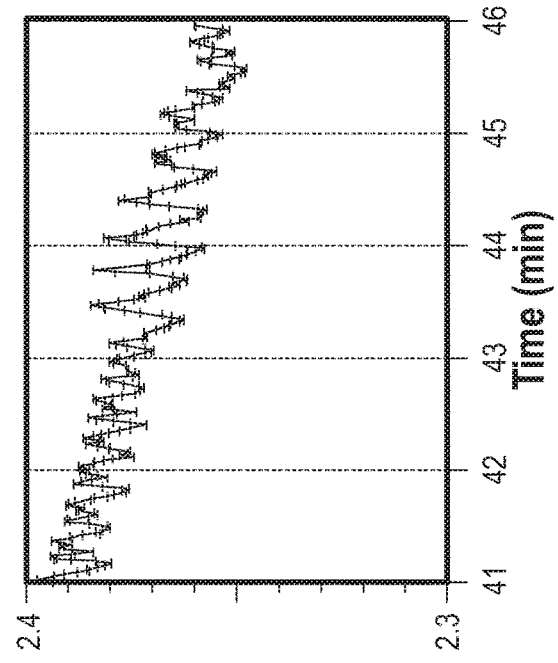
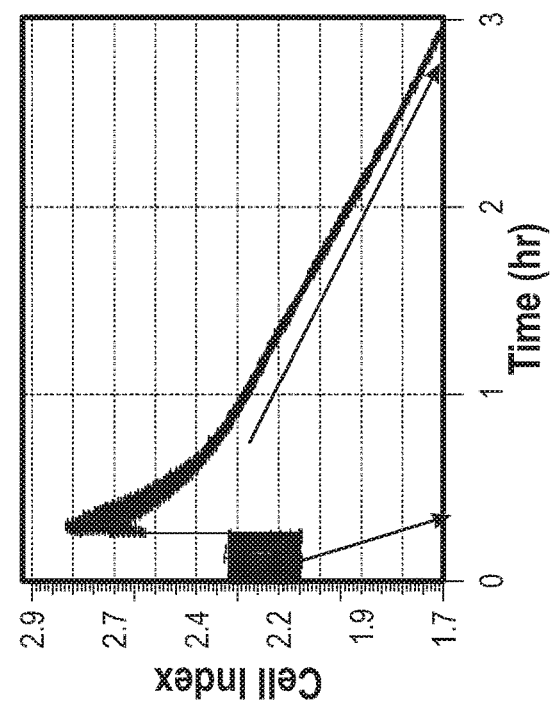
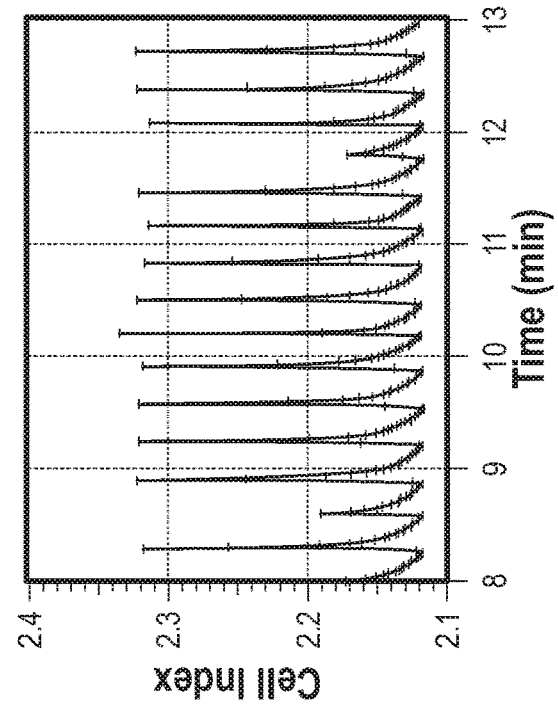
Endosulfan 8μM (0.08% DMSO)
FIG. 9R

Cardiotoxic Patterns

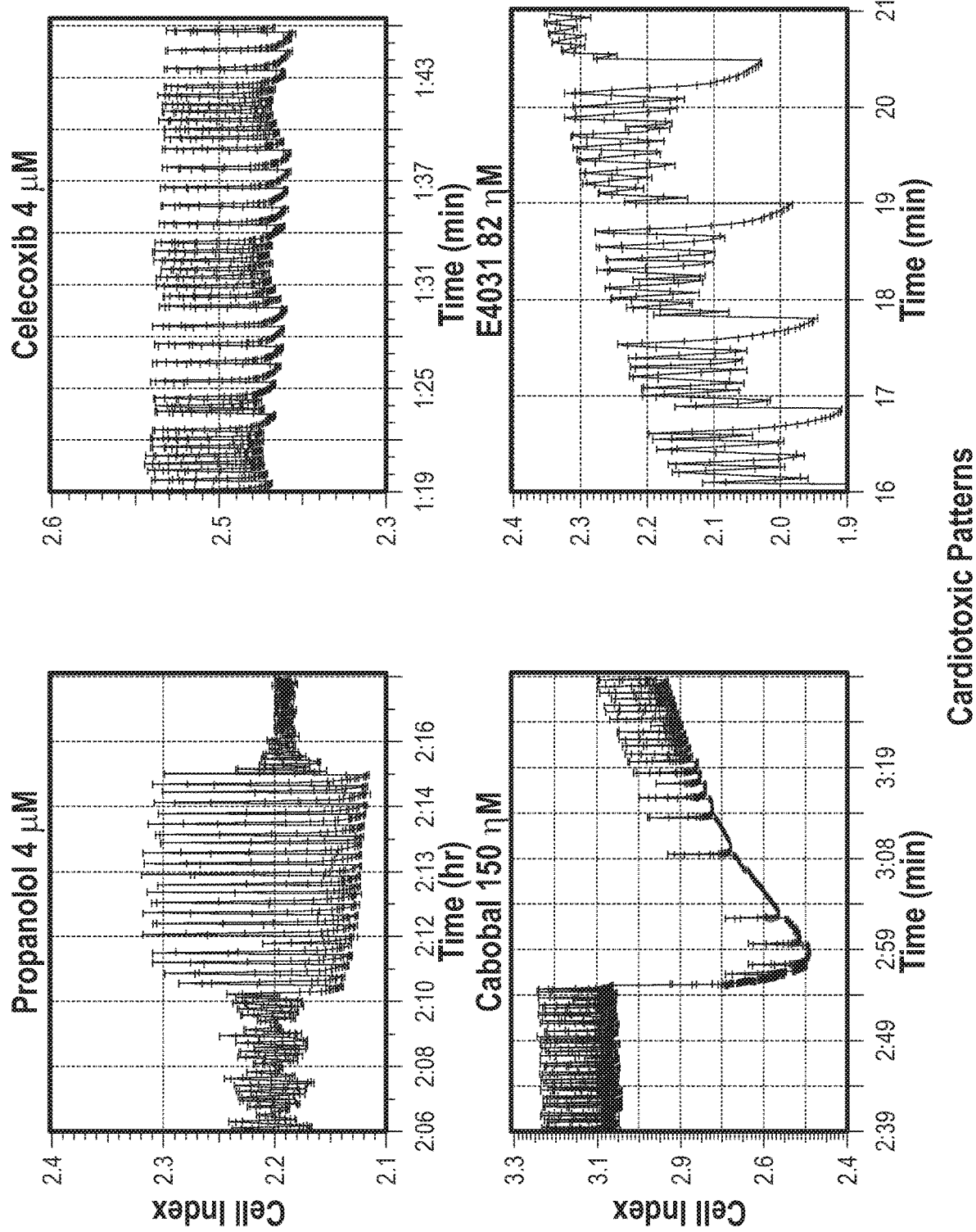
FIG. 10 (Continue)

Figure 18
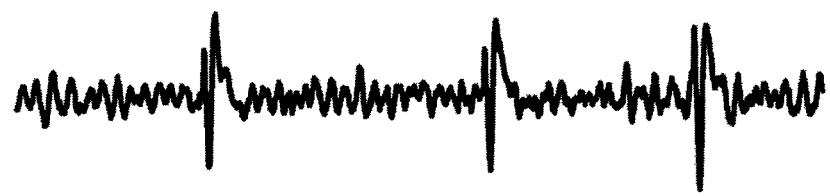
FP recorded on day 2 after cell plating
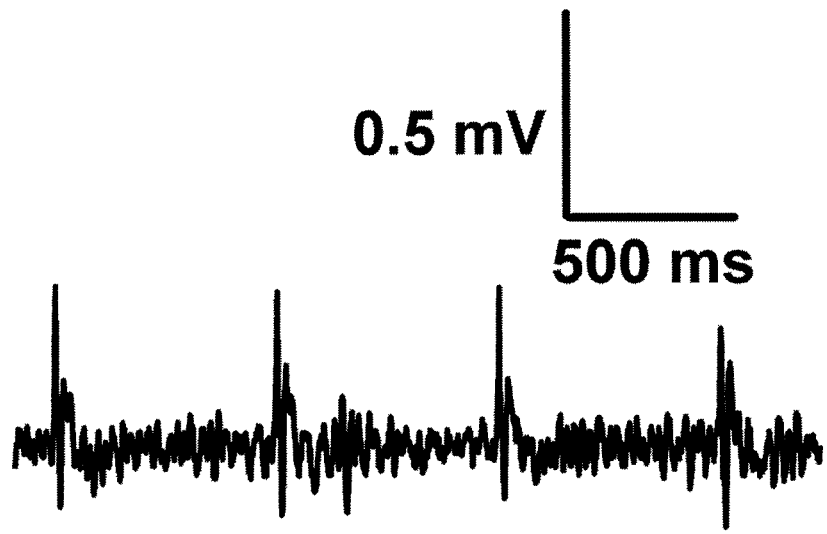
FP recorded on day 3 after cell plating Figure 22.
(A)
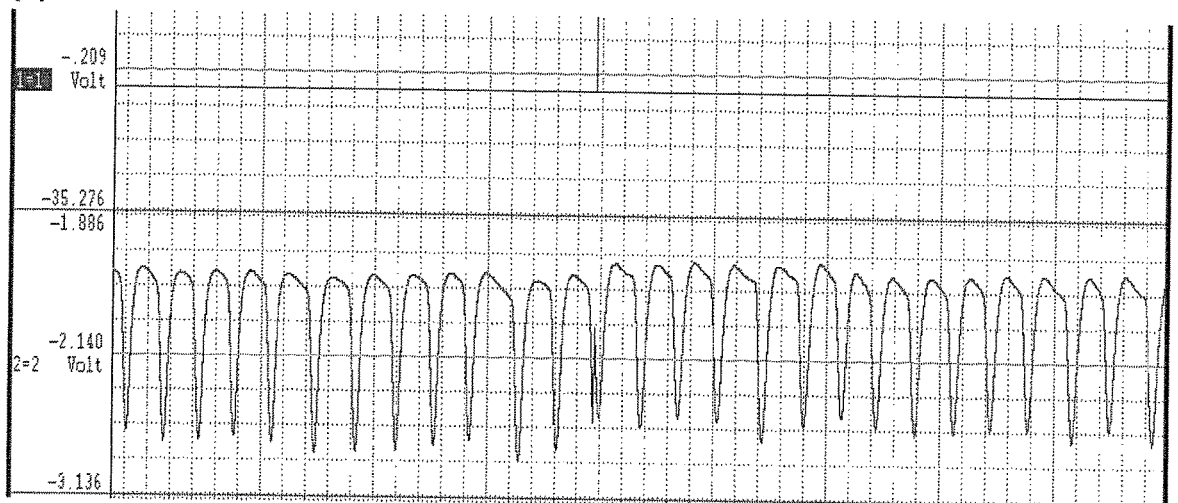
(B)
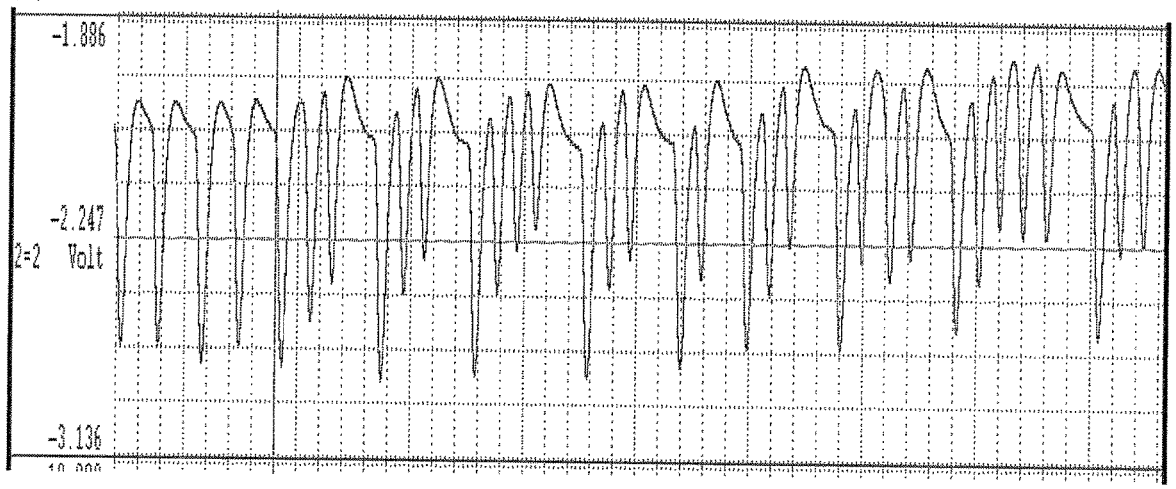

Figure 22.
(C)
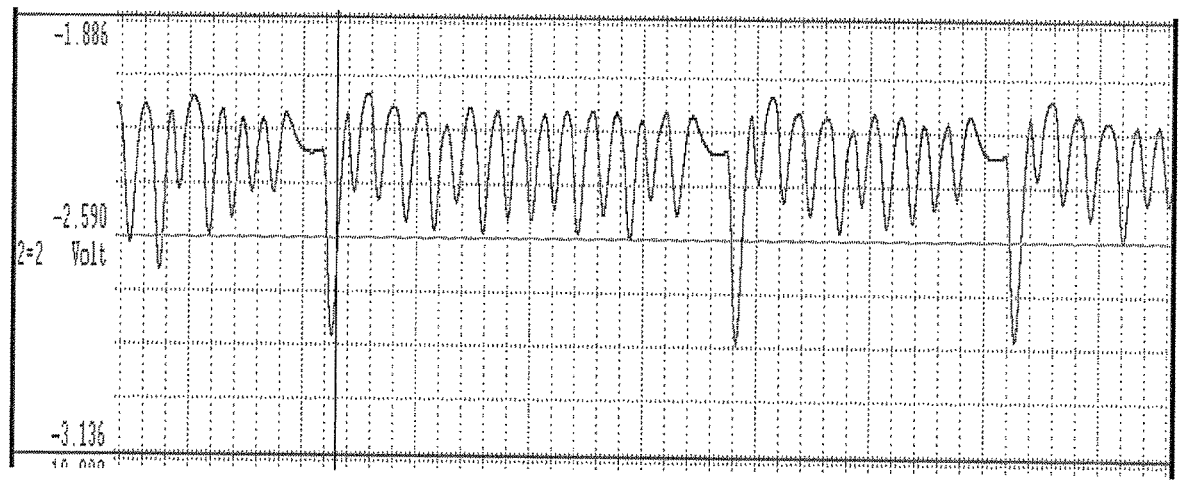
(D)
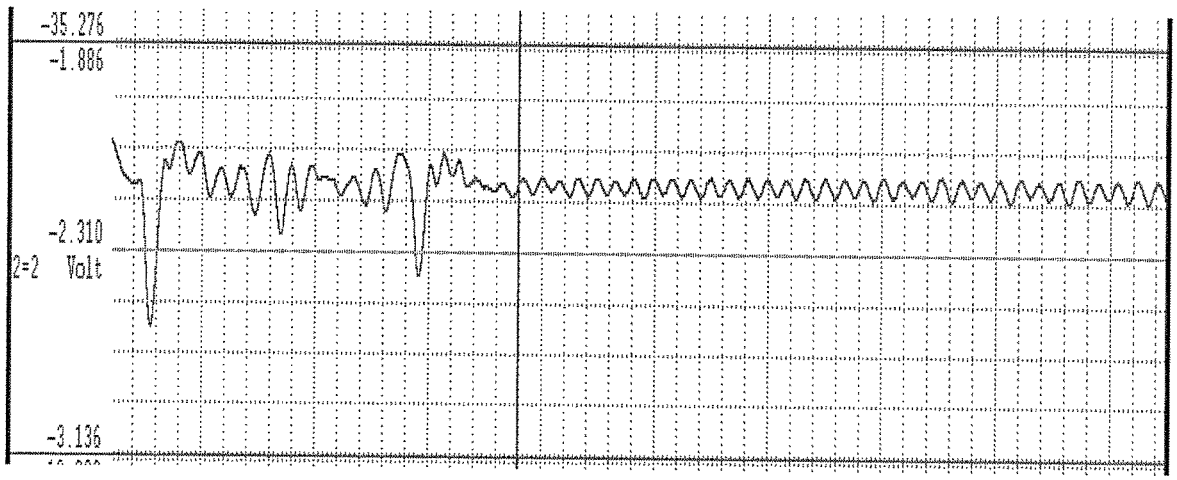

Figure 23.
(D)
(E)

Figure 24.
(A)
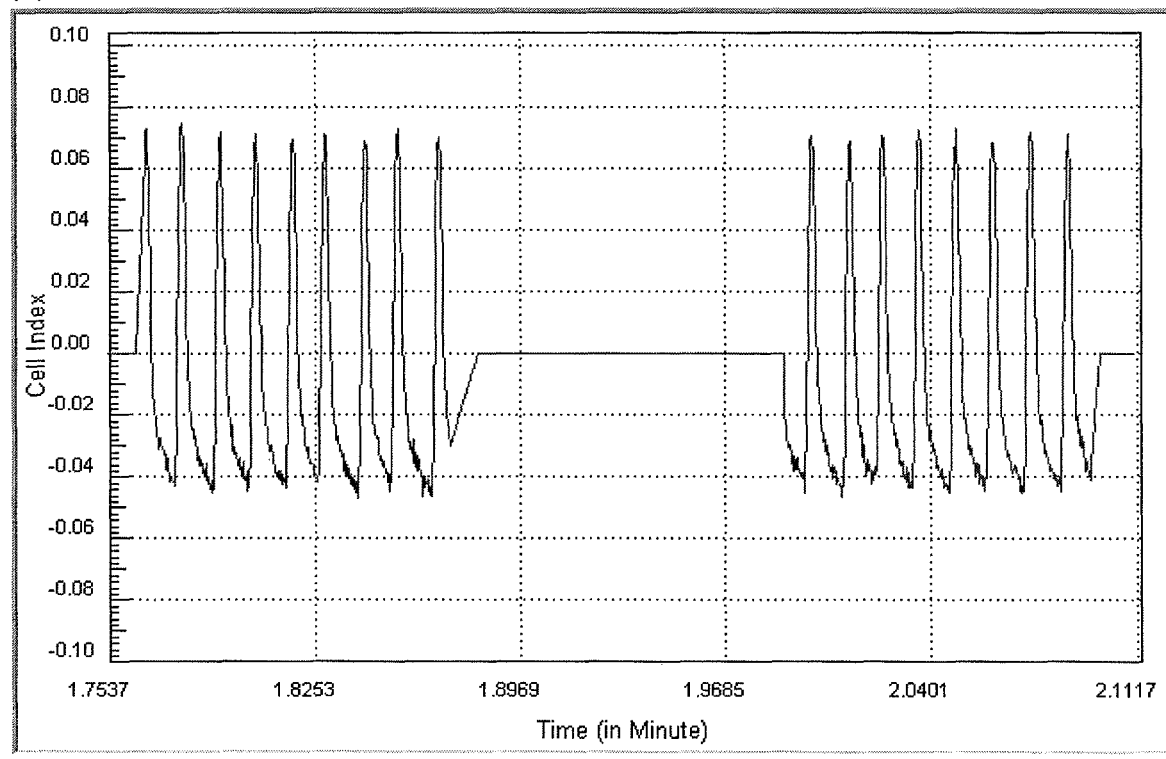
(B)
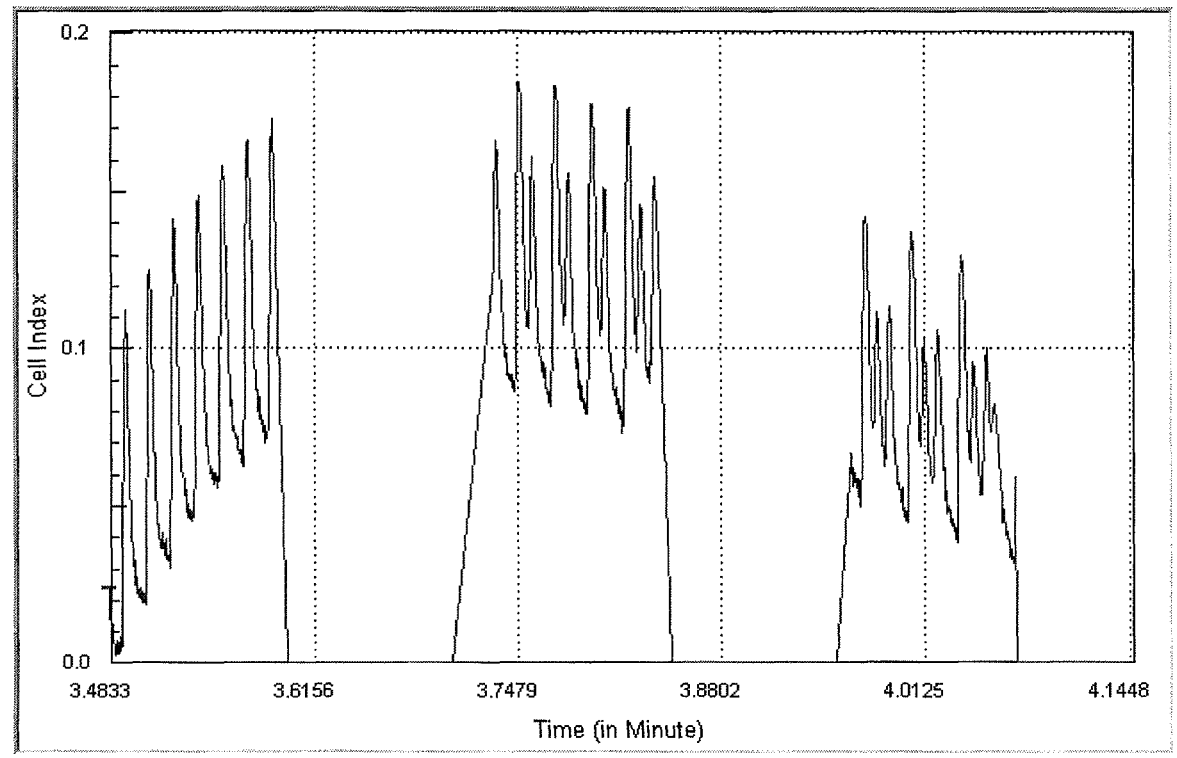

Figure 24.
(C)
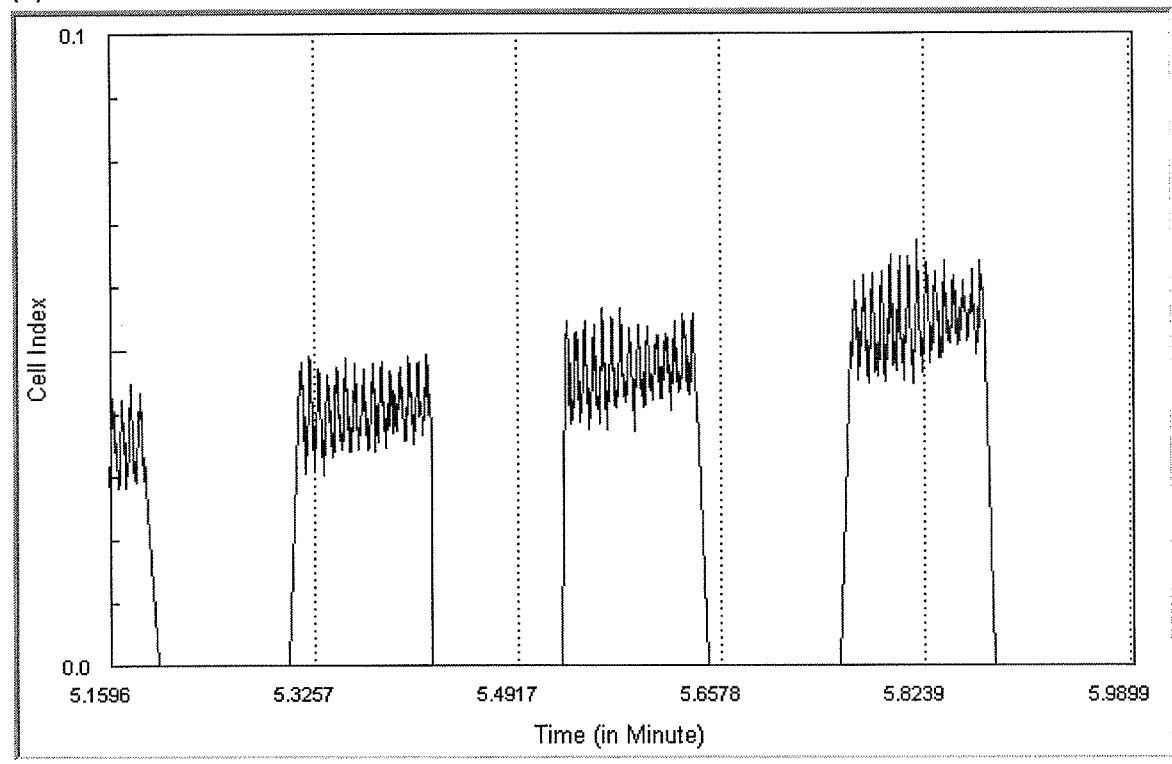
(D)
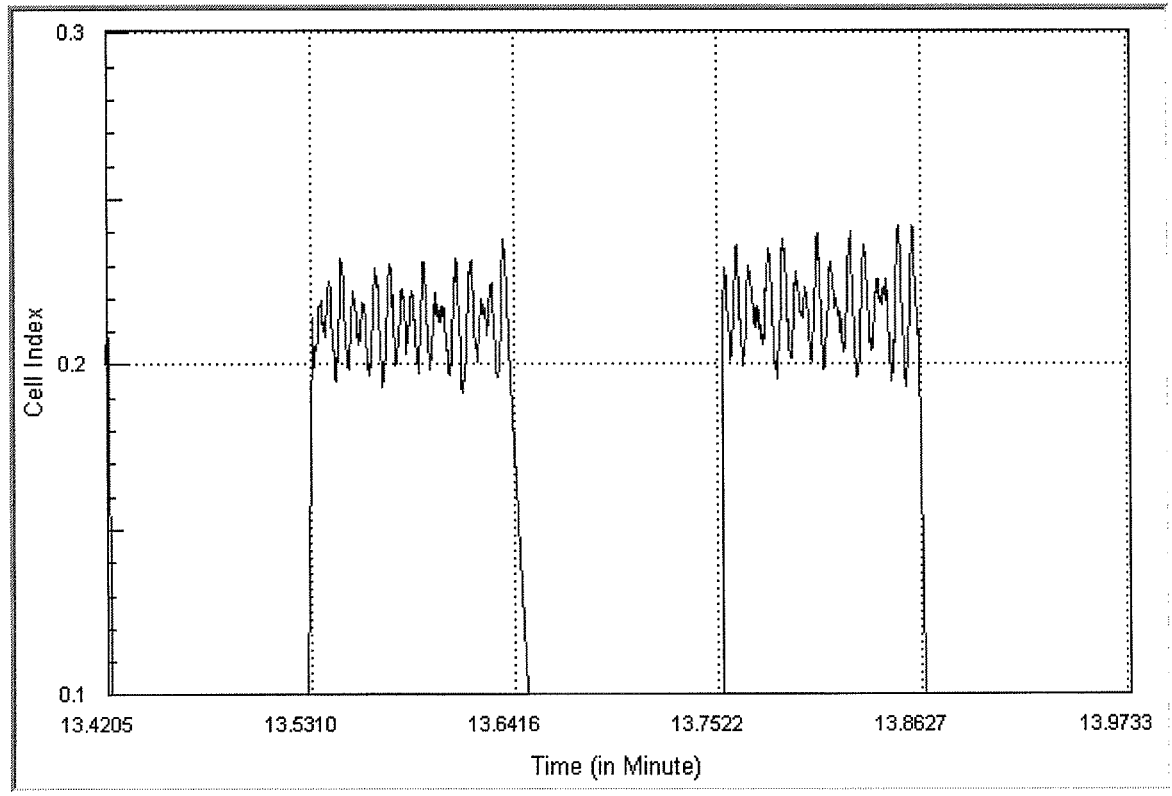

SYSTEM AND METHOD FOR MONITORING CARDIOMYOCYTE BEATING, VIABILITY AND MORPHOLOGY AND FOR SCREENING FOR PHARMACOLOGICAL AGENTS WHICH MAY INDUCE CARDIOTOXICITY OR MODULATE CARDIOMYOCYTE FUNCTION

CROSS REFERENCE TO RELATED APPLICATIONS

This application is a continuation in part of U.S. patent application Ser. No. 12/435,569, filed May 5, 2009, entitled, "Label free monitoring of excitation-contraction coupling and excitable cells using impedance based systems with millisecond time resolution," which claims priority to U.S. provisional patent application Ser. No. 61/191,684, filed Sep. 11, 2008, and U.S. provisional patent application Ser. No. 61/126,533, filed May 5, 2008; the contents of each are herein incorporated by reference in their entirety.

This application also claims priority to U.S. patent application Ser. No. 61/323,782, filed on Apr. 13, 2010, entitled, "Impedance based monitoring of cardiomyocytes"; U.S. patent application Ser. No. 61/310,557, filed Mar. 15, 2010, entitled, "Impedance based monitoring of cardiomyocytes"; and U.S. patent application Ser. No. 61/175,566, filed May 5, 2009, entitled, "System and method for monitoring cardiomyocyte beating, viability and morphology and for screening for pharmacological agents which may induce cardiotoxicity or modulate cardiomyocyte function." The contents of each are herein incorporated by reference in their entirety.

This application is also a continuation in part of U.S. patent application Ser. No. 11/235,938 entitled, "Dynamic Monitoring of Cell Adhesion and Spreading Using the RT-CES System", filed on Sep. 27, 2005 which is a continuation in part of U.S. patent application Ser. No. 11/197,994, now U.S. Pat. No. 7,468,255, entitled, "Method for Assaying for Natural Killer, Cytotoxic T-Lymphocyte and Neutrophil-Mediated Killing of Target Cells Using Real-Time Microelectronic Cell Sensing Technology", filed on Aug. 4, 2005, which is a continuation-in-part of U.S. patent application Ser. No. 11/055,639, now U.S. Pat. No. 7,560,269, entitled "Real time electronic cell sensing system and applications for cytotoxicity profiling and compound assays" filed on Feb. 9, 2005 which is a continuation-in-part of U.S. patent application Ser. No. 10/987,732, now U.S. Pat. No. 7,192,752, entitled "Real time electronic cell sensing system and application for cell based assays" filed on Nov. 12, 2004, which claims priority to U.S. provisional application Ser. No. 60/519,567, filed on Nov. 12, 2003.

All applications referred to in this paragraph are incorporated by reference in their entireties herein.

Parent U.S. patent application Ser. No. 11/235,938, also claims benefit of priority to U.S. provisional patent application Ser. No. 60/630,131, filed on Nov. 22, 2004; U.S. provisional patent application Ser. No. 60/630,071 filed on Nov. 22, 2004; U.S. provisional patent application Ser. No. 60/613,872 filed on Sep. 27, 2004; U.S. provisional patent application Ser. No. 60/613,749, filed on Sep. 27, 2004; U.S. provisional patent application Ser. No. 60/630,809 filed on Nov. 24, 2004; U.S. provisional patent application Ser. No. 60/633,019 filed on Dec. 3, 2004; U.S. provisional patent application Ser. No. 60/647,159 filed on Jan. 26, 2005; U.S. provisional patent application Ser. No. 60/653,904 filed on Feb. 17, 2005; and U.S. provisional patent application Ser. No. 60/673,678 filed on Apr. 25, 2005; U.S. provisional patent application Ser. No. 60/689,422 filed on Jun. 10, 2005. The contents of each are herein incorporated by reference in their entirety.

Parent U.S. patent application Ser. No. 11/235,938 is also a continuation-in-part of U.S. patent application Ser. No. 11/198,831, entitled, "Dynamic Monitoring of Activation of G-Protein Coupled Receptor (GPCR) and Receptor Tyrosine Kinase (RTK) in Living Cells using Real-Time Microelectronic Cell Sensing Technology, filed on Aug. 4, 2005, which is herein incorporated by reference in its entirety.

Parent U.S. patent application Ser. No. 10/987,732, now U.S. Pat. No. 7,192,752, is also a continuation-in-part of U.S. patent application Ser. No. 10/705,615, now U.S. Pat. No. 7,459,303, entitled "Impedance Based Apparatuses and Methods for Analyzing Cells and Particles", filed on Nov. 10, 2003, which claims priority to U.S. provisional patent application Ser. No. 60/397,749 filed on Jul. 20, 2002; U.S. provisional patent application Ser. 60/435,400, filed on Dec. 20, 2002; U.S. provisional patent application Ser. No. 60/469,572, filed on May 9, 2003; and PCT patent application serial number PCT/US03/22537, filed on Jul. 18, 2003. All of the applications referred to in this paragraph are incorporated by reference in their entireties herein.

Parent U.S. patent application Ser. No. 10/987,732, now U.S. Pat. No. 7,192,752, is also a continuation in part of U.S. patent application Ser. No. 10/705,447, now U.S. Pat. No. 7,470,533, filed on Nov. 10, 2003, entitled "Impedance Based Devices and Methods for Use in Assays" which claims priority to U.S. provisional patent application Ser. No. 60/397,749, filed on Jul. 20, 2002; U.S. provisional patent application Ser. No. 60/435,400, filed on Dec. 20, 2002; U.S. provisional patent application Ser. No. 60/469,572, filed on May 9, 2003; and PCT patent application serial number PCT/US03/22557, filed on Jul. 18, 2003. All of the applications referred to in this paragraph are incorporated by reference in their entireties herein.

Parent U.S. patent application Ser. No. 11/055,639, now U.S. Pat. No. 7,560,269 also claims priority to U.S. provisional patent application Ser. No. 60/542,927 filed on Feb. 9, 2004; U.S. provisional patent application Ser. No. 60/548,713, filed on Feb. 27, 2004, and U.S. provisional patent application Ser. No. 60/614,601, filed on Sep. 29, 2004. All of the applications referred to in this paragraph are incorporated by reference in their entireties herein.

Parent U.S. patent application Ser. No. 11/197,994, now U.S. Pat. No. 7,468,255 also claims priority to U.S. provisional patent application Ser. No. 60/598,608, filed on Aug. 4, 2004, U.S. provisional patent application Ser. No. 60/630, 131, filed on Nov. 22, 2004, U.S. provisional patent application Ser. No. 60/689,422, filed on Jun. 10, 2005, U.S. provisional patent application Ser. No. 60/598,609, filed on Aug. 4, 2004, U.S. provisional patent application Ser. No. 60/613,749, filed on Sep. 27, 2004, U.S. provisional patent application Ser. No. 60/647,189, filed on Jan. 26, 2005, U.S. provisional patent application Ser. No. 60/647,075, filed on Jan. 26, 2005, U.S. provisional patent application Ser. No. 60/660,829, filed on Mar. 10, 2005, and U.S. provisional patent application Ser. No. 60/660,898, filed on Mar. 10, 2005. All of the applications referred to in this paragraph are incorporated by reference in their entireties herein.

TECHNICAL FIELD

This invention relates to the field of cell-based assays and more specifically to devices, methods and systems for performing extracellular recording of cells, such as cardiomyocytes, alone or in parallel with impedance monitoring.

BACKGROUND OF THE INVENTION

A. Electronic Analysis of Cells

Bioelectronics is a progressing interdisciplinary research field that involves the integration of biomaterials with electronic devices. Bioelectronics methods have been used for analyzing cells and assaying biological molecules and cells. In one type of application, cells are cultured on microelectrodes and cell-electrode impedance is measured and determined to monitor cellular changes.

In PCT Application No. PCT/US03/22557, titled "IMPEDANCE BASED DEVICES AND METHODS FOR USE IN ASSAYS", filed on Jul. 18, 2003, a device for detecting cells and/or molecules on an electrode surface is disclosed. The device detects cells and/or molecules through measurement of impedance changes resulting from the attachment or binding of cells and/or molecules to the electrode surfaces. A number of embodiments of the device are disclosed, together with the apparatuses, and systems for using such devices to perform certain cell based assays.

B. Dynamic Monitoring of Cardiomyocyte Viability, Morphology and Beating In Vitro To bring a new drug to the market it can take anywhere between 8 to 16 years, and average cost of developing a drug is now around $500 m-$800 m with the cost expected to hit the $1 bn mark within the next four years. Cardiotoxicity has been cited as the reason for 30 percent of all failed drug compounds during development and is a major cause of compound attrition. The late detection of cardiotoxic side effects caused by pharmacological compounds can impede drug discovery and development projects, and consequently increase their cost. Testing for the potential cardiotoxic side effects of compounds at an early stage of drug development has therefore been the goal of many pharmaceutical and biotechnology companies. Cardiotoxicity itself can entail a number of short-term and long term cellular events including directly affecting the beating rate of cardiomyocytes, viability of cardiomyocytes and morphology of cardiomyocytes as would occur in hypertrophy. The core of the current issue in pharmacological safety assessment and drug development is the lack of a reliable screening methodology capable of monitoring potential drug-mediated cardiotoxicity and distinguishing between different modes of cardiotoxicity. What is urgently needed in the field is a good cell-based model system as well as a monitoring system with a physiological and functional readout that can provide incisive information regarding potential cardiotoxic side effects of drugs.

1. Cell-Based Model System for Studying Cardiac Function

Traditionally, the drug discovery industry has undertaken two different approaches for toxicological assessment of drug candidate leads in cardiac function. The first approach involves isolation of cardiomyocytes directly from a mammalian species such as rats and dogs followed by electrophysiological and viability studies on the isolated cardiomyocytes. This approach is extremely labor-intensive, time consuming and costly and at the same time not very amenable to the high throughput demands of pharmaceutical industry.

An alternative method for prediction of cardiotoxicity of drug candidate leads early in the drug development process has involved utilizing cell-based assay models which heterologously express specific ion channels such as hERG channels or voltage-gated calcium channels. These cardiac ion channels have been envisioned as possible molecular targets through which drugs could induce cardiotoxicity. These cell-based systems allow the assessment of drug-channel interaction by monitoring the effect of the drug on the currents produced by the different channels in cultured cells using a technique known as 'patch clamping', which isolates regions of the cell membrane containing channel proteins and measures changes in electrical potential difference. Use of this method in high throughput requires automation of patch clamping in array format, which even though is available in last several years but is not yet widespread. The other issue with this approach is that cardiac toxicity may occur by other mechanisms which can easily be missed by this type of targeted approach. An alternative to the in vitro ion-channel recording assays as well as the labor-intensive isolation of primary tissue is the differentiation of embryonic stem (ES) cells into cardiomyocytes as a starting material for functional assays.

The utility of ES cells as a treatment for various chronic diseases has received much attention in recent years. Mammalian ES cells are self renewing cells derived from the inner cell mass of a blastocyst stage embryo which can be differentiated into multiple different cell types. It has been demonstrated that the mouse ES cells as well as human ES cells can be differentiated into cardiomyocytes which retain the ability to beat in culture. The differentiation of ES cells first involves an intermediate in vitro developmental stage in which ES cells form compact cell structures known as embryoid bodies. These embryoid bodies can induce the developmental program of ES cell differentiation into multiple cell types including cardiomyocytes which are distinguished in culture by their ability to undergo spontaneous beating. These ES derived in vitro differentiated cardiomyocytes recapitulates the normal development of cardiomyocytes as evidenced by the stage-specific expression of cardiomyocyte specific genes. All the known transcription factors, ion channels and structural proteins that are part of normal heart development and function in vivo are also expressed in ES-derived cardiomyocyte.

Because ES cells are self renewing cells in culture they can serve as an excellent source for continuous production of cardiomyocytes. Therefore, these cardiomyocytes which behave in every way like normal cardiomyocytes isolated from the heart tissue itself addresses the ever important supply problem and for the first time allows for assessment of cardiac function and its modulation by lead candidate drugs and compounds in relatively large scale in both viability assays, assessment of morphology and in monitoring the beating function of cardiomyocytes. Furthermore, because the technology exists to selectively knockout or express trans-genes in ES cells, it provides an excellent model system to study the role of certain genes in cardiac development and function without having to be concerned about adverse affects on overall embryonic development in transgenic animals. The ability to express transgenes in ES cells has been utilized as a way to enrich for preparation of cardiomyocytes that are 100% pure. For example, the gene encoding GFP has been cloned downstream of a cardiac-specific promoter and then introduced into ES cells. Embryoid cells which ultimately differentiate into cardiomyocytes will therefore express the GFP transgenes and these cells can be easily isolated by cell sorting techniques and therefore an enriched cardiomyocyte population can be obtained.

2. Technologies Used for Assessment of Cardiomyocyte Function In Vitro

Technologies designed to assess cardiomyocyte behavior and function and the effect of drugs and other manipulations in vitro can be divided into two different approaches. One approach involves long term assessment of cardiomyocyte viability for example in response to certain compounds. Such assays are typically end point assays designed to measure a cellular component such as ATP which correlates with the degree of viability of the cells. The other approach involves studying short term effect of drugs and compounds on beating function of cardiomyocytes. High throughput techniques for short term functional characterization of ion channels and other targets in cardiomyocytes has been rather challenging and limited. The systems such as automatic patch clamp instrumentation that are available can monitor a single cardiomyocyte at a time and with very limited throughput.

Accordingly, while there exists different approaches to assess cardiotoxicity of various compounds, each suffers from one or more drawbacks. Thus, there remains a need to develop improved devices and methods that have high throughput capabilities and improved accuracy and reliability with respect to measurements and correlation with cell phenotype.

SUMMARY OF THE INVENTION

The present invention discloses devices, systems and methods for performing extracellular recording of excitable cells, such as cardiomyocytes, in vitro. Specifically, the devices and methods provide improved characterization of excitable cells in response to compound administration to assess cardiotoxic effects, while increasing efficiency of throughput for potential drug candidates. The invention further provides improved characterization of cells during differentiation processes related to development of cardiomyocytes.

It is an object of the invention to provide extracellular recording configurations, which permit reproducible sampling across larger cell populations compared to traditional approaches. It is another object of the invention to provide cell-free zones for positioning a reference electrode to prevent its direct interaction with a cell population loaded onto the device. It is another object of the invention to provide a combined device capable of both performing extracellular recording measurements and impedance monitoring, which may be selectively activated for measurement and thus provide a multi-faceted system for assessing or characterizing excitable cells.

In one aspect of the present invention a device for performing extracellular recording of cells, such as excitable cells, cardiomyocytes, and cardiomyocyte precursor cells is provided. An exemplary device includes a) a nonconductive substrate forming or provided as a base of one or more wells; b) a recording electrode positioned on the substrate within the well, wherein the recording electrode is accessible to cells when a cell sample is added to the device; and c) a reference electrode positioned within the well in a cell-free zone, the cell-free zone characterized as free from contact with cells when the cell sample is added to the device, thereby preventing contact between cells and the reference electrode. The cell-free zone prevents direct contact between cells from a cell sample and the reference electrode. In some embodiments, the recording electrode has a diameter from about 10 um to about 200 um. In other embodiments, the recording electrode comprises an electrode structure comprising a plurality of electrode elements In some embodiments, the cell-free zone is physically defined by the presence of a barrier, such as a wall, through which cells do not pass. In certain embodiments, the barrier could be in the form of a removable blockage material which is placed directed on the cell-free zone when cells are added to the well and which can be removed after cells have settled along the bottom of the well. Thus, the blocking structure may be in part removable. In other embodiments, the cell free zone is provided as a platform or surface positioned above the base substrate. In other embodiments, the cell free zone is positioned along an angled wall, which is angled upward from the bottom of the well. In other embodiments, the cell-free zone is positioned above the substrate and within the volume of the well such that an external electrode extends downward into sample media, optionally from a lid or cap for the well.

In some embodiments the extracellular recording electrode is a unitary or unbranched electrode and may be of a simple geometry such as a circle, a square and the like. In other embodiments, the extracellular recording electrode has a branched configuration, which may permit extracellular recording over a larger cell population. Increasing the measured cell population for extracellular recording may increase measurement accuracy or reproducibility of the recorded signals. In one exemplary embodiment, a device for performing extracellular recordings of excitable cells in vitro includes a) a nonconductive substrate; b) one or more wells on the substrate; c) one or more electrode structures fabricated on the substrate, each electrode structure associated with one of the one or more wells; and d) one or more reference electrodes external to the substrate, each of which can be inserted into one of the one or more wells, wherein for each of the one or wells, the corresponding electrode structures and reference electrodes form an electrode pair. In further embodiments the substrate has a surface suitable for attachment of excitable cells, wherein the attachment of excitable cells on the substrate can result in a detectable extracellular recording potential between each electrode pair. In a further embodiment, which is also a preferred embodiment, each electrode structure comprises multiple electrode elements. In another preferred embodiment, each electrode structure comprises multiple electrode elements, forming half of an interdigitated electrode array. In another preferred embodiment, each electrode structure comprises multiple electrode elements which have different electrode element shapes, including rectangular shape, or sinusoidal shape, or circle-on-line shape.

In another preferred embodiment of the device for performing extracellular recording, each electrode structure occupies a substantial percentage of surface area of the well that the electrode structure is associated with. In some preferred embodiments, percentage of surface area of the well at the bottom being occupied by the electrode structures is more than 1%. Preferably, percentage of surface area of the well at the bottom being occupied by the electrode structures is more than 5%. Preferably, percentage of surface area of the well at the bottom being occupied by the electrode structures is more than 10%. More preferably, the percentage of surface area of the well at the bottom being occupied by the electrode structures is more than 20%. More preferably, the percentage of surface area of the well at the bottom being occupied by the electrode structures is more than 30%. More preferably, the percentage of surface area of the well at the bottom being occupied by the electrode structures is more than 50%. More preferably, the percentage of surface area of the well at the bottom being occupied by the electrode structures is more than 70%. More preferably, the percentage of surface area of the well at the bottom being occupied by the electrode structures is more than 85%.

In another aspect of the present invention, a method of performing extracellular recording of excitable cells includes, providing a device of the present invention, adding excitable cells to the wells; providing an extra-cellular-recording amplifier that can measure and record voltage signals at microvolt levels, connecting electrodes on the devices to the extra-cellular-recording amplifier; monitoring and recording extracellular potentials at the electrodes of the devices. Preferably, the method further comprises analyzing recorded extracellular potential waveforms. More preferably, the method further comprises adding a compound to the well, measuring and recording extracellular potentials prior to and after the compound addition; and analyzing extracellular potential waveforms.

In still another aspect of the present invention, a device allowing for parallel extracellular recording and cell impedance monitoring of a cell population is provided. The device includes a cell impedance monitoring means and an extracellular recording means operably coupled through a same substrate. In a further embodiment a switching means switches operation of the device between impedance monitoring and extracellular recording.

In still another aspect of the present invention, a device allowing for parallel extracellular recording and cell impedance measurement comprises a nonconductive substrate, having a surface suitable for attachment of excitable cells, one or more wells on the substrate; for each well, a pair of impedance measurement electrodes, wherein the attachment of excitable cells on the substrate can result in a detectable impedance change between the pair of impedance measurement electrodes; for each well, a pair of extra-cellular recording electrodes, wherein the attachment of excitable cells on the substrate can result in a detectable extra-cellular recording potentials between the pair of extra-cellular recording electrodes. Preferably, the pair of impedance measurement electrodes is located on the substrate. More preferably, for the pair of extra-cellular recording electrodes, one recording electrode is located on the substrate and another electrode is located external to the substrate. In other preferred embodiments, the reference electrode may be isolated from cells by positioning the reference electrode at a cell-free zone, such that it is a cell-free electrode. The reference electrode may or may not be located on the substrate. The device may also include or be operably connected to a switching means to switch from an impedance mode to an extracellular recording mode.

In another aspect of the invention, a device allowing for parallel extracellular recording and cell impedance measurement includes a nonconductive substrate forming or provided as a base of one or more wells; at least two impedance electrodes capable of monitoring impedance of the cells, the at least two impedance electrodes positioned within a well and on the nonconductive substrate; and a reference electrode, wherein a first impedance electrode from the at least two impedance electrodes is electrically coupled to the reference electrode for performing an extracellular recording measurement at the first impedance electrode.

In still another aspect of the present invention, a method for parallel measurement of cell-substrate impedance and extra-cellular potentials includes a) providing a device allowing for parallel extracellular recording and cell impedance measurement; b) adding excitable cells to the wells of the device; c) providing an impedance analyzer; d) providing an extracellular potential amplifier; e) connecting impedance-measurement electrodes of the devices to the impedance analyzer; f) connecting extra-cellular recording electrodes of the devices to the extra-cellular potential amplifier; g) performing parallel measurement of cell-substrate impedance and extracellular potentials. Preferably, the method further comprises adding compounds to the cells and monitoring cell-substrate impedance and extracellular potentials prior to and after compound addition. Preferably, the method further comprises analyzing measured time dependent impedance responses. Still preferably, the method further comprising analyzing extracellular-recording wave forms.

In present invention, we describe label-free methods for monitoring cardiomyocytes in vitro. In one aspect of the present invention, extracellular-recording measurement, or parallel impedance and extracellular recording measurement of cardiomyocytes on microelectrodes is used to non-invasively monitor cardiac cell viability in vitro in long term experiments. This method will allow the continuous monitoring of cardiomyocyte viability overtime and can monitor the interaction of compounds which ultimately result in promoting loss of cardiomyocyte viability.

In another aspect of the present invention, extracellular-recording measurement or parallel impedance and extracellular recording measurement of cardiomyocytes on microelectrodes is used to non-invasively monitor cardiomyocyte beating in vitro. The system is capable of continuously monitoring the excitation-contraction coupling, otherwise know as beating, of cardiomyocytes in a relatively high-throughput manner using either extracellular-recording measurement or parallel impedance and extracellular recording measurement. It can be used for pharmacological safety assessment, screening for novel compounds which modulate cardiomyocyte function in a specific manner and assessment of genes involved in cardiac function.

In another aspect of the present invention, extracellular recording measurement or parallel impedance and extracellular recording measurement can be used to monitor both short term beating whilst impedance measurement can be used to monitor long term viability status of cardiomyocytes in the same well. The ability to monitor both cardiomyocyte beating in conjunction with viability for the same population of cardiomyocytes over time would be an added advantage. Certain manipulations such as drug treatment may not manifest their effect on cardiomyocyte beating and/or viability until at a later time period. Therefore, the time resolution as well as the capabilities of extracellular recording measurements together with impedance measurements of the system of the present invention can be used to monitor cardiomyocyte beating and viability over time.

In another aspect of the present invention, impedance readout can be used to monitor the morphological or differentiative behavior of cardiomyocytes in vitro. Certain treatments can induce changes in morphological behavior of cardiomyocytes, such as inducing hypertrophy which is associated with cardiomyocyte elongation and expansion. Because impedance monitoring can detect changes in cell morphology, it can be used to for detection of hypertrophy in cardiomyocytes.

In another aspect of the present invention, direct optical monitoring of cardiomyocytes is used to quantify and measure the beating of cardiomyocytes. Still, in another aspect of the present invention, extracellular recordings (i.e. measurement of electrical potentials of extracellular recording electrodes when cardiomyocytes are attached to the electrode surfaces) are used to quantify and measure the beating of cardiomyocytes. Still, in another aspect of the present invention, a physical method which can be used to monitor cell-substrate interaction is used to quantify and monitor beating of cardiomyocytes.

In another aspect of the present invention, the methods include real-time impedance monitoring and/or extracellular recording of cardiomyocyte in vitro. This invention will be able to monitor viability of cardiomyocytes, the field potential of cardiomyocytes, or the excitation-contraction coupling or beating and morphological and differentiative aspects of cardiomyocytes in a label-free manner and real-time manner. Furthermore, the invention will be able to monitor cardiotoxicity and the effect of compounds and drugs for safety pharmacology purposes and can also serve as a screen for agents which can modulate cardiomyocyte function. This system can be used in conjunction with ES derived cardiomyocytes, adult stem-cell derived cardiomyocytes as well as primary cardiomyocytes to study the role of different genes and proteins in cardiac function and development.

The system of the present invention having the capability of parallel impedance-based monitoring as well as extracellular recording based monitoring of cardiomyocytes fills a major technological gap in monitoring cardiomyocytes in vitro. At present to our knowledge there are only a few technologies that can monitor cardiomyocyte population function in vitro, especially with regards to cardiotoxicity and are limited in their throughput. In addition to functional monitoring of cardiomyocyte beating the current invention offers several other major benefits which are worth discussing. Among these include the impedance system described here can monitor cardiomyocytes for short durations, milliseconds to minutes and long durations, several hours to days. Therefore, both short term and long term effects of drugs not only on cardiomyocyte beating, but viability and changes in morphology and adhesion can also be assessed. This feature is especially important because certain compounds such as β-2 adrenergic receptor agonists, well known and characterized modulators of heart function in vivo and in vitro, can induce long term hypertrophic responses in cardiomyocytes, which is associated with elongated morphology of the cells. In addition, the systems of the present invention can also record cardiomyocyte action potentials or field potentials, allowing detailed electrophysiological analysis and assessment of cardiomyocytes for relatively short duration at a time.

The method of the present invention is to devise a label-free cell-based assay system for continuous monitoring of cardiomyocyte viability, the rhythmic beating of cardiomyocytes and cardiomyocyte morphology and differentiation and to screen for pharmacological agents which may modulate these processes and induce cardiotoxicity. In one aspect, viability is monitored based on long term impedance monitoring of cardiomyocytes seeded in microelectronic plates (E-PLATES), and in parallel, the field potential generated by the excitation of the cardiomyocytes or other excitable cells is monitored using the extracellular potential recording electrodes associated with the wells of the E-PLATES. Viable cells will continue to generate impedance signal and any changes in viability, especially due to cytotoxic or cardiotoxic drugs will be reflected by changes in impedance. In one respect, the method includes providing a device for measuring cell-substrate impedance and extracellular potentials operably connected to an impedance analyzer and extracellular recording potential amplifier, wherein the device includes at least one well optionally coated with fibronectin or other appropriate extracellular matrix proteins (e.g. gelatin) to expedite attachment; adding cells to the at least one well, where the cells can be mouse or human or other mammalian ES cells or adult stem cells destined to differentiate into cardiomyocytes or primary cardiomyocytes isolated directly from the heart of an experimental system including mice, rats, rabbits or dog; monitoring impedance of the at least one well over a period of time and optionally determining cell index from impedance values; and monitoring the extracellular potentials using recording electrodes associated with the wells of the E-PLATES.

In another aspect, the method includes providing a device for measuring cell-substrate impedance and for performing extracellular recording operably connected to an impedance analyzer and extracellular recording potential amplifier, wherein the device includes at least two wells optionally coated with fibronectin (or other extracellular matrix proteins such as gelatin) to expedite attachment; adding cells to the at least two wells, where the cells can be mouse or human or other mammalian ES cells or adult stem cells destined to differentiate into cardiomyocytes or primary cardiomyocytes isolated directly from the heart of an experimental system including mice, rats, rabbits or dog; monitoring impedance and monitoring extracellular potentials of the at least two wells over a period of time. Treating at least one well with an agent; where the agent could include but is not limited to a compound, peptide, protein, antibody, siRNA, shRNA, lipid or any combination of thereof and the other well is treated with an appropriate control; continue monitoring of control and treated well over a period of time preoptimized for the experiment of interest; concluding that the factor may affect cell viability if the impedance of the treated well is significantly different than the impedance of the treated well and/or concluding that the factor may affect cell excitation if the extracellular potential of the treated well is significantly different from that of the treated well.

Dynamic monitoring of cardiomyocyte beating is based on quantification in real time of the rhythmic changes in cardiomyocyte morphology as a result of the excitation contraction coupling of the electrically excitable cardiomyocytes growing on microelectrodes' surface in ACEA E-PLATES. The quantification of the rhythmic changes in cardiomyocyte morphology is achieved via the fast (down to milliseconds level, for example, at 40 milli-second, 30 milli-second, 20 milli-second, 10 milli-second or 5 millisecond time resolutions) and continuous measurement of electrode impedance. The method essentially provides a cellular cardio-gram which can provide incisive information about the status of cardiomyocytes especially upon treatment with pharmacological agents. In addition, the method allows for parallel measurement of extracellular potentials of beating cardiomyocytes, providing important electrophysiological property information of the cells. The method includes providing a device for measuring cell-substrate impedance and for monitoring extracellular potential operably connected to an impedance analyzer and an extracellular potential amplifier, wherein the device includes at least one well optionally coated with fibronectin (or other suitable extracellular matrix proteins) to expedite attachment; adding cells to the at least one well, where the cells can be mouse or human or other mammalian ES cells or adult stem cells destined to differentiate into cardiomyocytes or primary cardiomyocytes isolated directly from the heart of an experimental system including mice, rats, rabbits or dog; monitoring impedance of the at least one well at time intervals over a period of time and optionally determining cell indices from impedance values and monitoring extracellular potentials from the at least one well for a time period (for example, 10 seconds) at certain time intervals (for example, every 10 minutes); optionally calculating average rate of beats per unit time, average amplitude intensity in a unit time as well as the average length of time between the beats.

In another aspect, the present invention is directed to method to screen for potential agents that modulate ES-derived cardiomyocyte beating, adult stem cell-derived cardiomyocyte beating or primary cardiomyocyte beating by monitoring and measuring the excitation-contraction coupling of cardiomyocyte and its modulation by the agent. The agent may include but is not limited to compounds, drugs, peptides, proteins, antibodies, siRNA, shRNA, miRNA, cDNA, lipids and any combination thereof. The method includes providing a device for measuring cell-substrate impedance and for monitoring extracellular potentials operably connected to an impedance analyzer and to an extracellular potential amplifier, wherein the device includes at least two wells; adding ES cells, adult stem-cell derived cardiomyocytes or primary cardiomyocytes to at least two wells; monitoring impedance of the at least two wells at different or similar time intervals over a period of time and optionally determining cell indices from impedance values and monitoring and recording extracellular potentials of the at least two wells for a time window at time intervals over a period of time; generating an impedance-based curve or optionally a cell index curve for each of the at least one known factor and the control; comparing the impedance-based curves or optionally the cell index curves between the at least one known biologically active agent well and the control well; the impedance-based curves could be direct measurement of cardiomyocyte excitation-contraction coupling and if significantly different, concluding that the biologically active agent modulates cardiomyocyte function, and/or comparing the extracellular potential waveforms from the active agent well and the control well and, if significantly different, concluding that the biologically active agent modulates the excitation property of the cardiomyocytes. Optionally, impedance-based curves or optionally cell index curves are used to calculate average rate of beats of cardiomyocytes per unit time, average amplitude intensity in a unit time as well as the average length of time between the beats, comparison of these optionally derived parameters is made between the at least one known biologically active agent well and the control well, and if significant differences exist, one may optionally conclude that the biologically active agents modulate cardiomyocyte functions.

It is well established that certain pharmacological treatments and disease conditions can result in cardiac hypertrophy or atrophy culminating in changes in the morphology of cardiomyocyte. Cell substrate impedance can be used to precisely measure and quantify these changes in cell morphology and shape. Certain treatments can also affect the differentiative process of ES cells to cardiomyocytes which may involve specific morphological and adhesive changes. In another aspect, the present invention is directed to method to screen for potential agents that may modulate the morphology of ES-derived cardiomyocyte, adult stem cell-derived cardiomyocyte or primary cardiomyocyte or its differentiation. The agent may include but is not limited to compounds, drugs, peptides, proteins, antibodies, siRNA, shRNA, miRNA, cDNA, lipids and any combination thereof. The method includes providing a device for measuring cell-substrate impedance operably connected to an impedance analyzer, wherein the device includes at least two wells; adding ES cells, adult stem-cell derived cardiomyocytes or primary cardiomyocytes to at least two wells; monitoring impedance of the at least two wells at different or similar time intervals over a period of time and optionally determining cell indices from impedance values; generating an impedance-based curve or optionally a cell index curve for each of the at least one known factor and the control; comparing the impedance-based curves or optionally the cell index curves between the at least one known biologically active agent well and the control well; the impedance-based curves could be direct measurement of changes in cell morphology and if significantly different, concluding that the biologically active agent modulates cardiomyocyte function. Preferably, the method further comprises providing the device of the present invention operably connected to an extracellular potential amplifier, monitoring extracellular potentials of cells from one biologically active agent well and one control well. Optionally, impedance-based curves or optionally cell index curves are used to calculate the compound dose-dependent changes in cardiomyocyte morphology and generate an EC-50 value for the potency of the compound. In addition, extracellular recording permits comparisons with cells at various developmental stages to assess development.

In another aspect, the present invention is directed to method to establish an assay to assess the effect of gene knockout or transgene expression in ES cells differentiated to cardiomyocytes and functionally monitored by the system of the present invention. The method includes providing a device for measuring cell-substrate impedance and for monitoring extracellular potential operably connected to an impedance analyzer and extracellular potential amplifier, wherein the device includes at least two wells; adding wildtype ES cells as control to at least 1 well and ES cells with a gene knockout or a transgene in at least 1 other well; monitoring impedance of the at least two wells at time intervals over a period of time and optionally determining cell indices from impedance values; comparing the impedance-based curves or optionally the cell index curves between the control well and the well containing the ES cells harboring a kockout of a specific gene or expressing a specific transgene; and if significantly different, concluding that the gene knockout or the transgene can affect either cardiomyocyte viability, morphology from ES cells or cardiomyocyte function as monitored by observing the excitation-contraction coupling, and alternatively, monitoring and recording extracellular potentials from the at least two wells for a time period, comparing the extracellular potential waveforms between the control well and the well containing the ES cells harboring a kockout of a specific gene or expressing a specific transgene; and if significantly different, concluding that the gene knockout or the transgene can affect cardiomyocyte electrophysiological property of the cardiomyocytes.

In another aspect of the present invention, direct optical monitoring of cardiomyocytes is used to quantify and measure the beating of cardiomyocytes. The method includes providing a device for optically monitoring cells and monitoring cell morphology operably connected to an optical measurement system, where the device includes at least two wells optionally coated with fibronectin (or other suitable extracellular matrix proteins) to expedite attachment; adding cells to the at least two wells, where the cells can be mouse or human or other mammalian ES cells destined to differentiate into cardiomyocytes or primary cardiomyocytes isolated directly from the heart of an experimental system including mice, rats, rabbits or dog; optically monitoring the cells of at least two wells at time intervals over a period of time via the optical measurement system; optionally calculating average rate of beats per unit time, average amplitude intensity in a unit time as well as the average length of time between the beats. The device for such optical measurement of cells may include microtiter plates. The optical system may include optical magnification instrument such as microscope, optical CCD camera, optical-signal processing algorithm to quantify cell beating and to derive cell-beating parameters (such as calculating average rate of beats per unit time, average amplitude intensity in a unit time as well as the average length of time between the beats) based on cell morphology images.

In another aspect of the present invention, extracellular recordings (i.e. measurement of electrical potentials of extracellular recording electrodes when cardiomyocytes are attached to the electrode surfaces) are used to quantify and measure the beating of cardiomyocytes. The method includes providing a device with microelectrodes for extracellular recording of multiple cells operably connected to an extracellular potential recording system, where the device includes at least two wells optionally coated with fibronectin (or other extracellular matrix proteins) to expedite attachment; adding cells to the at least two wells, where the cells can be mouse or human or other mammalian ES cells destined to differentiate into cardiomyocytes or primary cardiomyocytes isolated directly from the heart of an experimental system including mice, rats, rabbits or dog; performing extracellular recording of the cells of at least two wells via the extracellular recording system; optionally calculating average rate of beats per unit time, average amplitude intensity in a unit time as well as the average length of time between the beats. The device for such extracellular recording system includes microelectrode arrays or structures inside wells of microtiter plates. The microelectrode array may comprise two electrode structures having the substantially same surface area and may be located along the majority of the surface of the wells. The extracellular recording system may include electronic measurement circuits capable of recording small extracellular potentials induced on microelectrodes, where cells are cultured. The signals from the extracellular recording can be used to derive the average rate of beats of cardiomyocytes per unit time, average amplitude intensity in a unit time as well as the average length of time between the beats, or other electrophysiologically-associated parameters.

Still, in another aspect of the present invention, a physical method which can be used to monitor cell-substrate interaction is used to quantify and monitor beating of cardiomyocytes. The method includes providing a device for physically monitoring cells and monitoring cell morphology operably connected to a physical measurement system, where the device includes at least two wells optionally coated with fibronectin (or other extracellular matrix proteins) to expedite attachment; adding cells to the at least two wells, where the cells can be mouse or human or other mammalian ES cells destined to differentiate into cardiomyocytes or primary cardiomyocytes isolated directly from the heart of an experimental system including mice, rats, rabbits or dog; optically monitoring the cells of at least two wells at time intervals over a period of time via the physical measurement system; optionally calculating average rate of beats per unit time, average amplitude intensity in a unit time as well as the average length of time between the beats. The device for such physical measurement of cells shall have such property that the interaction between cells and substrate surfaces can be monitored. Depending which physical method is used for monitoring cell-substrate interaction, different devices may be used. For example, the device can be an optical sensor, which can be used to detect and measure biological reactions. One example of optical sensor is resonant waveguide, which consists of a substrate with an optical grating and a coating with a high refraction index. This grating forms an optical waveguide, a tiny channel through which a specific wavelength of light propagates. Only this specific wavelength that is resonant with the waveguide grating structure is strongly reflected. In this case, the physical measurement system can detect changes in refractive index upon cell-substrate interaction events or upon intracellular events. Examples of cell-substrate interaction events or intracellular events may include those taking place in cultured cells stimulated by a compound treatment.

BRIEF DESCRIPTION OF THE DRAWINGS

FIG. 5 shows the detection of cardiomyocyte beating using the ACEA RT-CES system at different time periods along the growth and differentiative curve of ES-derived cardiomyocytes seeded in ACEA E-PLATES. Each well of the E-PLATE comprises an impedance measurement electrode array, comprising two circle-on-line electrode structures. FIGS. 5A, 5B and 5C show the cell index curves at time resolution of 40 milli-seconds for time points at 24, 48 and 72 hrs after cell seeding, respectively.

FIG. 7 shows the detection of cardiomyocyte beating using the ACEA RT-CES system for the mouse ES-derived cardiomyocytes treated with 4.4 uM sotalol.

FIG. 9S shows the 0.13% DMSO control, indicating that DMSO at such a concentration does not produce a significant change on the beating of the cardiomyocytes. Note that one second displayed in FIGS. 9A-9S is equivalent to 40 milli-seconds for real time measurement. The time resolution of the measurement for FIGS. 9A-9S is 40 milli-seconds.

FIG. 18 shows the extracellular field potential (FP) recorded for mouse ES-derived cardiomyocytes on day 2 and day 3 after cell plating using electrode array shown in FIG. 17.

FIG. 22 shows extra-cellular field potentials recorded for mouse stem-cell derived cardiomyocytes obtained using a device of the present invention, where the recording electrode is a circle-on-line electrode structure and the reference electrode is a gold wire electrode that is introduced into the well after cell seeding. FIGS. 22A, 22B, 22C and 22D shows the recorded waveforms before treatment, ~18 seconds, ~3 minutes and 5.5 minutes after treatment with E4031, respectively.

FIGS. 23A, 23B, 23C, 23 D and 23E show the recorded waveforms before treatment, 10 seconds, 50 seconds, 3 minutes and 9 minutes after treatment with 3 uM Quinidine, respectively.

FIG. 24 shows parallel impedance monitoring of beating of mouse stem-cell derived cardiomyocytes obtained using a device of the present invention, where the impedance is monitored using an electrode array comprising two electrode structures each of which comprises multiple circle-on-line electrode elements. FIGS. 24A, 24B, 24C, and 24 D show the recorded impedance beating signals before treatment, 1.5 minute, ~3 minute and ~11 minute after treatment with 3 uM Quinidine, respectively.

DETAILED DESCRIPTION OF THE INVENTION

A. Definitions

Figure 1:
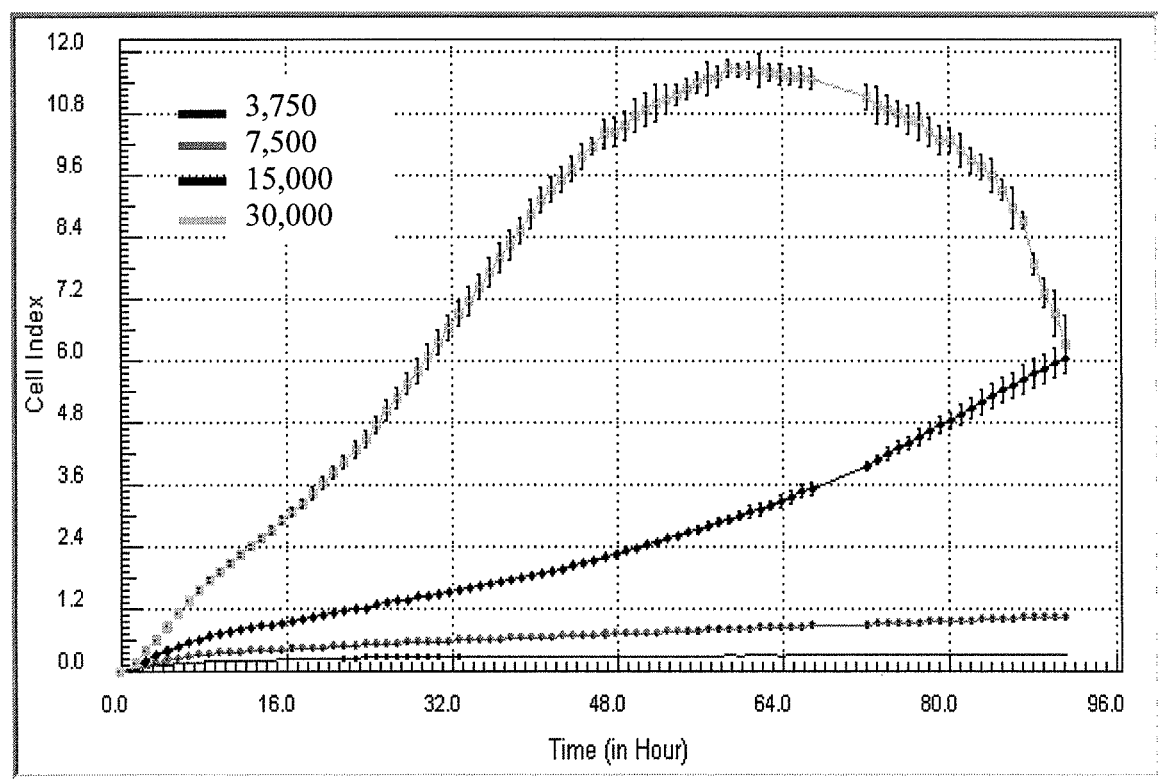
FIG. 1 shows the cell index curves measured on RT-CES system for 4 different seeding densities (3750, 7500, 15,000 and 30,000 cells per well) of mouse ES-derived cardiomyocytes. Cell index is a dimensionless parameter derived in RT-CES system.

For clarity of disclosure, and not by way of limitation, the detailed description of the invention is divided into the subsections that follow. Further, unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in the patents, applications, published applications and other publications that are herein incorporated by reference, the definition set forth in this section prevails over the definition that is incorporated herein by reference.

As used herein, "biocompatible membrane" means a membrane that does not have deleterious effects on cells, including the viability, attachment, spreading, motility, growth, cell division or cell beating.

A "biomolecular coating" or a "biological molecule coating" is a coating on a surface that comprises a molecule that is a naturally occurring biological molecule or biochemical, or a biochemical derived from or based on one or more naturally occurring biomolecules or biochemicals. For example, a biological molecule coating can include an extracellular matrix component (e.g., fibronectin, collagens), or a derivative thereof, or can comprise a biochemical such as polylysine or polyornithine, which are polymeric molecules based on the naturally occurring biochemicals lysine and ornithine. Polymeric molecules based on naturally occurring biochemicals such as amino acids can use isomers or enantiomers of the naturally-occurring biochemicals.

A "cell-free zone" is a region of the device where cells, when added to the device, are not physically present. The "cell-free zone" may be a region on the substrate, which is blocked from cell access. The "cell-free zone" may be a spatial position free from contact with the substrate such as a spatial position above a substrate base and within the volume of the well. The "cell-free zone" should permit the passage of electrical current such as through a conductive medium. For example, a reference electrode or external electrode may be suspended in a cell-free zone, free from contact with the substrate, yet remain electrically coupled to an extracellular recording electrode disposed on the substrate.

A "cell-free electrode" is an electrode that is free from contact with all cells present in the device.

The term "free from contact" or "free from direct contact" refers to two individuals, whether cells or apparatus components that lack contacting surfaces. A cell suspended in medium, in which only the medium contacts an electrode is "free from contact" or "free from direct contact" with the electrode.

An "organic compound coating" is a coating on a surface that includes an organic compound. For example an organic compound may include a natural ligand or an agonist or an antagonist for a cell surface receptor.

An "extracellular matrix component" is a molecule that occurs in the extracellular matrix of an animal. It can be a component of an extracellular matrix from any species and from any tissue type. Nonlimiting examples of extracellular matrix components include laminins, collagens fibronectins, other glycoproteins, peptides, glycosaminoglycans, proteoglycans, etc. Extracellular matrix components can also include growth factors.

An "electrode" is a structure having a high electrical conductivity, that is, an electrical conductivity much higher than the electrical conductivity of the surrounding materials, which in the present invention are typically nonconductive. An "extracellular recording electrode" or "recording electrode" or "ECR electrode" is such a structure used to detect electrical signal corresponding to extracellular field potential of the cell or cell population. For instance, a "recording electrode" may be used to monitor the extracellular field potential of a cardiomyocyte during the generation of membrane action potentials. A "reference electrode" is the complementary structure used to complete the electrical circuit during extracellular recording. An "impedance electrode" or an "impedance measurement electrode" or "impedance measurement electrode structure" is a structure, such as an electrode, used for impedance monitoring. An "impedance electrode" may also operate as an extracellular recording electrode and thus may provide both impedance monitoring and extracellular recording measurements, albeit at different time points.

As used herein, an "electrode structure" refers to a single electrode, particularly one with a complex structure (as, for example, a spiral electrode structure), or a collection of at least two electrode elements that are electrically connected together. All the electrode elements within an "electrode structure" are electrically connected.

As used herein, "electrode element" refers to a single structural feature of an electrode structure, such as, for example, a fingerlike or branched projection of an interdigitated electrode structure. An electrode structure may have a plurality of electrode elements.

As used herein, a "unitary electrode structure" refers to a single electrode that is unbranched. That is, a "unitary electrode structure" does not include a plurality of electrode elements. For example, an unitary electrode structure may be of a circle, a square or other geometry.

As used herein, an "electrode array" or "electrode structure unit" is two or more electrode structures that are constructed to have dimensions and spacing such that they can, when connected to a signal source, operate as a unit to generate an electrical field in the region of spaces around the electrode structures. Preferred electrode structure units of the present invention can measure impedance changes due to cell attachment to an electrode surface. Non-limiting examples of electrode structure units are interdigitated electrode structure units and concentric electrode structure units.

An "electrode bus" is a portion of an electrode that connects individual electrode elements or substructures. An electrode bus provides a common conduction path from individual electrode elements or individual electrode substructures to another electrical connection. In the devices of the present invention, an electrode bus can contact each electrode element of an electrode structure and provide an electrical connection path to electrical traces that lead to a connection pad.

"Electrode traces" or "electrically conductive traces" or "electrical traces", are electrically conductive paths that extend from electrodes or electrode elements or electrode structures toward one end or boundary of a device or apparatus for connecting the electrodes or electrode elements or electrode structures to an analyzer or amplifier, such as an impedance amplifier, a voltage amplifier and the like. Both impedance electrodes and extracellular recording electrodes may connect to an "electrode trace." The end or boundary of a device may correspond to the connection pads on the device or apparatus.

A "connection pad" is an area on an apparatus or a device of the present invention which is electrically connected to at least one electrode or all electrode elements within at least one electrode structure on an apparatus or a device and which can be operatively connected to external electrical circuits (e.g., an impedance measurement circuit or a signal source or an extracellular voltage signal amplifier). The electrical connection between a connection pad and an impedance measurement circuit, an extracellular recording circuit or a signal source can be direct or indirect, through any appropriate electrical conduction means such as leads or wires. Such electrical conduction means may also go through electrode or electrical conduction paths located on other regions of the apparatus or device.

"Interdigitated" means having projections coming one direction that interlace with projections coming from a different direction in the manner of the fingers of folded hands (with the caveat that interdigitated electrode elements preferably do not contact one another).

As used herein, a "high probability of contacting an electrode element" means that, if a cell is randomly positioned within the sensor area of a device or apparatus of the present invention, the probability of a cell (or particle) contacting an electrode element, calculated from the average diameter of a cell used on or in a device or apparatus of the present invention, the sizes of the electrode elements, and the size of the gaps between electrode elements, is greater than about 50%, more preferably greater than about 60%, yet more preferably greater than about 70%, and even more preferably greater than about 80%, greater than about 90%, or greater than about 95%.

As used herein, "at least two electrodes fabricated on the substrate" means that the at least two electrodes are fabricated or made or produced on the substrate. The at least two electrodes can be on the same side of the substrate or on the different side of the substrate. The substrate may have multiple layers, the at least two electrodes can be either on the same or on the different layers of the substrate.

As used herein, "at least two electrodes fabricated to a same plane of the substrate" means that, if the nonconducting substrate has multiple layers, the at least two electrodes are fabricated to the same layer of the substrate.

As used herein, "an electrode positioned on a different plane" refers to the positioning of an electrode, typically an external electrode or reference electrode, above, below or along a different surface angle than that which it is compared. An "electrode positioned on a different plane" may be parallel to that of the first.

As used herein, "the . . . electrodes (or electrode structures) have substantially the same surface area" means that the surface areas of the electrodes referred to are not substantially different from each other, so that the impedance change due to cell attachment or growth on any one of the electrodes (or electrode structures) referred to will contribute to the overall detectable change in impedance to a same or similar degree as the impedance change due to cell attachment or growth on any other of the electrodes (or electrode structures) referred to. In other words, where electrodes (or electrode structures) have substantially the same surface area, any one of the electrodes can contribute to overall change in impedance upon cell attachment or growth on the electrode. In most cases, the ratio of surface area between the largest electrode and the smallest electrode that have "substantially the same surface area" is less than 10. Preferably, the ratio of surface area between the largest electrode and the smallest electrode of an electrode array is less than 5, 4, 3, 2, 1.5, 1.2 or 1.1. More preferably, the at least two electrodes of an electrode structure have nearly identical or identical surface area.

As used herein, "the device has a surface suitable for cell attachment or growth" means that the electrode and/or non-electrode area of the apparatus has appropriate physical, chemical or biological properties such that cells of interest can viably attach on the surface and new cells can continue to attach, while the cell culture grows, on the surface of the apparatus. However, it is not necessary that the device, or the surface thereof, contain substances necessary for cell viability or growth. These necessary substances, e.g., nutrients or growth factors, can be supplied in a medium. Preferably, when a suspension of viable cardiomyocytes, neuron cells, muscle cells or other excitable cells or other adherent cells such as epithelial cells or endothelial cells is added to the "surface suitable for cell attachment" when at least 50% of the cells are adhering to the surface within twelve hours. More preferably, a surface that is suitable for cell attachment has surface properties so that at least 70% of the cells are adhering to the surface within twelve hours of plating (i.e., adding cells to the chamber or well that comprises the said device). Even more preferably, the surface properties of a surface that is suitable for cell attachment results in at least 90% of the cells adhering to the surface within twelve hours of plating. Most preferably, the surface properties of a surface that is suitable for cell attachment results in at least 90% of the cells adhering to the surface within eight, six, four, two hours of plating.

As used herein, "detectable change in impedance between or among said electrodes" (or "detectable change in impedance between or among the electrode structures") means that the impedance between or among the electrodes (or electrode structures) would have a significant change that can be detected by an impedance analyzer or impedance measurement circuit when cells attach on the electrode surfaces. The impedance change refers to the difference in impedance values when cells are attached to the electrode surface and when cells are not attached to the electrode surface, or when the number, type, activity, adhesiveness, or morphology of cells attached to the electrode-comprising surface of the apparatus changes. In most cases, the change in impedance is larger than 0.1% to be detectable. Preferably, the detectable change in impedance is larger than 1%, 2%, 5%, or 8%. More preferably, the detectable change in impedance is larger than 10%. Impedance between or among electrodes is typically a function of the frequency of the applied electric field for measurement. "Detectable change in impedance between or among the electrodes" does not require the impedance change at all frequencies being detectable. "Detectable change in impedance between or among said electrodes" only requires a detectable change in impedance at any single frequency (or multiple frequencies). In addition, impedance has two components, resistance and reactance (reactance can be divided into two categories, capacitive reactance and inductive reactance). "Detectable change in impedance between or among said electrodes" requires only that either one of resistance and reactance has a detectable change at any single frequency or multiple frequencies. In the present application, impedance is the electrical or electronic impedance. The method for the measurement of such impedance is achieved by, (1) applying a voltage between or among the electrodes at a given frequency (or multiple frequencies, or having specific voltage waveform) and monitoring the electrical current through said electrodes at the frequency (or multiple frequencies, or having specific waveform), dividing the voltage amplitude value by the current amplitude value to derive the impedance value; (2) applying an electric current of a single frequency component (or multiple frequencies or having specific current wave form) through said electrodes and monitoring the voltage resulted between or among said electrodes at the frequency (or multiple frequencies, or having specific waveform), dividing the voltage amplitude value by the current amplitude value to derive the impedance value; (3) other methods that can measure or determine electric impedance. Note that in the description above of "dividing the voltage amplitude value by the current amplitude value to derive the impedance value", the "division" is done for the values of current amplitude and voltage amplitude at same frequencies. Measurement of such electric impedance is an electronic or electrical process that does not involve the use of any reagents.

As used herein, "multiple pairs of electrodes or electrode structures spatially arranged according to wells of a multi-well microplate" means that the multiple pairs of electrodes or electrode structures of a device or apparatus are spatially arranged to match the spatial configuration of wells of a multi-well microplate so that, when desirable, the device can be inserted into, joined with, or attached to a multiwell plate (for example, a bottomless multiwell plate) such that multiple wells of the multi-well microplate will comprise electrodes or electrode structures.

As used herein, "arranged in a row-column configuration" means that, in terms of electric connection, the position of an electrode, an electrode array or a switching circuit is identified by both a row position number and a column position number.

As used herein, "each well contains substantially same number . . . of cells" means that the lowest number of cells in a well is at least 50% of the highest number of cells in a well. Preferably, the lowest number of cells in a well is at least 60%, 70%, 80%, 90%, 95% or 99% of the highest number of cells in a well. More preferably, each well contains an identical number of cells.

As used herein, "each well contains . . . same type of cells" means that, for the intended purpose, each well contains same type of cells; it is not necessary that each well contains exactly identical type of cells. For example, if the intended purpose is that each well contains mammalian cells, it is permissible if each well contains same type of mammalian cells, e.g., human cells, or different mammalian cells, e.g., human cells as well as other non-human mammalian cells such as mice, goat or monkey cells, etc.

As used herein, "each well contains . . . serially different concentration of a test compound" means that each well contains a test compound with a serially diluted concentrations, e.g., an one-tenth serially diluted concentrations of 1 M, 0.1 M, 0.01 M, etc.

As used herein, "dose-response curve" means the dependent relationship of response of cells on the dose concentration of a test compound. The response of cells can be measured by many different parameters. For example, a test compound is suspected to have cytotoxicity and cause cell death. Then the response of cells can be measured by percentage of non-viable (or viable) cells after the cells are treated by the test compound. Plotting this percentage of non-viable (or viable) cells as a function of the dose concentration of the test compound constructs a dose response curve. In the present application, the percentage of non-viable (or viable) cells can be expressed in terms of measured impedance values, or in terms of cell index derived from impedance measurement, or in terms of cell change indexes. For example, for a give cell type and under specific cellular physiological condition (e.g., a particular cell culture medium), cell index can be shown to have a linear correlation or positive correlation with the number of viable cells in a well from which cell index was derived from the impedance measurement. Thus, in the present application, one can plot cell index as a function of the dose concentration of the test compound to construct a "dose-response curve". Note that, generally, cell index not only correlate with the number of viable cells in the wells but also relate to the cell morphology and cell attachment. Thus plotting cell index versus dose concentration provides information not only about number of cells but also about their physiological status (e.g. cell morphology and cell adhesion). Furthermore, an important advantage offered by the system and devices of the present invention is that in a single experiment, one can obtain "dose-response curves" at multiple time points since the system allows for the continuous monitoring of cells and provides impedance measurement at many time points over a time range as short as a few minutes to as long as days or weeks.

As used herein, "microelectrode strip or electrode strip" means that a non-conducting substrate strip on which electrodes or electrode structure units are fabricated or incorporated. The non-limiting examples of the non-conducting substrate strips include polymer membrane, glass, plastic sheets, ceramics, insulator-on-semiconductor, fiber glass (like those for manufacturing printed-circuits-board). Electrode structure units having different geometries can be fabricated or made on the substrate strip by any suitable microfabrication, micromachining, or other methods. Non-limiting examples of electrode geometries include interdigitated electrodes, circle-on-line electrodes, diamond-on-line electrodes, castellated electrodes, spiral electrodes or sinusoidal electrodes. Characteristic dimensions of these electrode geometries may vary from as small as less than 5 micron, or less than 10 micron, to as large as over 200 micron, over 500 micron, over 1 mm. The characteristic dimensions of the electrode geometries refer to the smallest width of the electrode elements, or smallest gaps between the adjacent electrode elements, or size of a repeating feature on the electrode geometries. The microelectrode strip can be of any geometry for the present invention. One exemplary geometry for the microelectrode strips is rectangular shape—having the width of the strip between less than 50 micron to over 10 mm, and having the length of the strip between less than 60 micron to over 15 mm. An exemplary geometry of the microelectrode strips may have a geometry having a width of 200 micron and a length of 20 mm. A single microelectrode strip may have two electrodes serving as a measurement unit, or multiple such two-electrodes serving as multiple measurement units, or a single electrode structure unit as a measurement unit, or multiple electrode structure units serving as multiple electrode structure units. In one exemplary embodiment, when multiple electrode structure units are fabricated on a single microelectrode strip, these electrode structure units are positioned along the length direction of the strip. The electrode structure units may be of squared-shape, or rectangular-shape, or circle shapes. Each of electrode structure units may occupy size from less than 50 micron by 50 micron, to larger than 2 mm×2 mm.

As used herein, "sample" refers to anything which may contain a moiety to be isolated, manipulated, measured, quantified, detected or analyzed using apparatuses, microplates or methods in the present application. The sample may be a biological sample, such as a biological fluid or a biological tissue. Examples of biological fluids include suspension of cells in a medium such as cell culture medium, urine, blood, plasma, serum, saliva, semen, stool, sputum, cerebral spinal fluid, tears, mucus, amniotic fluid or the like. Biological tissues are aggregates of cells, usually of a particular kind together with their intercellular substance that form one of the structural materials of a human, animal, plant, bacterial, fungal or viral structure, including connective, epithelium, muscle and nerve tissues. Examples of biological tissues also include organs, tumors, lymph nodes, arteries and individual cell(s). The biological samples may further include cell suspensions, solutions containing biological molecules (e.g. proteins, enzymes, nucleic acids, carbohydrates, chemical molecules binding to biological molecules).

As used herein, a "liquid (fluid) sample" refers to a sample that naturally exists as a liquid or fluid, e.g., a biological fluid. A "liquid sample" also refers to a sample that naturally exists in a non-liquid status, e.g., solid or gas, but is prepared as a liquid, fluid, solution or suspension containing the solid or gas sample material. For example, a liquid sample can encompass a liquid, fluid, solution or suspension containing a biological tissue.

A "compound" or "test compound" is any compound whose activity or direct or indirect effect or effects on cells is investigated in any assay. A test compound can be any compound, including, but not limited to, a small molecule, a large molecule, a molecular complex, an organic molecule, an inorganic molecule, a biomolecule or biological molecule such as but not limited to a lipid, a steroid, a carbohydrate, a fatty acid, an amino acid, a peptide, a protein, a nucleic acid, or any combination thereof. A test compound can be a synthetic compound, a naturally occurring compound, a derivative of a naturally-occurring compound, etc. The structure of a test compound can be known or unknown. In one application of the present invention, a compound is capable of, or is suspected of, effecting cell adhesion or cell spreading. In another application of present invention, a compound is capable of, or is suspected of, stimulating or inhibiting cell adhesion or cell spreading. In still another application, a compound is capable of, or is suspected of, interacting with cells (for example, binding to cell surface receptor, or inhibiting certain intracellular signal transduction pathway, or activating cells).

A "known compound" is a compound for which at least one activity is known. In the present invention, a known compound preferably is a compound for which one or more direct or indirect effects on cells is known. Preferably, the structure of a known compound is known, but this need not be the case. Preferably, the mechanism of action of a known compound on cells is known, for example, the effect or effects of a known compound on cells can be, as nonlimiting examples, effects on cell beating, cell viability, cell adhesion, apoptosis, cell differentiation, cell proliferation, cell morphology, cell cycle, IgE-mediated cell activation or stimulation, receptor-ligand binding, cell number, cell quality, cell cycling, cell adhesion, cell spreading, etc.

An "impedance value" is the impedance measured for electrodes in a well with or without cells present. Impedance is generally a function of the frequency, i.e., impedance values depend on frequencies at which the measurement was conducted. For the present application, impedance value refers to impedance measured at either single frequency or multiple frequencies. Furthermore, impedance has two components, one resistance component and one reactance component. Impedance value in the present application refers to resistance component, or reactance component, or both resistance and reactance component. Thus, when "impedance value" was measured or monitored, we are referring to that, resistance, or reactance, or both resistance and reactance were measured or monitored. In many embodiments of the methods of the present application, impedance values also refer to parameter values that are derived from raw, measured impedance data. For example, cell index, or normalized cell index, or delta cell index could be used to represent impedance values.

A "Cell Index" or "CI" is a parameter that can derived from measured impedance values and that can be used to reflect the change in impedance values. There are a number of methods to derive or calculate Cell Index. The details of the method for calculating Cell Index, Normalized Cell Index, Delta Cell Index and cell change index can be found in U.S. patent application Ser. No. 10/705,447, filed on Nov. 10, 2003; U.S. patent application Ser. No. 10/705,615, filed on Nov. 10, 2003; U.S. patent application Ser. No. 10/987,73, filed on Nov. 12, 2004; U.S. patent application Ser. No. 11/055,639, filed on Feb. 9, 2005; U.S. patent application Ser. No. 11/198,831, filed on Aug. 4, 2005; U.S. patent application Ser. No. 11/197,994, filed on Aug. 4, 2005; U.S. patent application Ser. No. 11/235,938, filed on Sep. 27, 2005, all of them are incorporated here by reference.

A "Normalized Cell Index" at a given time point is calculated by dividing the Cell Index at the time point by the Cell Index at a reference time point. Thus, the Normalized Cell Index is 1 at the reference time point. Generally, for an assay involving treatment of the cells with compounds or with other bio-manipulation of the cells, the reference time point is the last time point for impedance measurement before the treatment of the cells.

A "delta cell index" at a given time point is calculated by subtracting the cell index at a standard time point from the cell index at the given time point. Thus, the delta cell index is the absolute change in the cell index from an initial time (the standard time point) to the measurement time.

A "Cell Change Index" or "CCI" is a parameter derived from Cell Index and "CCI" at a time point is equal to the $1^{St}$ order derive of the Cell Index with respect to time, divided by the Cell Index at the time point. In other words, CCI is calculated as $$CCI(t) = \frac{dCI(t)}{CI(t) \cdot dt}.$$

The term "extracellular recording" refers to measuring, monitoring and/or recording of electric potential difference between two electrodes typically caused by ionic movement or ionic current through the media or solution due to charge fluctuations across ion channels in a cell or in a group of cells. The cells are in the media or the solution. In contrast to intracellular recording where the recording electrodes are placed inside a cell through the cell membrane, the extracellular recording electrodes are located outside of the cells.

B. Method to Assess and Quantify Cardiomyocyte Viability In Vitro Using Cell Sensor Impedance Technology The methods and devices of the present invention may assess or quantify the viability of cardiomyocyte or cardiomyocyte precursor cells in addition to performing extracellular recording assays. Such assessment may be performed prior to performing an extracellular recording assay to assess the initial viability or characteristics of cells or may be performed periodically throughout the extracellular recording process to continually monitor the viability or characteristics of cells, or may be performed in parallel with extracellular recording.

Isolated primary cardiomyocytes, ES-derived cardiomyocytes and adult stem cell-derived cardiomyocytes can be maintained in culture. These cells provide an excellent model system to study the effect of drugs and other factors on cardiomyocyte viability.

Exemplary steps involved in using an impedance-monitoring system for measurement of cardiomyocyte viability include:
(1) Provide a single-well or multi-well device that comprise microelectrode arrays in well(s) of the device, which can be used for monitoring cell-substrate impedance.
(2) Optionally coat wells of the device with either fibronectin or other matrix proteins.
(3) Seed either embryonic stem cells (ES cells) of mammalian origin, mammalian adult stem cell-derived cardiomyocytes or primary cardiomyocytes isolated directly from mammalian heart tissue at specific seeding densities to the wells of the device.
(4) Allow the cells to attach and spread.
(5) Monitor cardiomyocyte viability over time using the impedance-monitoring system to monitor electrode impedance at pre-specified intervals of time (non-limiting examples of the time include 5, 15, 30 minutes, 1 hr and 2 hrs) for specified length of time such as 12, 24, 48, 72 hours or longer.

One example of the impedance measurement system is ACEA Biosciences' RT-CES system, where the device is ACEA E-PLATE in the form of microtiter plates whose wells comprise microelectrode structures. Thus in a related embodiment, exemplary steps involved in using the RT-CES system for measurement of cardiomyocyte viability include:
(1) Optionally coat E-PLATES with either fibronectin or other matrix proteins.
(2) Seed either embryonic stem cells (ES cells) of mammalian origin, mammalian adult stem cell-derived cardiomyocytes or primary cardiomyocytes isolated directly from mammalian heart tissue at specific seeding densities to the wells of the device.
(3) Allow the cells to attach and spread.
(4) Monitor cardiomyocyte viability over time using the impedance-monitoring system to monitor electrode impedance at pre-specified intervals of time (non-limiting examples of the time include 5, 15, 30 minutes, 1 hr and 2 hrs) for specified length of time such as 12, 24, 35, 48, 72 hours or longer.

As an example, we describe here the use of the ACEA RT-CES system to measure and monitor the attachment, growth and viability of mouse ES-derived cardiomyocytes which were seeded at different seeding densities. Mouse ES cells were seeded at a density ranging from 3000 cells to 50,000 cells per well in ACEA E-PLATES that had been precoated with fibronectin. The attachment, growth and viability of the cells were monitored on the RT-CES system measuring impedance signal in the form of cell index every 30 minutes for 48 hours. At about 48 hrs after cell seeding, the growth of the cells had ceased and the appearance of beating cardiomyocytes were evident as judged by looking at the cells inside the E-PLATE under the microscope. As such, these cells would be suitable for use, for example, in extracellular recording experiments to determine the effect of external stimuli, such as changes in cardiomyocyte beating after administration of a test compound, or in the experiments to monitor cardiomyocyte beating through impedance measurement at milli-second time resolution. FIG. 1 shows the cell index curves measured on RT-CES system for 4 different seeding densities (3750, 7500, 15,000 and 30,000 cells per well) of mouse ES-derived cardiomyocytes. For such long term measurement, cell electrode impedance and corresponding cell indices were measured at about 15 minute intervals. Based on the cell index growth and viability curves, it is evident that the extent of the impedance signal correlates well with the seeding density of viable ES-derived cardiomyocytes.

C. Method to Assess and Quantify Modulation of Cardiomyocyte Viability In Vitro Using Cell Sensor Impedance Technology Certain cardiotoxic drugs can directly affect the viability of cardiomyocytes. Accordingly, continuing to monitor the viability of cardiomyocytes over time may be used to supplement data obtained from extracellular recording of cells. Exemplary steps involved in using an impedance-measurement system for measurement of loss of viability of cardiomyocyte include:
(1) Optionally coat E-PLATES with either fibronectin or other matrix proteins.
(2) Seed either embryonic stem cells (ES cells) of mammalian origin, mammalian adult stem cell-derived cardiomyocytes or primary cardiomyocytes isolated directly from mammalian heart tissue at specific seeding densities to the wells of the device.
(3) Allow the cells to attach and spread.
(4) Monitor cardiomyocyte viability over time using the impedance-monitoring system to monitor electrode impedance at pre-specified intervals of time for specified length of time such as 12, 24, 37, 48, 72 hours or longer
(5) At certain time after cell seeding, treat the cell with cytotoxic agent at one or more concentration; using the vehicle that the agent is dissolved in as a control.
(6) Continue monitoring the cardiomyocytes at pre-specified intervals of time for specified length of time such as additional 12, 24, 48, 72 hours or longer
(7) Quantify the extent of cardiotoxicity by normalizing the cell index values immediately prior to agent addition and determine the normalized cell index at a given time point after agent addition; alternatively the rate of cytotoxicity can also be quantified for a given time period after compound addition for a given agent concentration or a group of concentrations. The extent of cytotoxicity can be expressed as IC-50 value which quantifies the activity of the agent with respect to the cardiomyocytes.

As an example, we describe here the use of the ACEA RT-CES system to measure and monitor the attachment and growth of mouse ES cells derived cardiomyocytes and subsequently treated with a cytotoxic agent (FIG. 2). Mouse ES-derived cardiomyocytes were seeded at a density of 25,000 cells per well in ACEA E-Plates that had been precoated with fibronectin. The attachment and growth of the cells were monitored on RT-CES system for 72 hours and then treated with increasing doses of the compound of sodium dichromate dehydrate which is known to induce cytotoxicity.

Figure 2A:
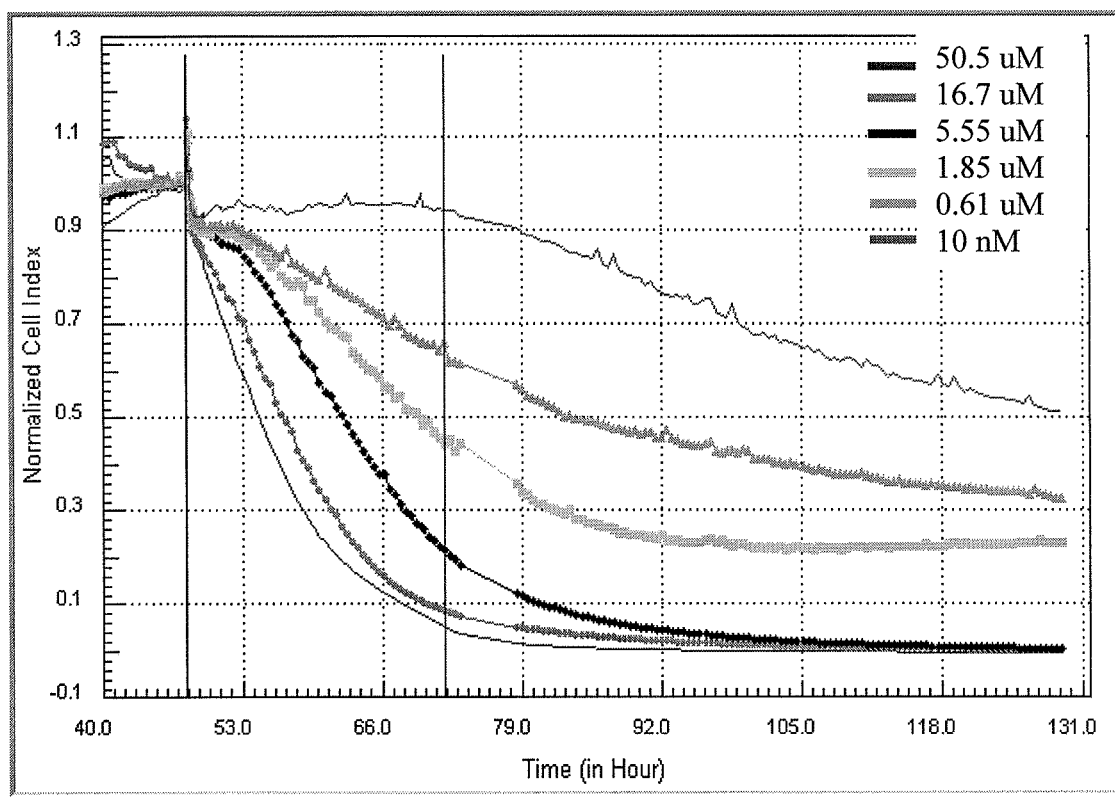
FIG. 2A shows the time dependent, normalized cell index for embryonic stem cell derived cardiomyocytes in different wells treated with different concentrations of sodium dichromate dehydrate.
Figure 2B:
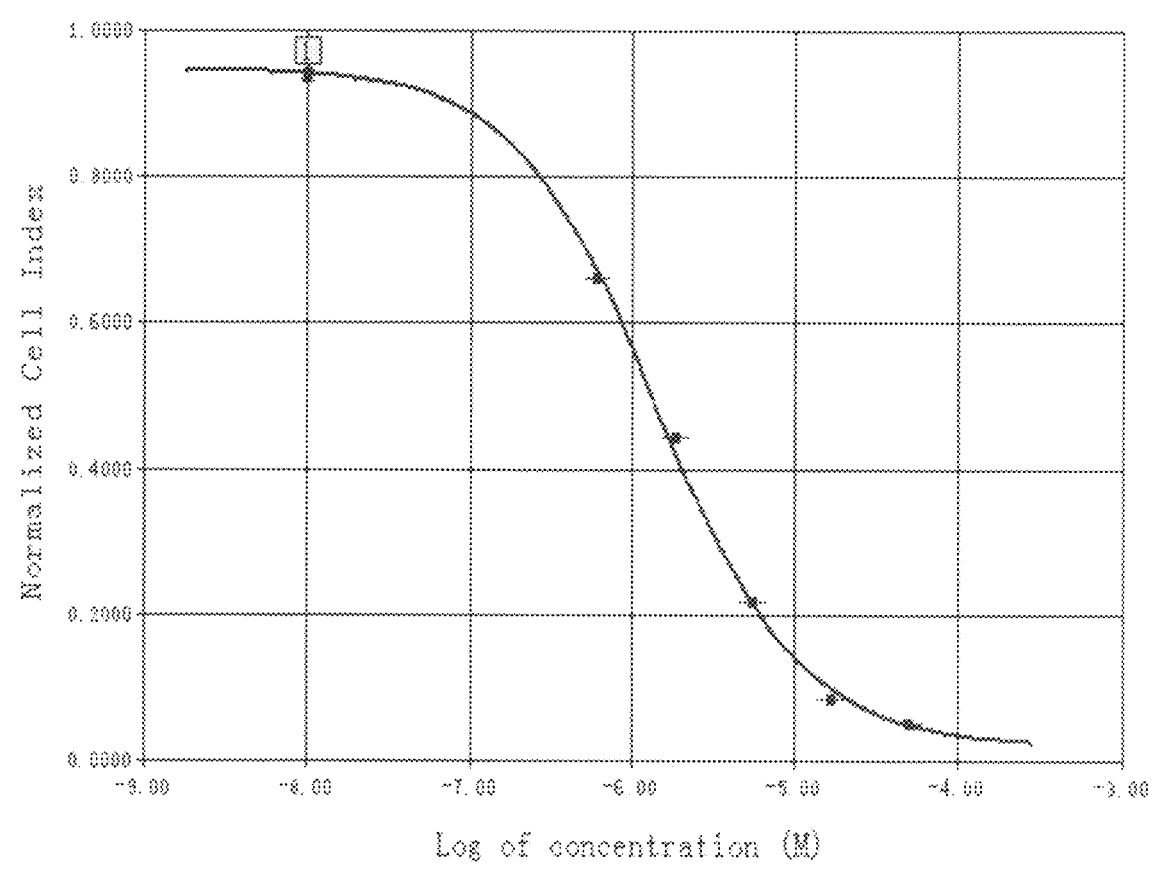
FIG. 2B shows the dose dependent normalized cell index values at 24 hrs after treatment of the cells with dichromate dehydrate as a function of the concentration of dichromate dehydrate.

According to FIG. 2A of the plot of normalized cell index for cells in different wells treated with different concentrations of sodium dichromate dehydrate (SDD), SDD causes a concentration dependent decrease in viability of ES-derived cardiomyocytes. To quantify the extent of sodium dichromate dehydrate activity against the cardiomyocytes, the normalized cell indices at 24 hrs after compound treatment were plotted against the log of the corresponding sodium dichromate dehydrate concentrations. From the sigmoidal curve, shown in FIG. 2B, half maximal activity or IC-50 value of 1.48 uM was derived for the compound.

D. Method to Assess and Quantify Modulation of Cardiomyocyte Morphology In Vitro Using Cell Sensor Impedance Technology Certain cardiotoxic drugs can illicit their effect by affecting the morphological aspects of cardiomyocyte morphology. For example, it is well known that compounds such as b-2 adrenergic receptor agonists can induce morphological changes resulting in an elongated cardiomyocyte morphology, otherwise known as hypertrophy. Morphological changes can occur immediately in the order of minutes as with certain GPCR agonists or can be of longer duration detectable over several days. The time resolution of the RT-CES system can be used to distinguish between different kinds of morphological effects. The steps involved in using an impedance-monitoring system on the RT-CES system for measurement of morphological modulation of cardiomyocytes include:

(1) Optionally coat E-PLATES with either fibronectin or other matrix proteins.
(2) Seed either embryonic stem cells (ES cells) of mammalian origin, mammalian adult stem cell-derived cardiomyocytes or primary cardiomyocytes isolated directly from mammalian heart tissue at specific seeding densities to the wells of the device.
(3) Allow the cells to attach and spread.
(4) Monitor cardiomyocyte viability over time using the impedance-monitoring system at prespecified intervals of time for 12, 24, 48, 72 hours or longer
(5) At certain time after cell seeding, treat the cell with agents that may cause morphology changes at one or more concentration; using the vehicle that the agent is dissolved in as a control.
(6) Continue monitoring the cardiomyocytes at 1 minute intervals for at least 1-2 hours to capture any immediate morphological changes and continue to monitor at 30 minutes intervals of time for additional 12, 24, 48, 72 hours or longer to detect long term morphological changes
(7) Quantify the extent of morphological change by normalizing the cell index values immediately prior to agent addition and determine the normalized cell index at a given time point after agent addition; The extent of morphological change can be expressed as EC-50 value which quantifies the activity of the agent with respect to the cardiomyocyte shape changes.

Figure 3A:
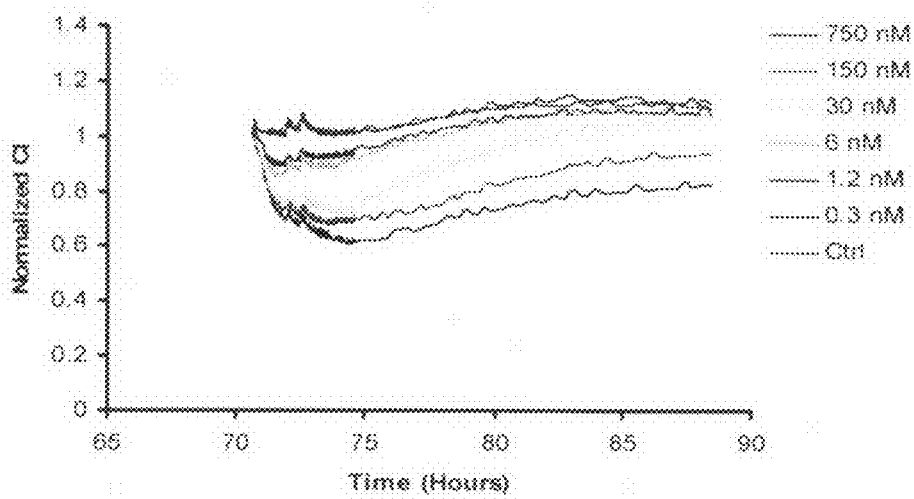
FIG. 3A shows that the time dependent, normalized cell index for embryonic stem cell derived cardiomyocytes in different wells treated with different concentrations of isoproteranol.
Figure 3B:
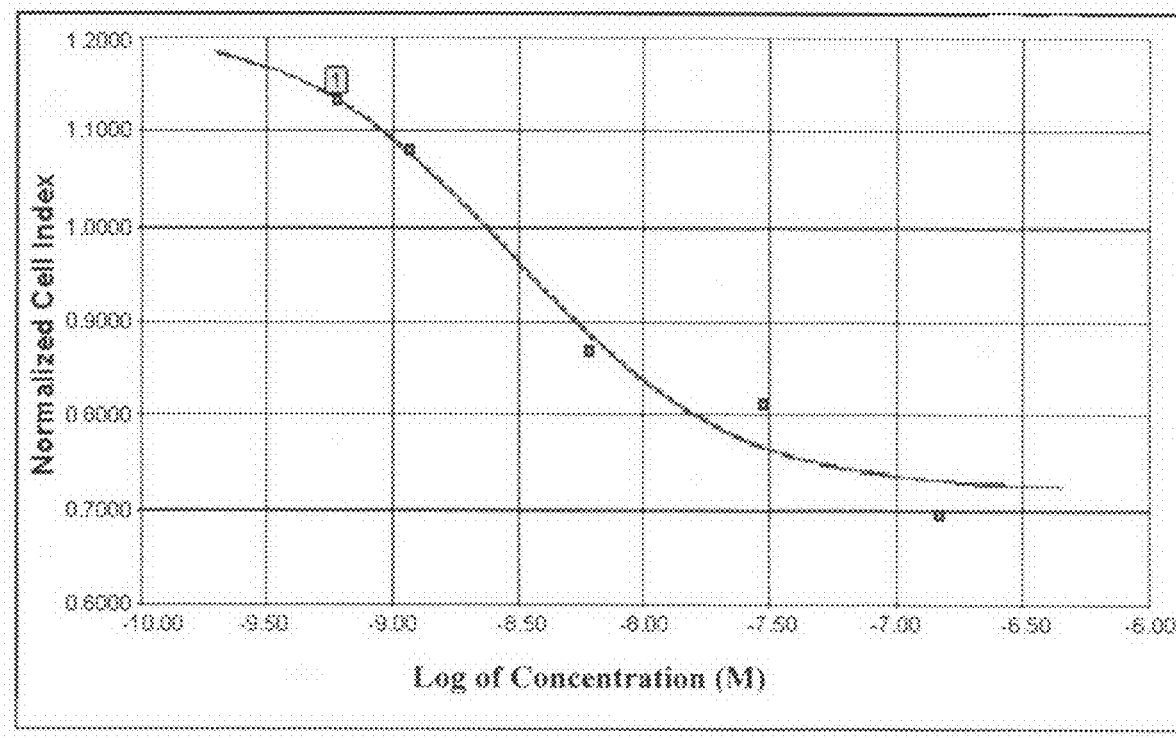
FIG. 3B shows the dose dependent, normalized cell index at several hours after treatment of the cells with isoproteranol as a function of the concentration of isoproteranol.

As an example, we describe here the use of the ACEA RT-CES system to measure and monitor the attachment and growth of mouse ES cells derived cardiomyocytes and subsequently treated with isoproteranol, a β2 adrenergic receptor agonist known to induce hypertrophy (FIG. 3A). Mouse ES-derived cardiomyocytes were seeded at a density of 25,000 cells per well in ACEA E-PLATES that had been precoated with fibronectin. The attachment and growth of the cells were monitored on RT-CES system for 72 hours and then treated with increasing doses of the compound isoproteranol. According to FIG. 3A, isoproteranol causes a concentration dependent change in cell index readings. The timing of the cell index change is consistent with a change in the morphology of the cells which we have shown previously for other GPCR agonists in primary cells (Yu et al (2006) Real-time monitoring of morphological changes in living cells by electronic cell sensor arrays: an approach to study G protein-coupled receptors; Analytical Chemistry, Vol 78, pages 35-43). To quantify the extent of isoproteranol-induced morphological changes in mouse ES-derived cardiomyocytes, the normalized cell indices were plotted against the log of the corresponding isoproteranol concentrations (FIG. 3B). From the sigmoidal curve generated a half maximal activity or IC-50 value of 3.1 nM was derived for the compound.

E. Method to Assess and Quantify Cardiomyocyte Beating In Vitro Using Cell Sensor Impedance Technology Isolated primary cardiomyocytes as well as ES-derived cardiomyocytes retain the ability to beat in culture. These cells provide an excellent model system to study cardiomyocyte function in vitro, especially with regards to cardiotoxicity. A number of cardiotoxic drugs are known to affect certain heart channels, such as the ERG channels, that are involved in excitation-contraction coupling of cardiomyocytes. Cardiomyocytes have an innate ability to undergo mechanotransduction, that is that the spontaneous force generation of the beating cardiomyocyte is translated to intracellular biochemical signals. Membrane receptors such as integrins, ion channels and other proteins have been shown to play a crucial role in cardiac mechanotransduction and lead to a continuous and rhythmic dynamics of the cardiac actin cytoskeleton and morphology. Because the impedance-based technology and system can sensitively and precisely detect transient changes in morphology and adhesive capacity of the cells, it can be used to monitor cardiomyocyte beating in vitro.

The steps involved in using an impedance-measurement system for measurement of cardiomyocyte beating include:
 (1) Provide a single-well or multi-well device that comprise microelectrode arrays in well(s) of the device, which can be used for monitoring cell-substrate impedance.
 (2) Optionally coat wells of the device with either fibronectin or other matrix proteins.
 (3) Seed either embryonic stem cells (ES cells) of mammalian origin or primary cardiomyocytes at specific seeding densities to the wells of the device.
 (4) Allow the cells to attach and spread.
 (5) After a specified period of time unique to ES-derived cardiomyocytes or primary cardiomyocytes, monitor cardiomyocyte beating using the impedance-monitoring system to monitor electrode impedance by using milli-second kinetic readout to resolve the individual beat cycles of the cells.

The milli-second kinetic readout requires that the impedance measurement system can provide impedance measurement data at milli-second time resolution. In other words, the time difference between two consecutive impedance measurement for a well shall be in the range of milli-seconds (e.g., less than 500 milli-second, less than 300 milli-second, less than 100 milli-second, less than 40 milli-second, less than 30 milli-second, less than 20 milli-second, less than 10 millisecond, or less than 1 millisecond or faster). The milli-second kinetic readout is required to resolve the individual beat cycles of the cells. Thus, the time resolution for the impedance measurement should allow the system to perform measurement at least two time points for each beat cycle, or at more than two points for each beat cycle. These milli-second kinetic readouts may be performed within extracellular recording experiments by switching between an extracellular recording mode and impedance mode via a switching means. The fast kinetic readouts associated with such an impedance based system permits the user to obtain multiple impedance measurements to obtain the impedance data for one or more beating cycle of the cardiomyocytes between extracellular recording measurements.

One example of the impedance measurement systems is an improved fast-impedance-measurement system from ACEA Biosciences, where the device is the E-PLATE in the form of microliter plates whose wells comprise microelectrode structures. An important aspect of the present invention is that the impedance measurement circuitry together electronic switching circuitry and the associated is capable of measuring electronic impedances of the one or more wells at milli-second time resolution, that is to say, the time difference between two adjacent impedance measurements for each well is in the range of milli-seconds. This requirement is important, especially when the system comprises a device having multiple wells such as 4 wells, 8 wells, 16 wells or 96 wells. For example, if the system comprises a device having 96 wells, the system hardware and software should be capable of measuring the impedances of all the 96 wells with milli-second time resolution between two adjacent impedance measurement points for each and every well. Preferably, the time difference between two adjacent measurement points for each and every given well is less than 500 milliseconds. More preferably, the time difference between two adjacent measurement points for each and every given well is less than 300 milliseconds. More preferably, the time difference between two adjacent measurement points for each and every given well is less than 200 milliseconds. Still more preferably, the time difference between two adjacent measurement points for each and every given well is less than 100 milliseconds. Still more preferably, the time difference between two adjacent measurement points for each and every given well is less than 40 milliseconds. Still more preferably, the time difference between two adjacent measurement points for each and every given well is less than 20 milliseconds. Still more preferably, the time difference between two adjacent measurement points for each and every given well is less than 10 milliseconds.

A number of improvements in the impedance measurement circuitry, electronic switching circuitry, communication between impedance measurement circuitry and software can be used to achieve such milli-second time resolution. One aspect of improvements includes the use of fast processing electronic chips for analogue-to-digital conversion, for parallel digital signal processing and data calculation with field-programmable gate array (FPGA) and for fast communication between the impedance measurement circuitry and software. Another aspect of improvements includes the use of multiple analogue-to-digital (AD) conversion channels so that analog electronic signals from multiple channels can be converted to digital signals simultaneously. Such parallel AD conversion is important, particular for the system having multiple wells, each of which's measurement time resolution is required to be in the milli-second resolution. Another very important aspect of improvements is to replace typical working mode of "measurement of one-well's impedance at a time" with a mode of "measurement of multiple-wells' impedance at a time". In "one-well at a time" mode, when the software issue a command for measuring one well's impedance, the measurement circuitry would perform the measurement for one well including signal generation to the well, converting the voltage signal and the electric current signal for the well to digital signal, digitally processing the signals to do impedance calculation and sending the well's impedance data to the computer over the communication line between the impedance measurement circuitry and the computer. The system will not perform any measurement for another well until the completion of the measurement of this well and until receiving another command for the measurement of another well. In "multiple-wells at a time" mode, the software would issue a command for measuring multiple wells' impedance. The measurement circuitry would simultaneously or nearly simultaneously perform signal conversion, signal processing and impedance calculation for multiple wells. The multiple impedance data for the multiple wells would be sent over the communication lines to the computer sequentially with one well's data at time or simultaneously with more than one well's data being sent at a time. In this "measurement of multiple-wells' impedance at a time" mode, the system may be performing multiple tasks simultaneously, for example, while one well's impedance data is being measured and calculated, another well's impedance data may be communicated and sent over the communication lines to the computer.

The steps involved in using the system for measurement of cardiomyocyte function may include:

(1) Optionally coat E-PLATES with either fibronectin or other matrix proteins.
(2) Seed either ES cells of mammalian origin or primary cardiomyocytes at specific seeding densities.
(3) Allow the cells to attach and spread.
(4) After a specified period of time unique to ES-derived cardiomyocytes or primary cardiomyocytes, monitor cardiomyocyte beating using the RT-CES system by using milli-second kinetic readout to resolve the individual beat cycles of the cells.

Figure 4:
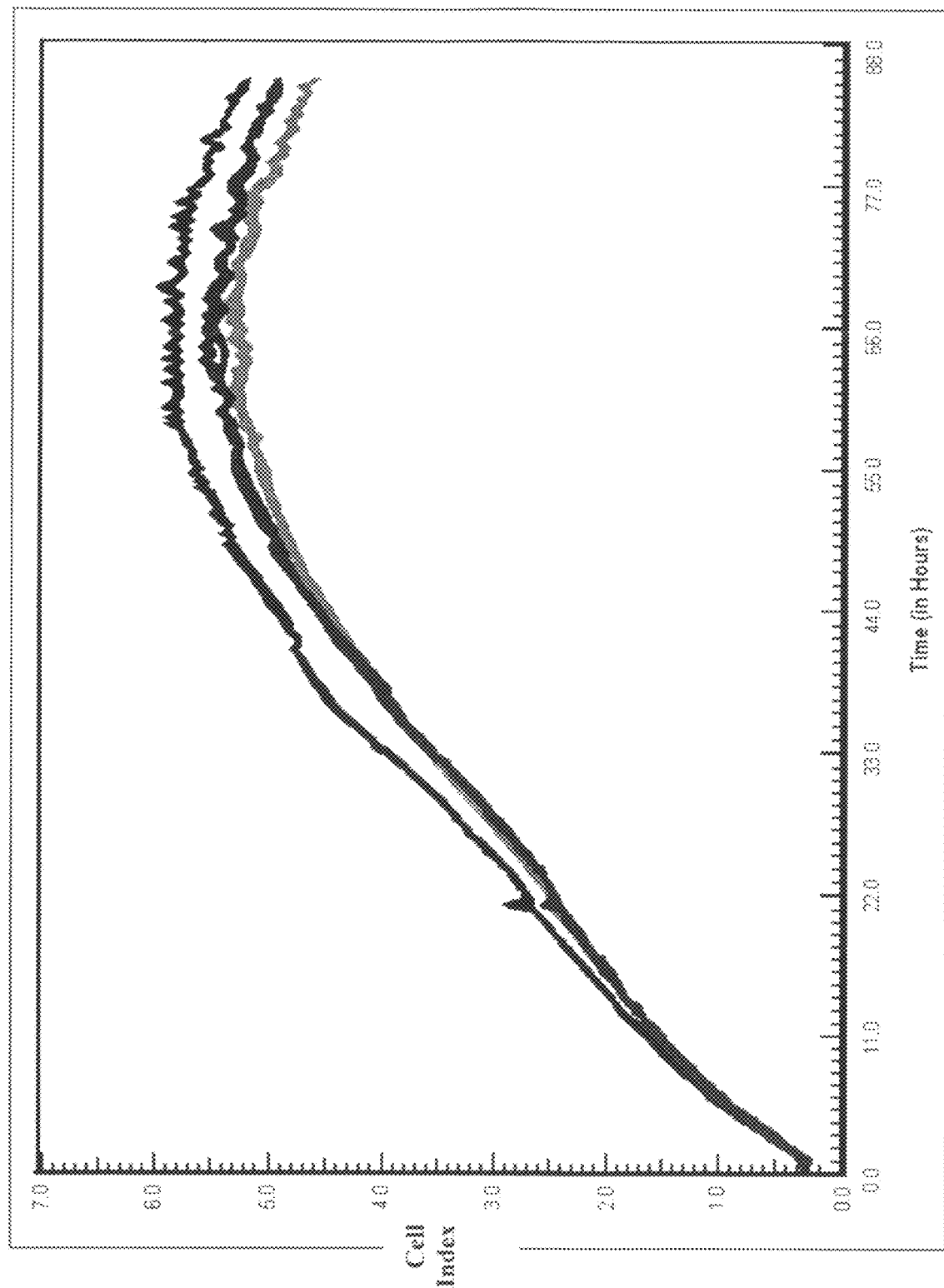
FIG. 4 shows the cell index curves of ES-derived cardiomyocytes measured on RT-CES system for 4 individual wells, with cell culture medium as background starting from cell seeding to about 86 hrs after cell seeding.

As an example, we describe here the use of the ACEA RT-CES system to measure and monitor the beating of cardiomyocytes using fast kinetic software. Mouse ES cells were seeded at a density of between 3,000 to 50,000 cells per well in ACEA E-PLATES that had been precoated with fibronectin. The attachment and growth of the cells were monitored on RT-CES system. FIG. 4 shows the cell index curves measured on RT-CES system for 4 individual wells, with cell culture medium as background starting from cell seeding to about 86 hrs after cell seeding. For such long term measurement, cell electrode impedance and corresponding cell indices were measured at about 15 minute intervals. As evidenced on these plots, the cell index curves were rather smooth up to about 44-48 hrs, after which there were "noises" or "small-spikes" on the cell index curves. Such spikes were most evident after about 60 hrs. Such spikes in the impedance or cell index readout are associated with the beating of the cells. During the synchronized beating of the cells, the cell morphology and cell adhesion/attachment to the electrodes change regularly in synchrony with the cell beating. Such regular or periodic changes in cell morphology and cell adhesion/attachment are then reflected in the changes in cell-electrode or cell-substrate impedances.

Figure 5B:
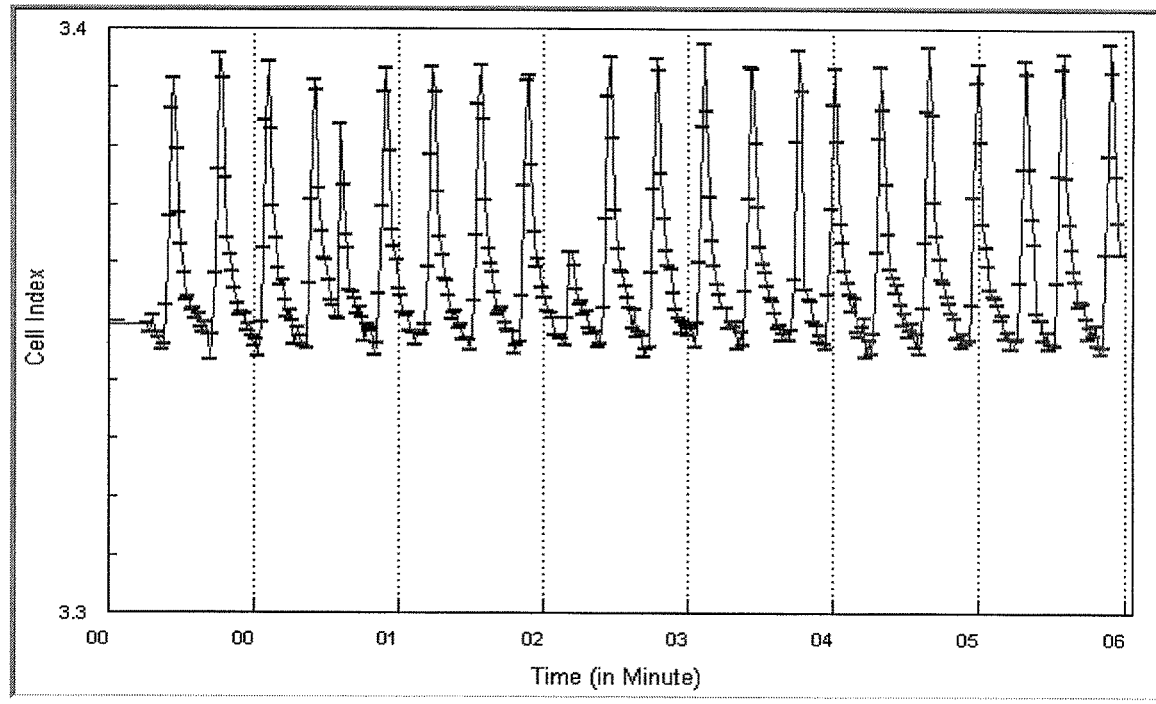
Figure 5C:
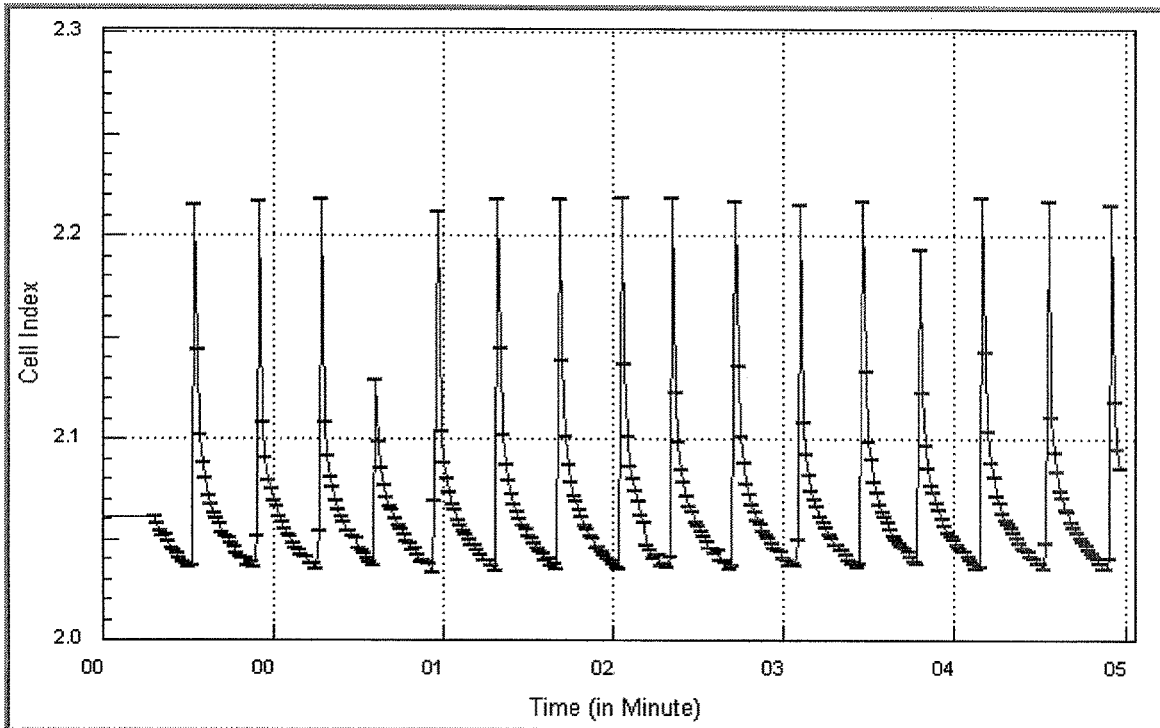
Figure 5D:
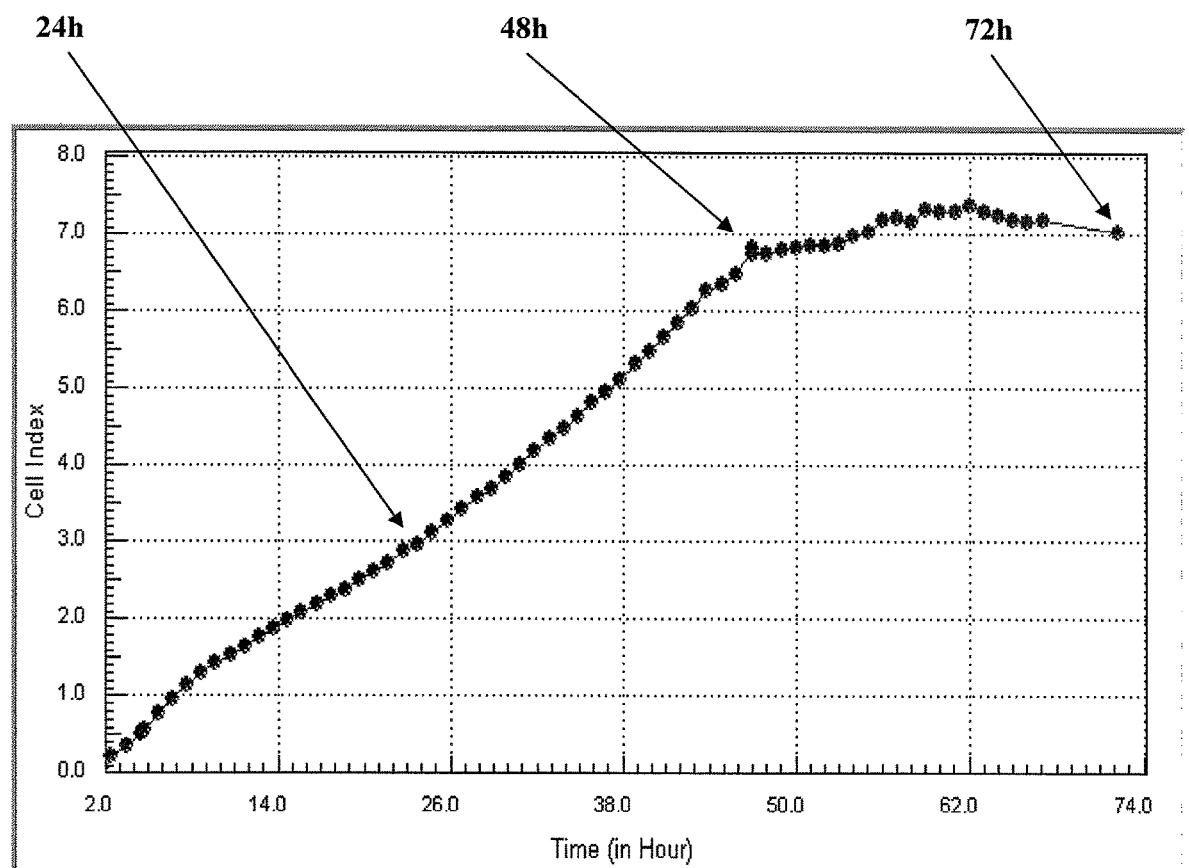
FIG. 5D shows the cell index curves monitored at 1 hr time resolution.

In order to monitor beating of cardiomyocytes, a specially designed software and measurement circuit hardware that are capable of millisecond impedance data acquisition (e.g., typically with time resolution between consecutive impedance measurement for a same well being less than 40 milli-seconds) was used to monitor the quick rhythmic beating of the cardiomyocytes. For such measurement, the background electrode impedance is measured with the cells inside the wells (note, this is in contrast with FIGS. 1 and 4, where the background measurement is performed using cell culture media). The software, together with specially designed hardware circuits was used to measure cardiomyocyte beating at distinct stages throughout its attachment and growth phases (FIG. 5). For a baseline reference, the impedance measurement was done on the ES cells at 24 hours where the cells had not fully spread and formed a tight monolayer and even though the cells appear to beat when visualized under a microscope, they do so asynchronously and as a result no net beating signal is detected (FIG. 5A). For plot, impedance readout has been converted into dimensionless cell indices. FIGS. 5B and 5C shows that ES cells that had fully spread and formed tight junctions with neighboring cells at 48 hours and 72 hours respectively, show regular impedance-spikes which correlate with the beating frequency of cardiomyocytes as judged by microscopic observation.

To use the measured cell index curves, it is important to further derive various physiologically relevant parameters. Several important parameters may include, the beating rate of the cardiomyocytes (i.e., how many times the cells beat within a unit of time for example, a minute), the beating amplitude (i.e. the magnitude of the beating of cells in terms of impedance change) the average amplitude intensity in a unit time as well as the average length of time between the beats, time of rise for a beat, time of decay for a beat. Because of the unique and complex nature of the impedance readout signals (smaller signal amplitude, sampling time resolution may be limited by the hardware and the software used), appropriate methods or techniques are required for analyzing cell index curves to derive the above mentioned parameters.

For deriving the beating rates of cardiomyocytes, one method may be by counting how many peaks there are within a given time frame (for example, one minute). For this approach to work, the sampling time resolution has to be sufficiently high so that the each beat of the cells does show a peak on the recorded cell index curves. In addition, determining a peak "automatically" also require some algorithm. For example, each peak would have to have one "rise" in cell index and also one "decay" in cell decay. Each "rise"-and-"decay" pair forms a single peak. The algorithm needs to determine such "rise" and "decay" portions of the curves and then counts a peak.

Figure 6A:
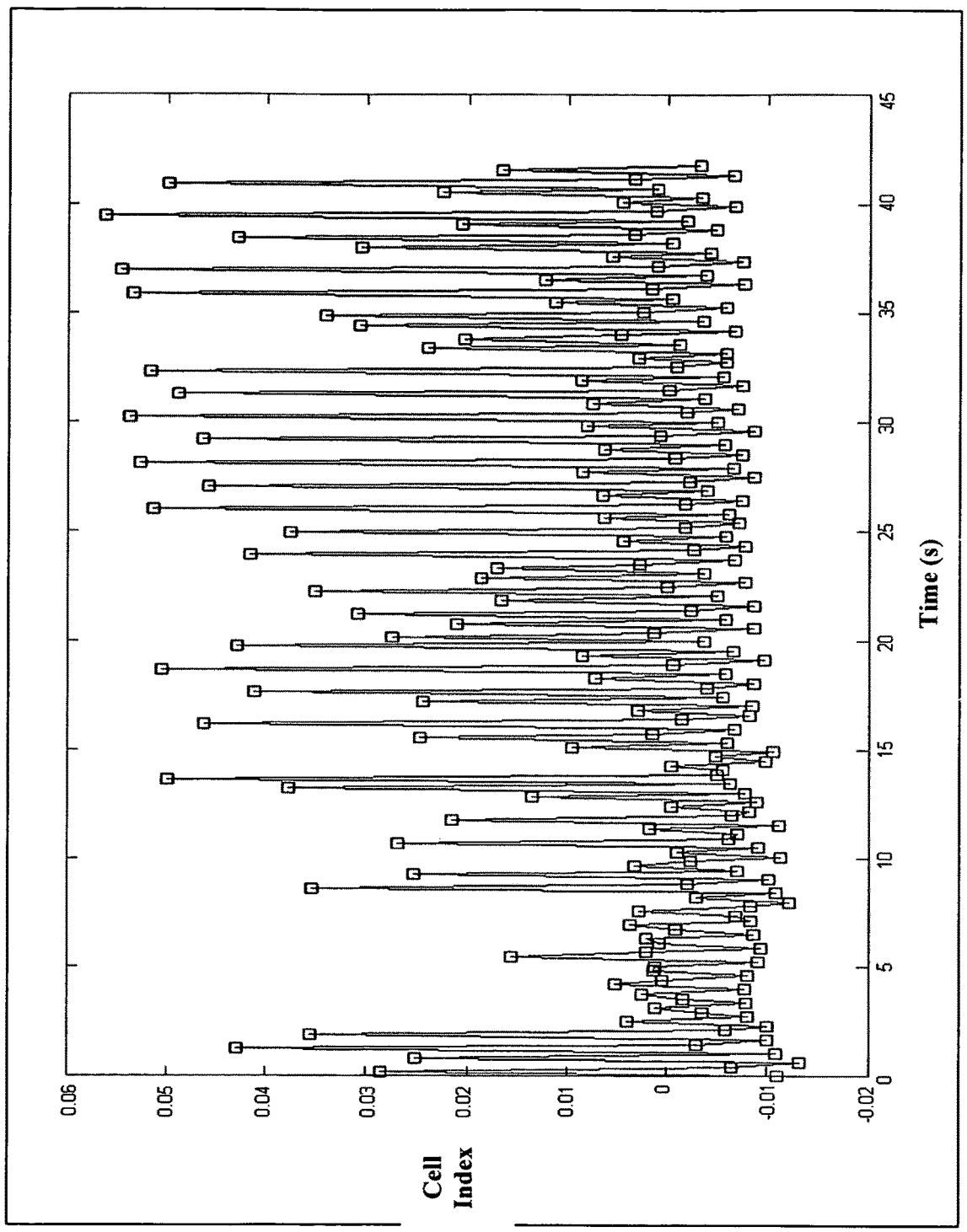
FIGS. 6A and 6B show the cell index curve for ES-derived cardiomyocytes and corresponding beat rate as analyzed using Fourier transform.
Figure 6B:
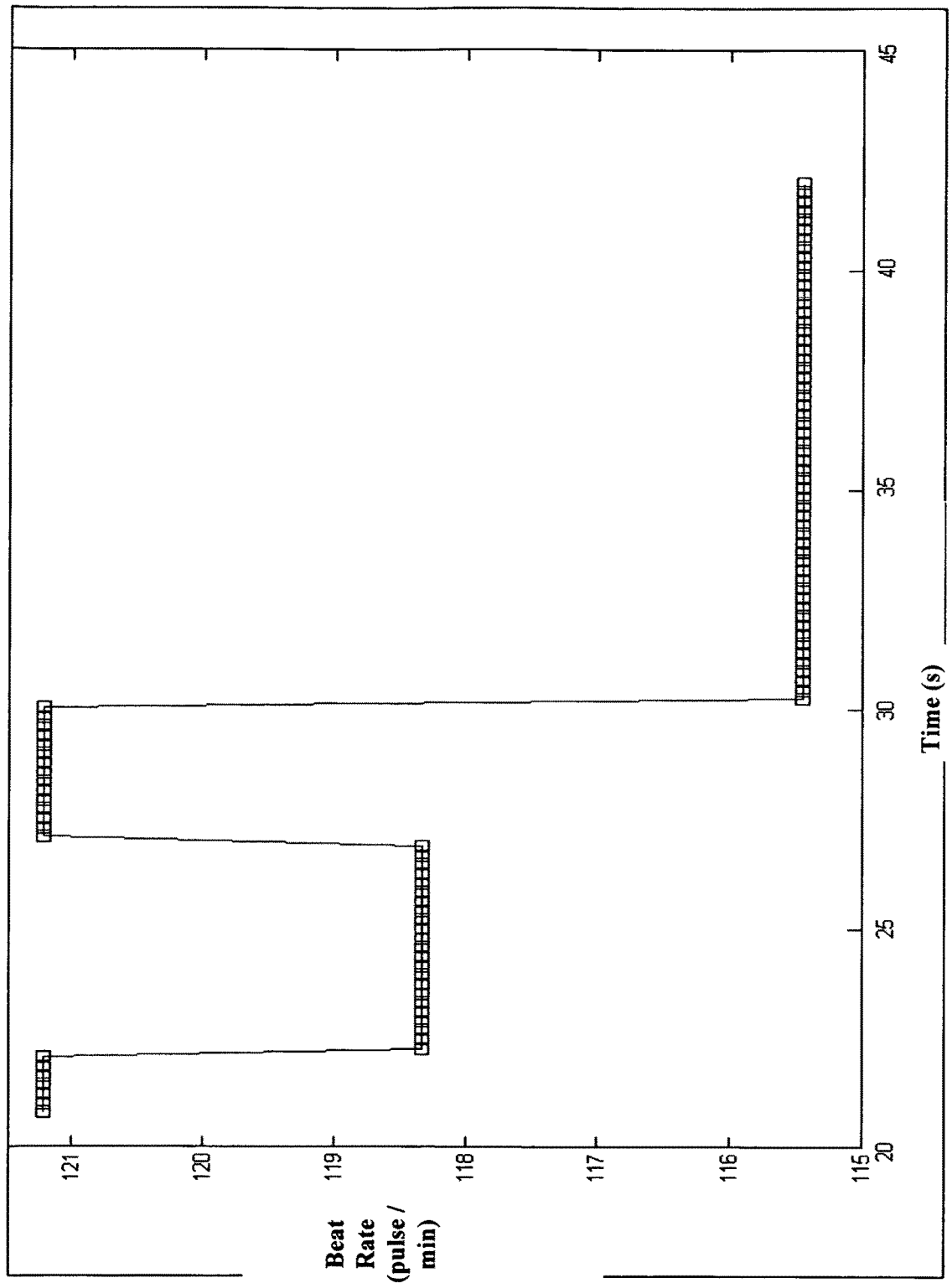

Another method to derive or count the beating rates of cardiomyocytes is to perform a detailed signal analysis to derive the frequency components of the cell index curves and to derive the magnitude of each frequency components. One method of signal analysis is Fourier transform of the cell index curve (of the time domain). Like above method, the sampling time-resolution needs to be sufficiently high so that each beat of the cells has at least three time points being measured. After performing Fourier transform, we would look for the frequency components having the largest magnitude and such frequency would correspond to, or be very close to, the beating frequency. In addition, for such analysis, giving a fixed sampling time resolution, the more time points sampled for analysis, the more accurate it is for the analyzed beating frequency. FIG. 6A and FIG. 6B shows a pair of cell index curves and the corresponding beat rate based the above described Fourier transform. In FIG. 6A, the cell index curves last from time zero to time 42 seconds. In FIG. 6B, the beating frequency for the traces in FIG. 6A is analyzed using the method described here, i.e., Fourier transform followed by picking up the highest-magnitude frequency component. For each derived frequency data at one time moment in FIG. 6B, cell index data from multiple time points (starting from previous 98 time points plus the time moment of interest) is used for analysis. Thus, the time axis in FIG. 6B starts from about 20 seconds to 42 seconds.

Figure 7A:
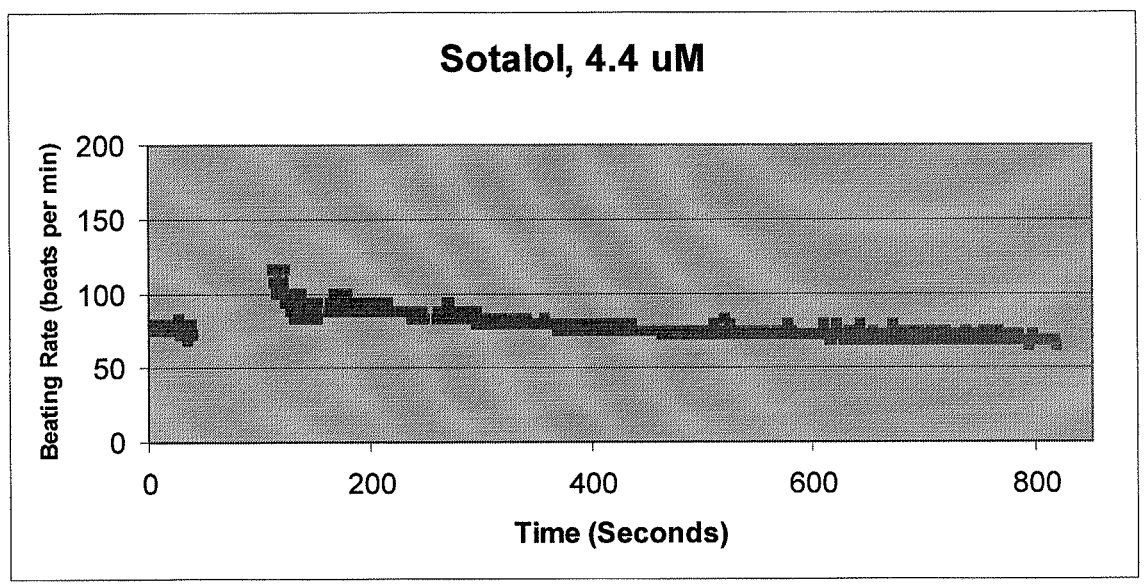
FIGS. 7A and 7B show the beating rate and amplitude, respectively, for the cells before and after the treatment.
Figure 7B:
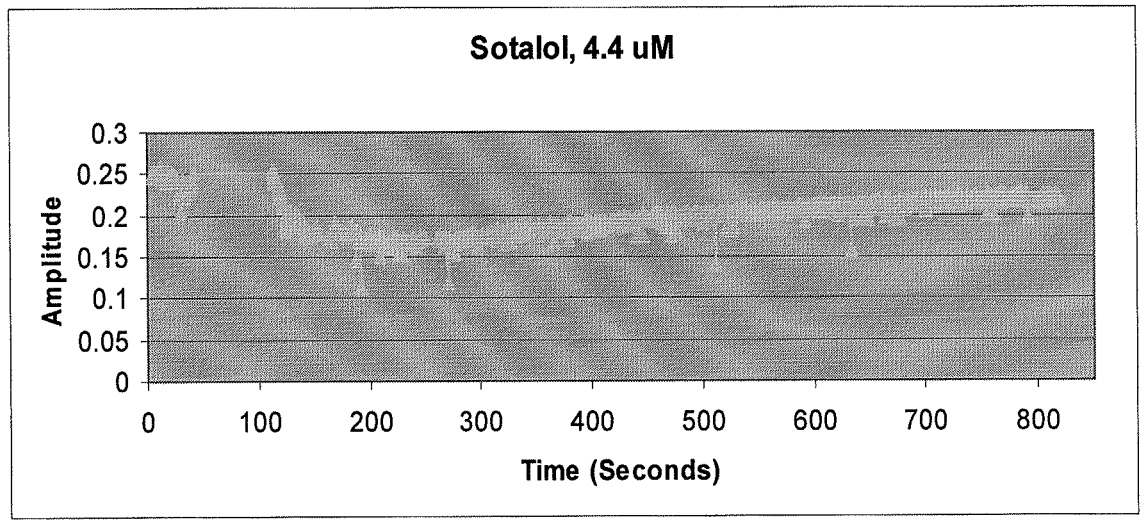
Figure 7C:
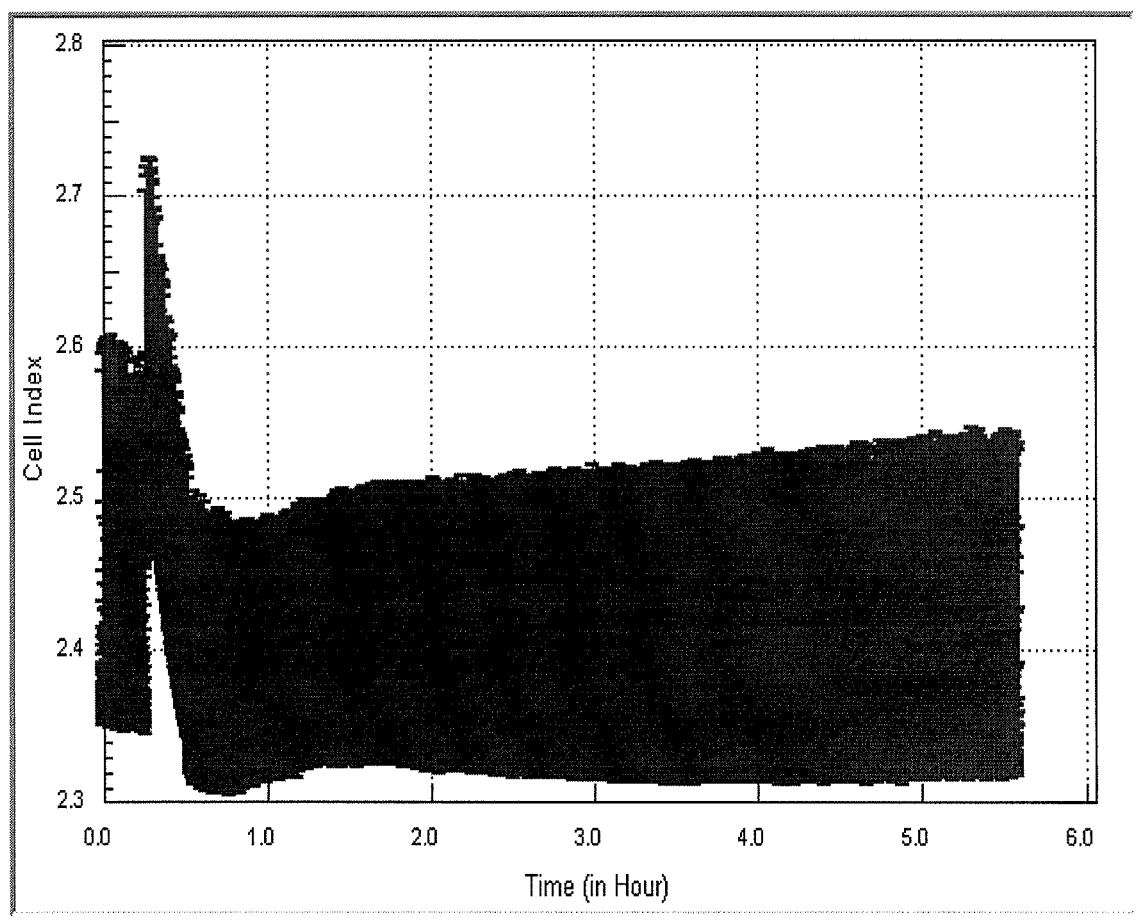
FIG. 7C shows overall cell index curves whilst
Figure 7D:
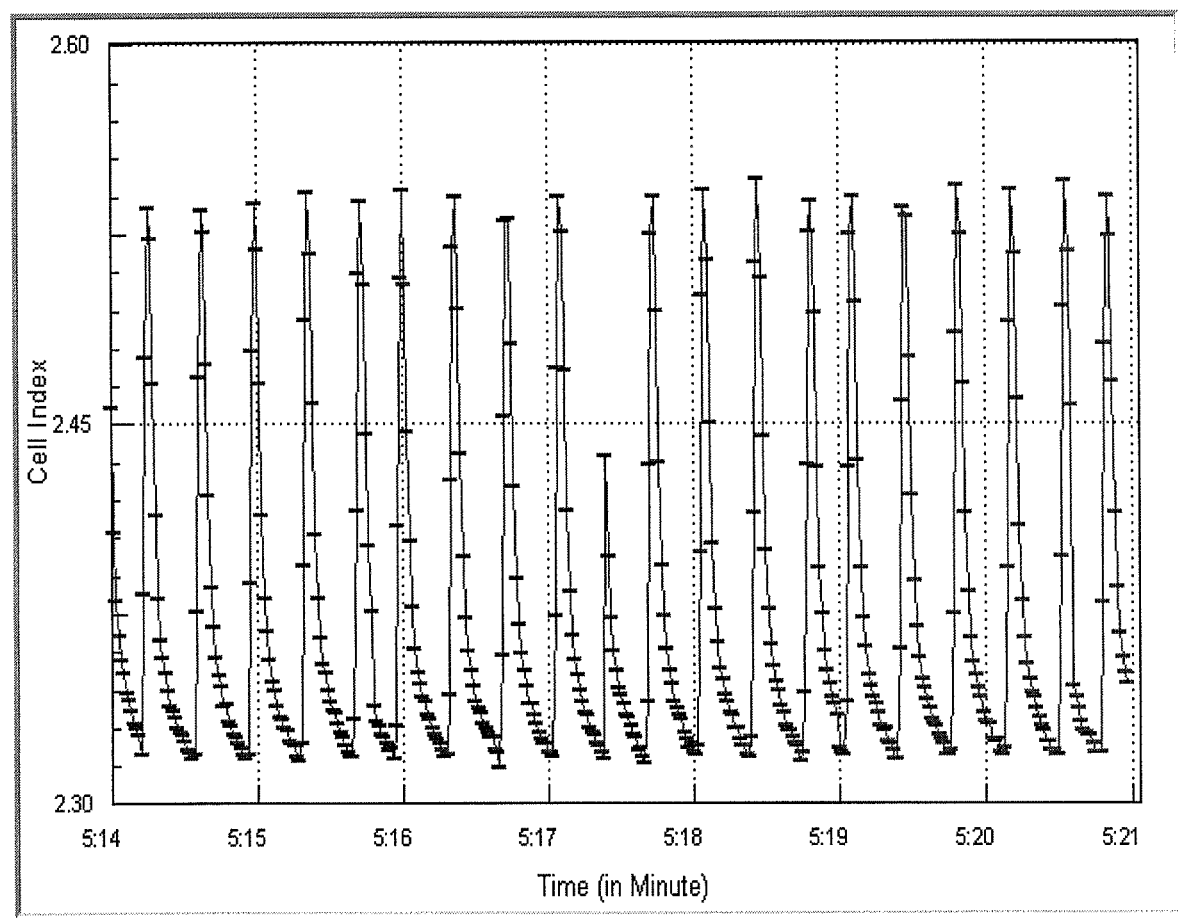
FIG. 7D shows the cell-index based beating curve for a short time period. Note that one second displayed in FIGS. 7C and 7D is equivalent to 40 milli-seconds for real time measurement. The time resolution of the RT-CES measurement for FIGS. 7C and 7D is 40 milli-seconds.

Another method deriving the beating rates of cardiomyocytes is to first determine the time length ($\Delta T$ in seconds) between two consecutive peaks and then calculate the beating rate according to the formula of "beats per minute=60/$\Delta T$". Thus for each two-consecutive peaks, one can calculate one beating rate. Furthermore, one can plot this beating rate as a function of the time (of the first of the two consecutive peaks) to obtain the time dependency of the beating rates. FIG. 7A shows an example of the time-dependent beat rates derived using this method, for mouse ES-derived cardiomyocytes treated with compound sotalol at a concentration of 4.4 uM. Corresponding cell index data is shown in FIGS. 7C and 7D, where the time resolution between two adjacent points is 40 milli-seconds. In other words, a second in FIGS. 7C and 7D is equivalent to 40-milli-second.

For deriving the amplitude of the beating of the cardiomyocytes, there may also be different methods. One method is to analyze each peak and finding the peak maximum and the peak minimum. The amplitude is calculated by subtracting peak maximum by the peak minimum. Then, one can plot the peak amplitude as a function of the time of the peak to obtain the time dependency of the peak amplitude. FIG. 7B shows an example of the time-dependent peak amplitudes derived using this method, for mouse ES-derived cardiomyocytes treated with compound sotalol at a concentration of 4.4 uM. Another approach may also be to use Fourier transform described above. Then based on derived Fourier coefficients, one can re-simulate time domain cell index curves and look for the peak magnitude from the simulated curves For deriving the averaged length of time between the beats, there may also be different methods. For each identified peak, one can first determine a starting point of the peak. Then the time difference between two consecutive peaks at the two starting points of the peak can be used for the length of time between the beats.

With the method of determining each peak, one can also calculate the time-of-rise of the peak and the time-decay-of the peak.

F. Method to Assess the Effect of Known Pharmacological Agents, Proteins, Peptides, Antibodies which Modulate Cardiac Beating Using the Impedance-Measurement System The method described in section E above offers a convenient label-free, real-time and quantitative method for screening of modulators of cardiac function using a fast impedance-measurement system capable of milli-second measurement time resolution. The steps involved in screening for modulators of cardiomyocyte beating using an impedance-measurement system in vitro include:

(1) Provide a single-well or multi-well device that comprise microelectrode arrays in well(s) of the device, which can be used for monitoring cell-substrate impedance.
(2) Optionally coat wells of the device with either fibronectin or other matrix proteins.
(3) Seed either embryonic stem cells (ES cells) of mammalian origin, mammalian adult stem cell-derived cardiomyocytes or primary cardiomyocytes at specific seeding densities to the wells of the device.
(4) Allow the cells to attach and spread.
(5) After a specified period of time unique to ES-derived cardiomyocytes or primary cardiomyocytes, monitor cardiomyocyte beating using the impedance-monitoring system to monitor electrode impedance by using milli-second kinetic readout to resolve the individual beat cycles of the cells. This step should be done immediately prior to addition of pharmacological agent, in order to obtain a baseline of the cardiomyocyte beating frequency using fast measurement software and hardware to ensure milli-second kinetic readout signals.
(6) Addition of the pharmacological agents at one or more doses and continue monitoring the cardiomyocyte beating frequency.

Similar to Section E, the milli-second kinetic readout requires that the impedance measurement system can provide impedance measurement data at milli-second time resolution. In other words, the time difference between two consecutive impedance measurement for a well shall be in the range of milli-seconds (e.g., less than 500 milli-second, less than 300 milli-second, less than 100 milli-second, less than 10 millisecond, or less than 1 millisecond or faster). The milli-second kinetic readout is required to resolve the individual beat cycles of the cells. Thus, the time resolution for the impedance measurement should allow the system to perform measurement at least two time points for each beat cycle, or at more than two points for each beat cycle.

One example of the impedance measurement systems is a fast impedance-measurement system from ACEA Biosciences, where the device is ACEA E-PLATE in the form of microtiter plates whose wells comprise microelectrode structures. The steps involved in screening for modulators of cardiomyocyte beating using the fast impedance-measurement system in vitro include:

(1) Seeding cardiomyocytes, in E-Plates exactly as described in steps 1-4 in section E above for using the system for measurement of cardiomyocytes beating.
(2) Prior to addition of pharmacological agent, obtaining a baseline of the cardiomyocyte beating frequency using the fast kinetic RT-CES hardware and software.
(3) Addition of the pharmacological agents at one or more doses and continue monitoring the cardiomyocyte beating frequency.

Figure 8A:
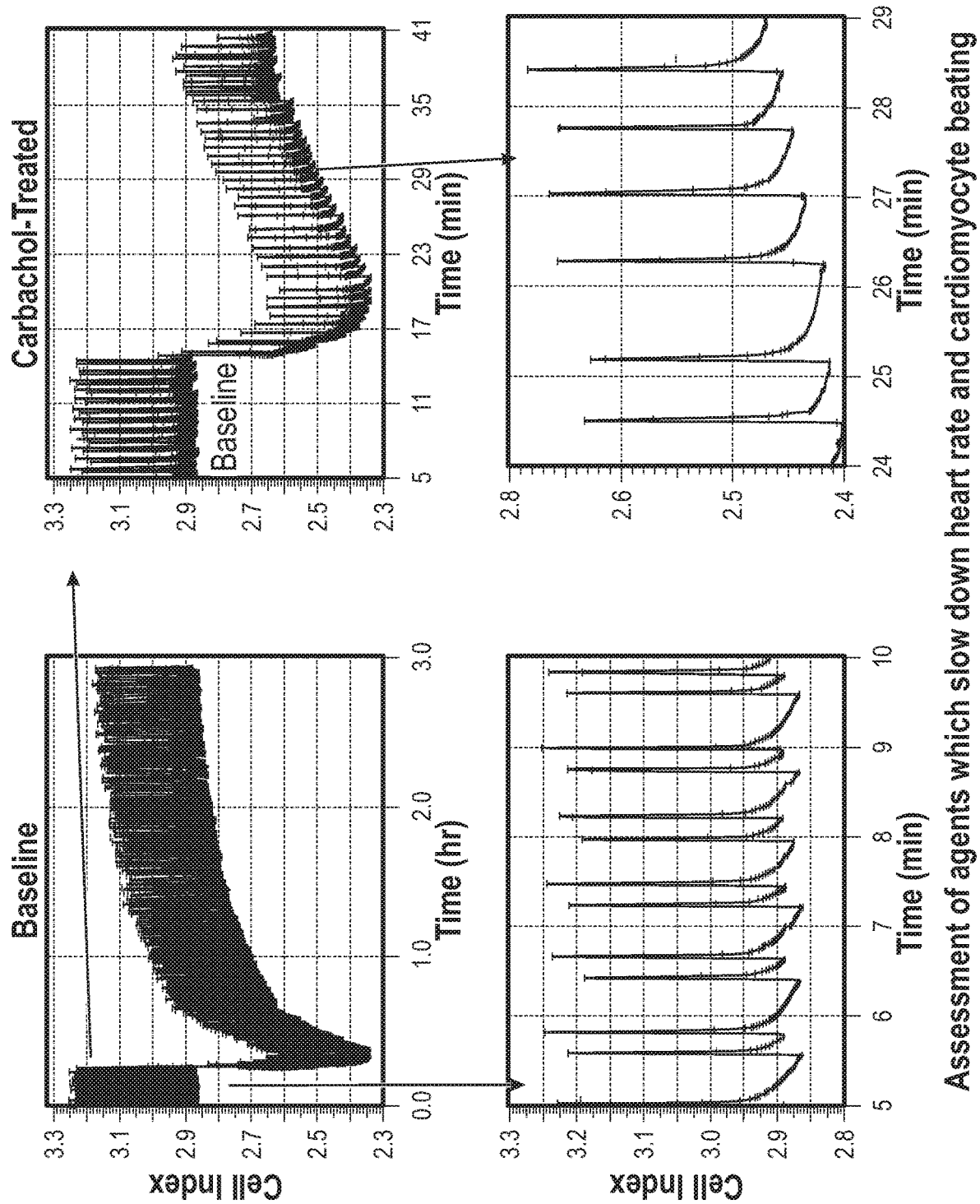
FIGS. 8A and 8B show the detection of cardiomyocyte beating using the ACEA RT-CES system to assess the effect of chemical compound carbachol (333 nM, 8A) and isoproternaol (4.4 uM, 8B) on the beating of cardiomyocyte. Note that one second displayed in FIGS. 8A and 8B is equivalent to 40 milli-seconds for real time measurement. The time resolution of the RT-CES measurement for FIGS. 8A and 8B is 40 milli-seconds.
Figure 8B:
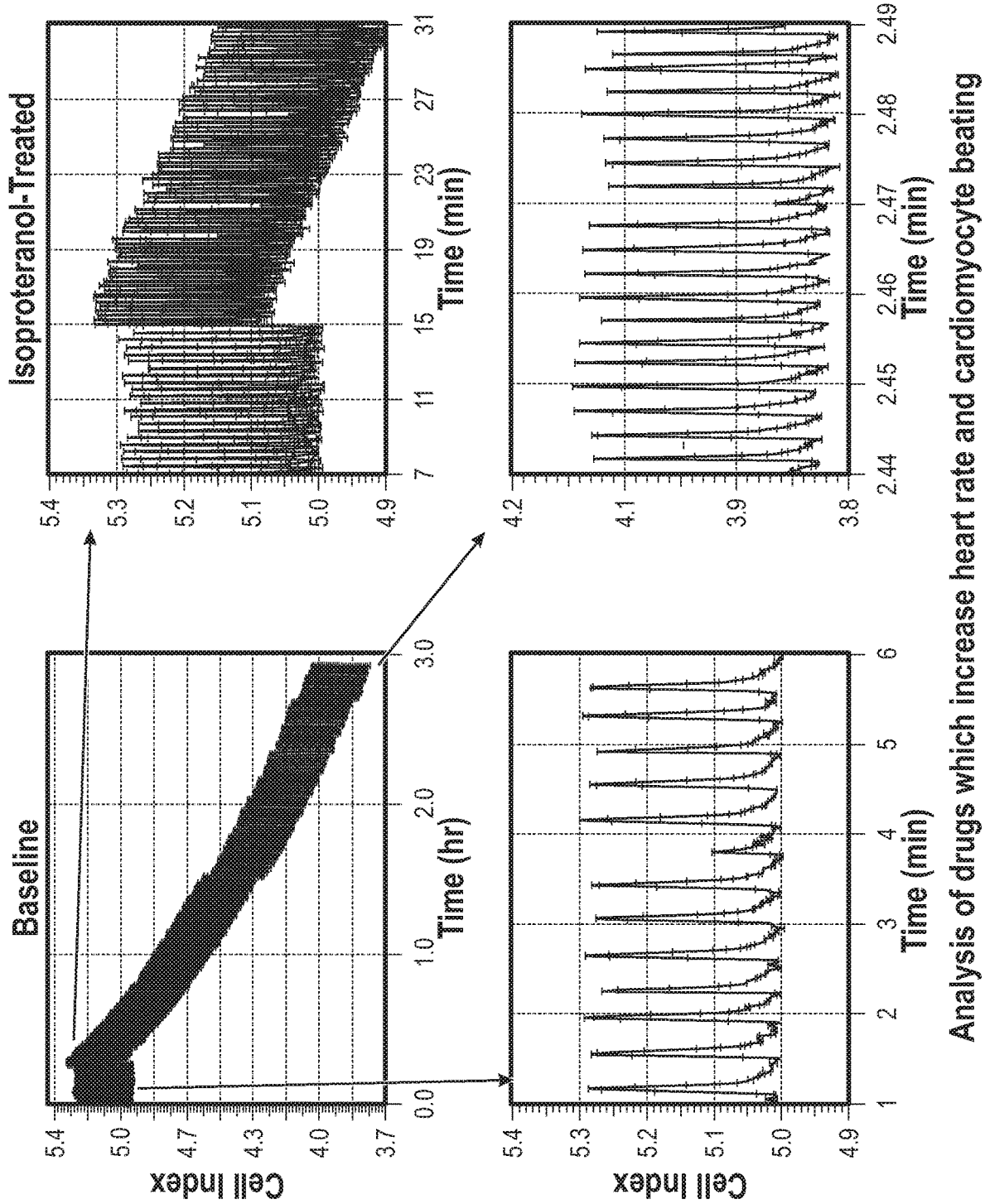
Figure 9A:
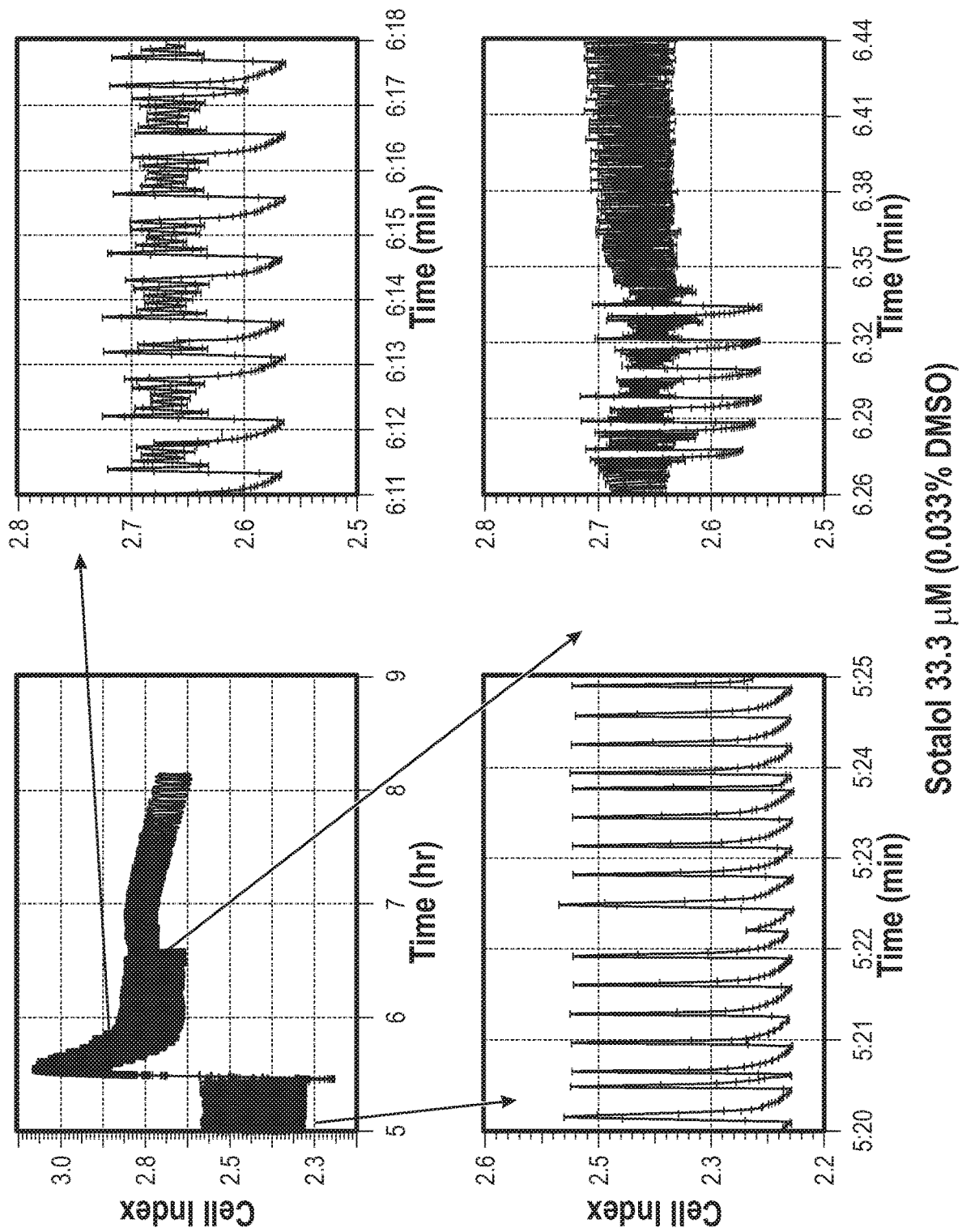
FIGS. 9A-S show the detection of cardiomypcyte beating using the ACEA RT-CES system to assess the effect of various chemical compounds on the beating of mouse ES-derived cardiomyocytes: (9A) 33.3 uM sotalol with 0.033% DMSO; (9B) 400 nM Astemizole with 0.004% DMSO; (9C) 200 nM terfenadine with 0.065% DMSO; (9D) 13.3 uM Erythromycin with 0.13% DMSO; (9E) 20 uM moxifloxacin with 0.3% DMSO; (9F) 20 uM pentamidine with 0.2% DMSO; (9G) 4.4 uM amitripyline with 0.04% DMSO; (9H) 130 nM verapamil with 0.0013% DMSO; (9I) 13.3 uM rosiglitazone with 0.13% DMSO; (9J) 13.3 uM rofecoxib; (9K) 4.4 uM celecoxib; (9L) 40 uM doxorubicin with 0.4% DMSO; (9M) 13.3 uM cyclosporine with 0.13% DMSO; (9N) 4.4 uM propranolol with 0.04% DMSO; (9O) 9.1 nM E4031; (9P) 8 uM DDT with 0.08% DMSO; (9Q) 8 uM PCB with 0.08% DMSO; (9R) 8 uM endosulfan with 0.08% DMSO; (9S) 0.13% DMSO.
Figure 9B:
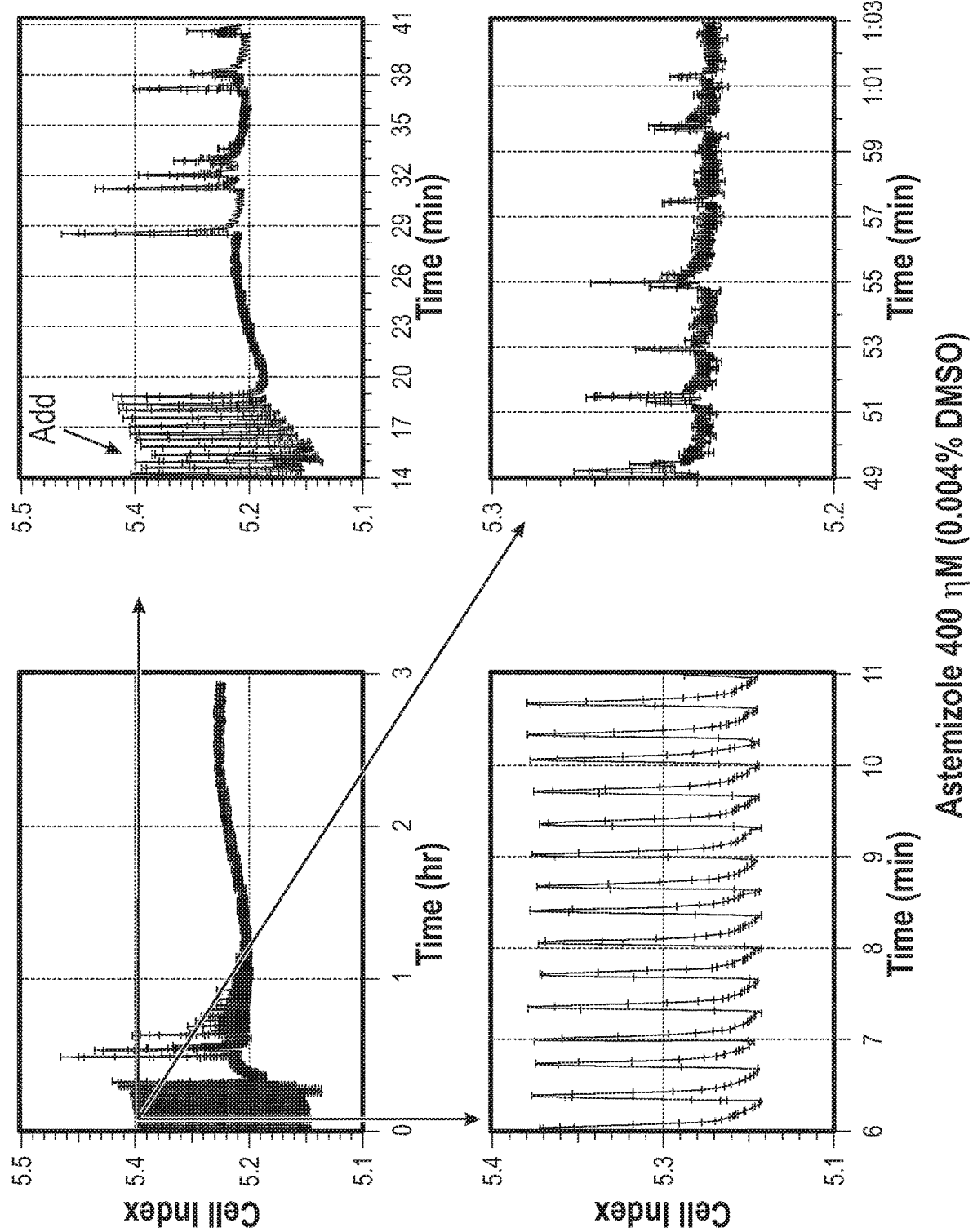
Figure 9D:
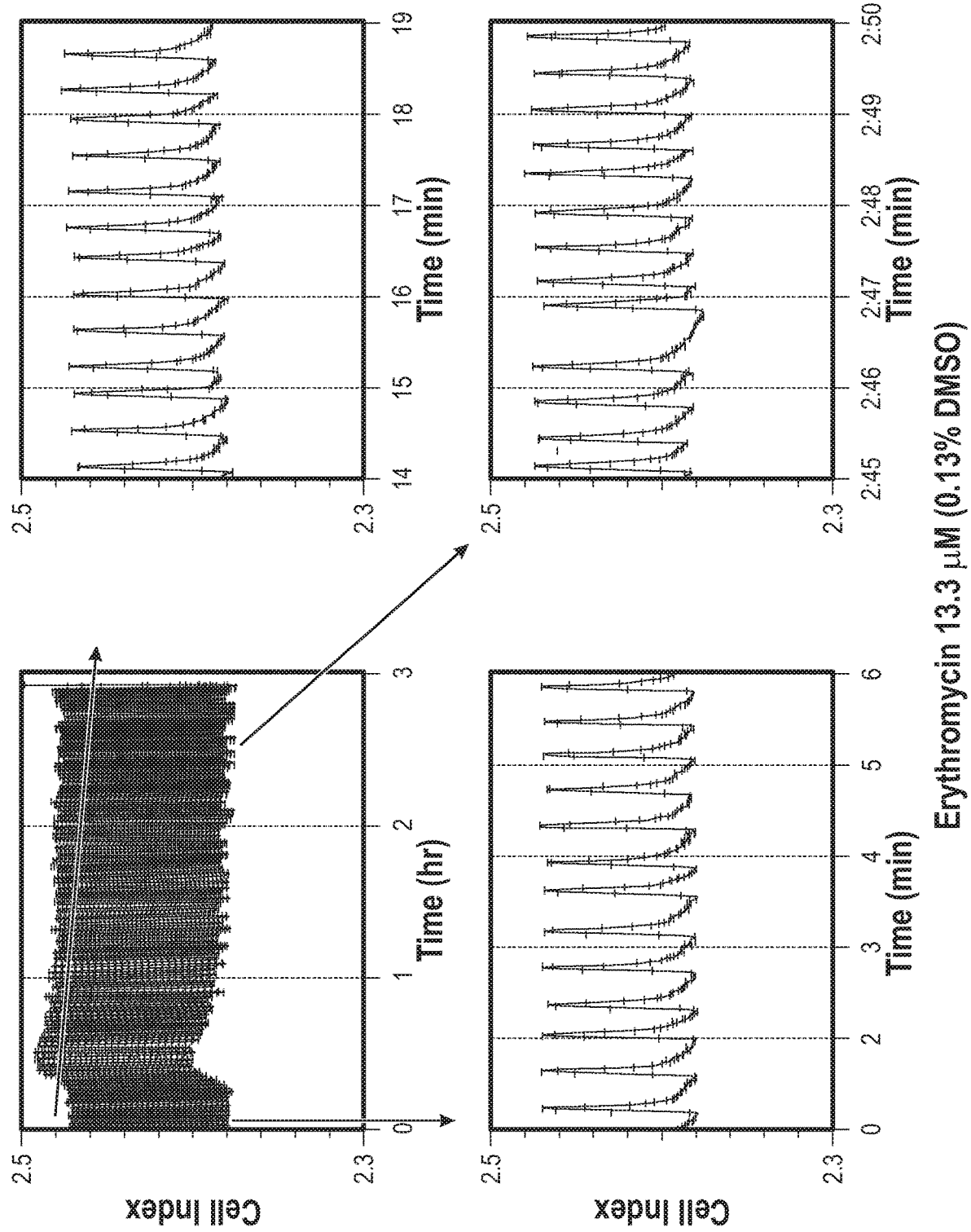
Figure 9E:
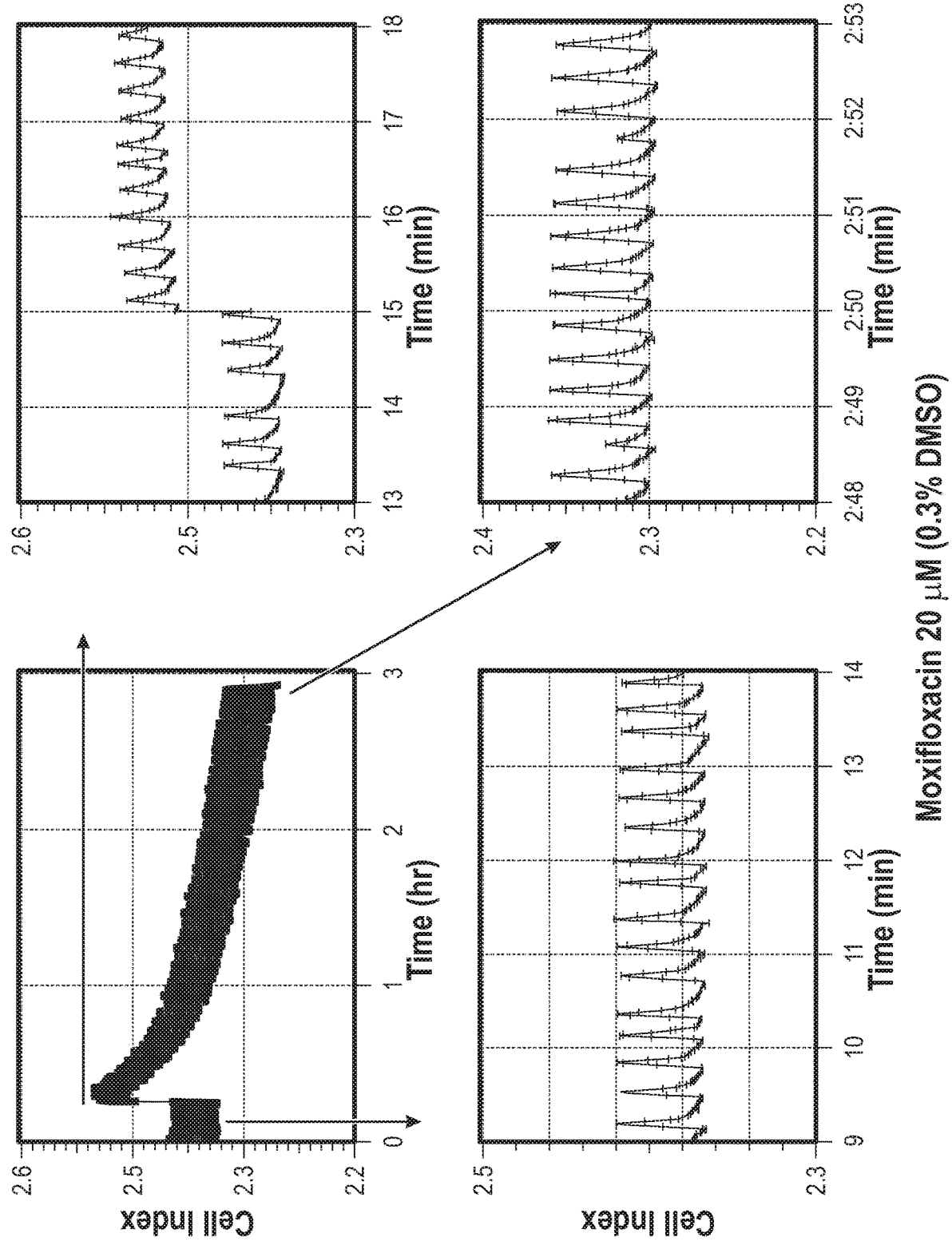
Figure 9F:
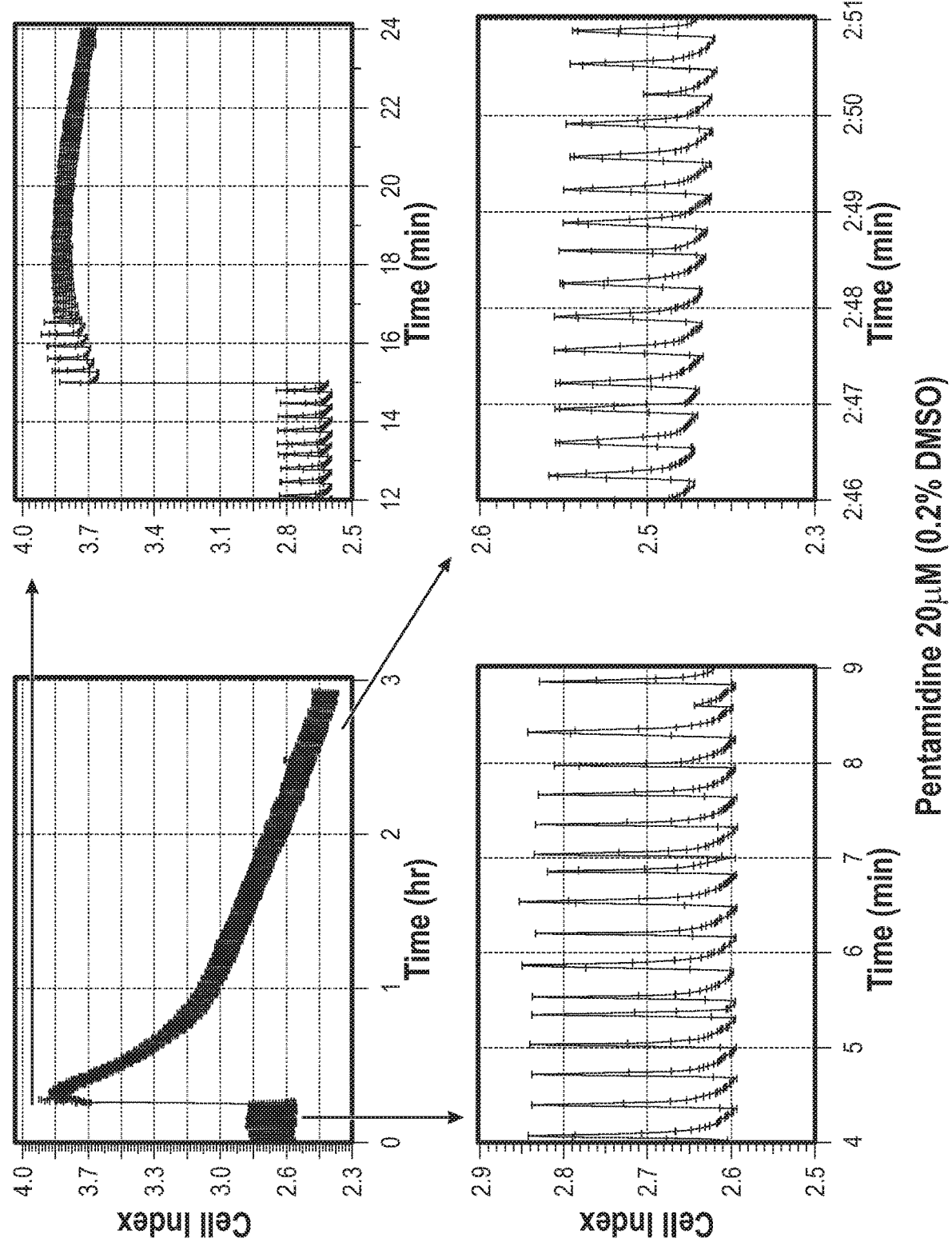
Figure 9G:
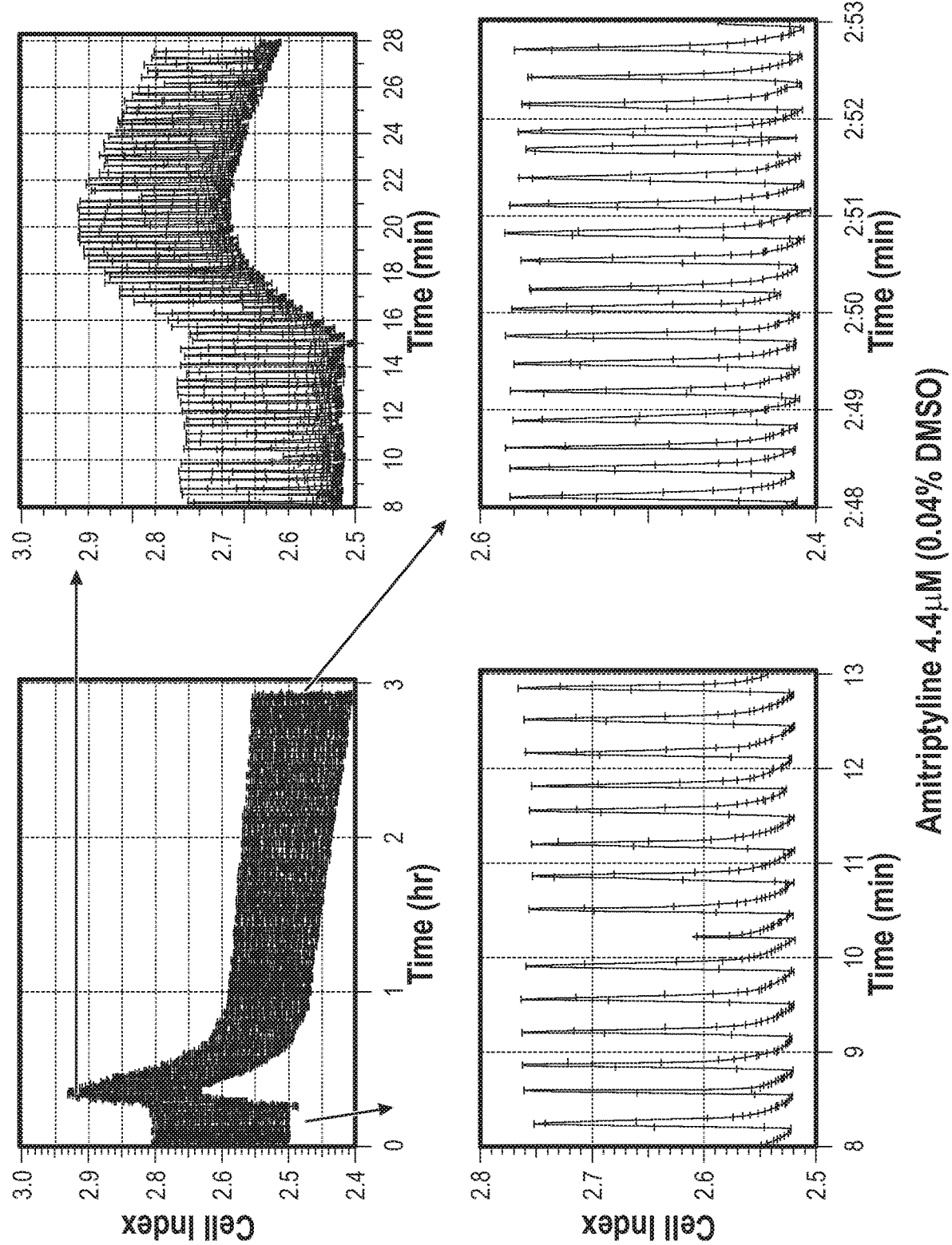
Figure 9I:
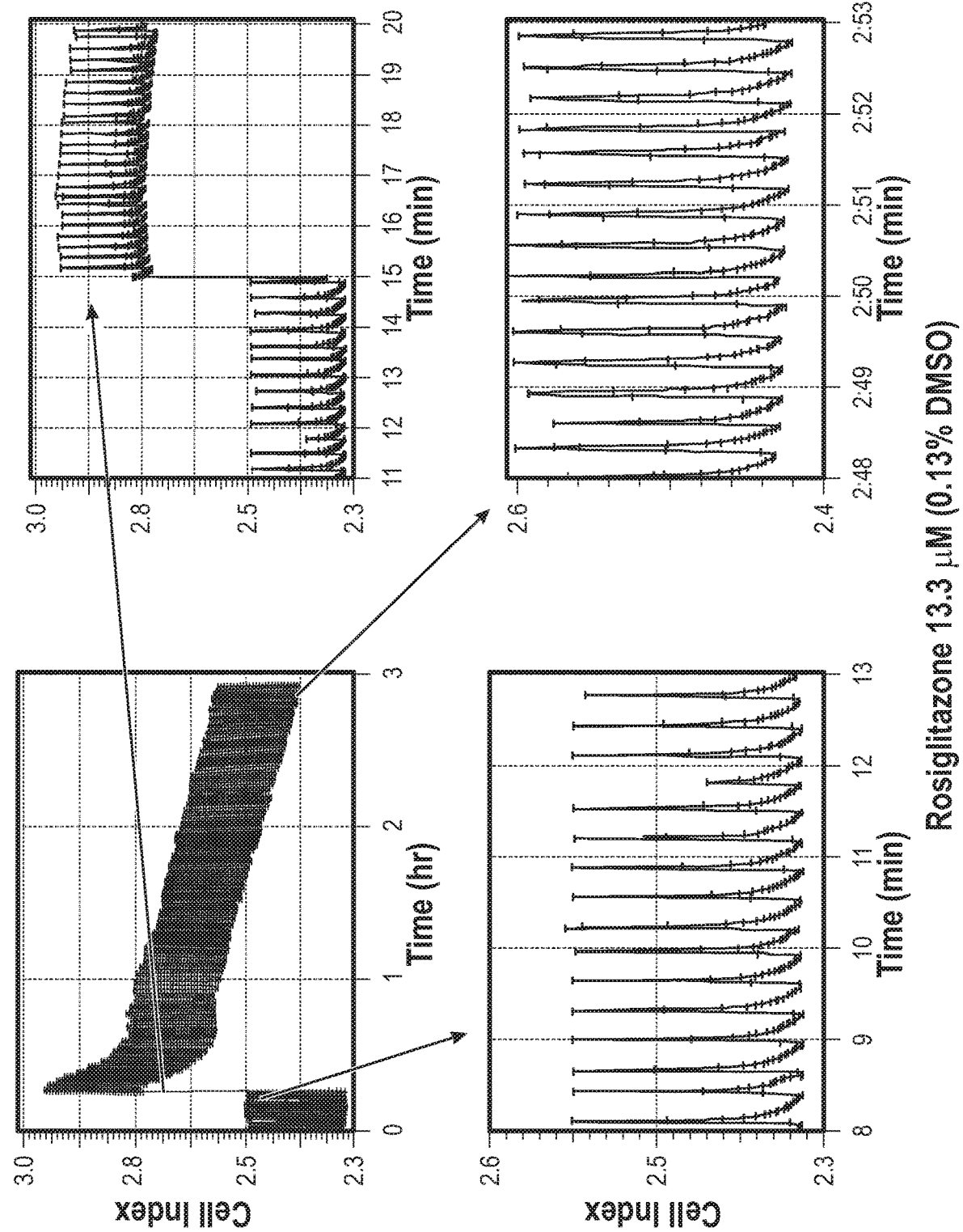
Figure 9M:
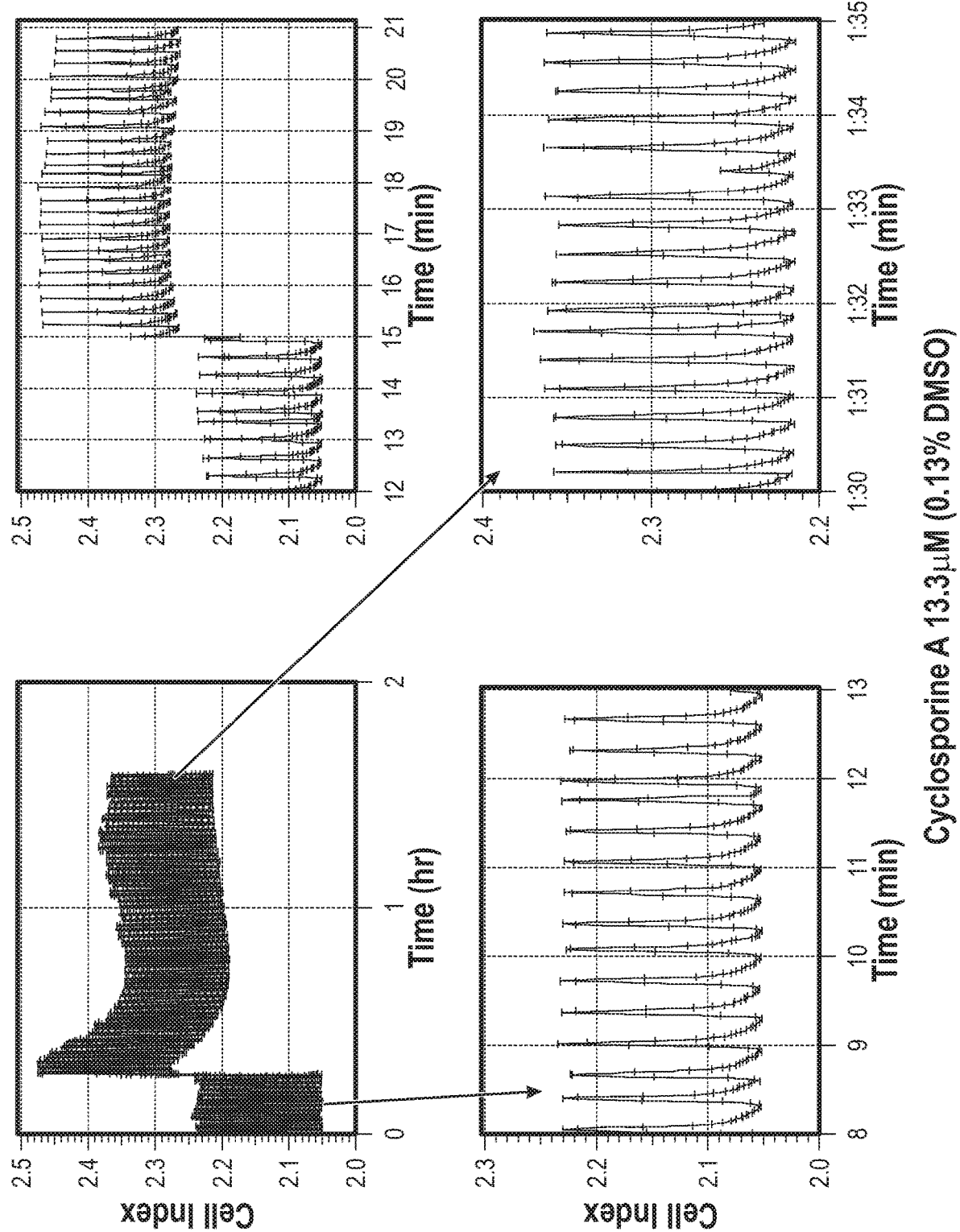
Figure 9N:
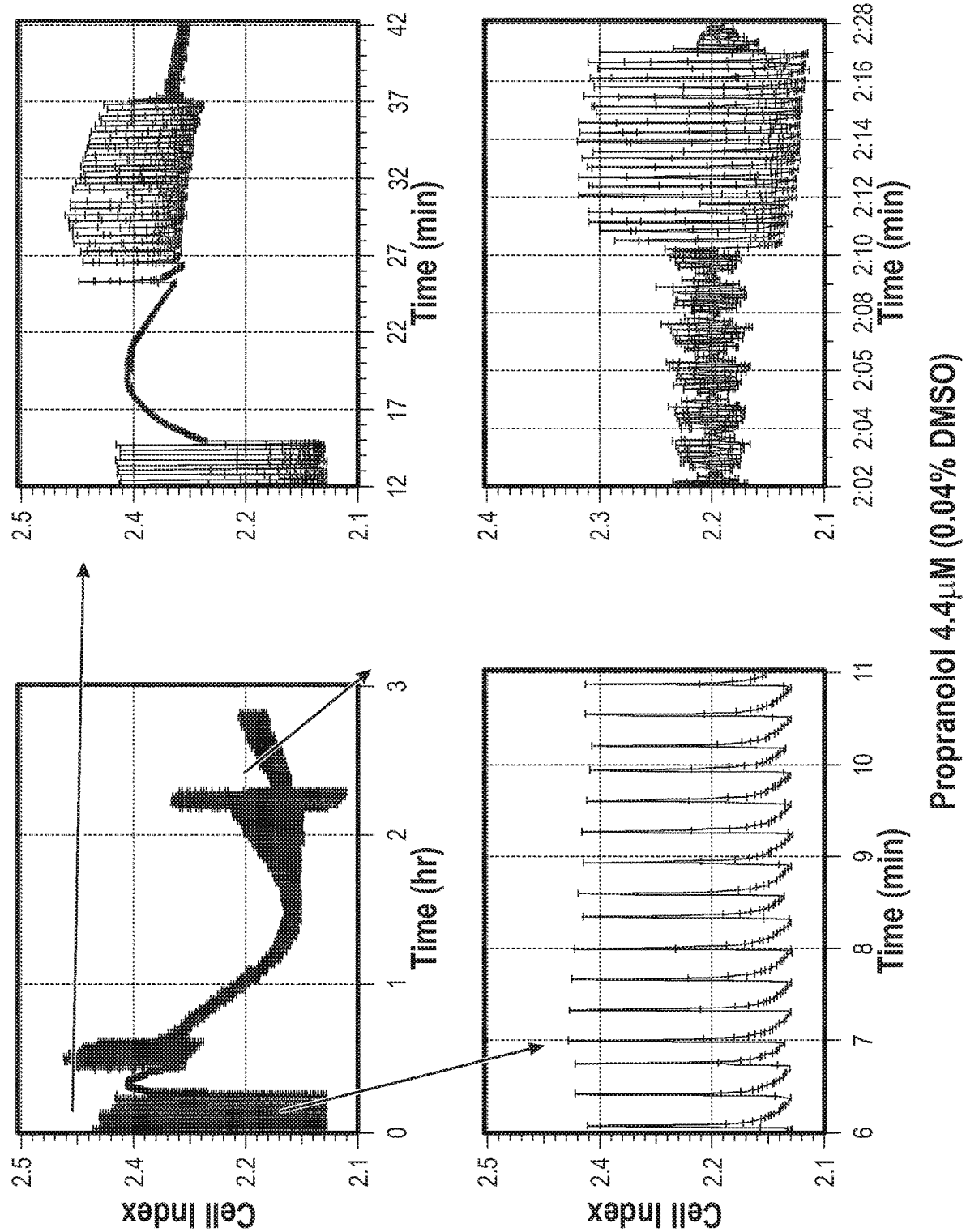
Figure 90:
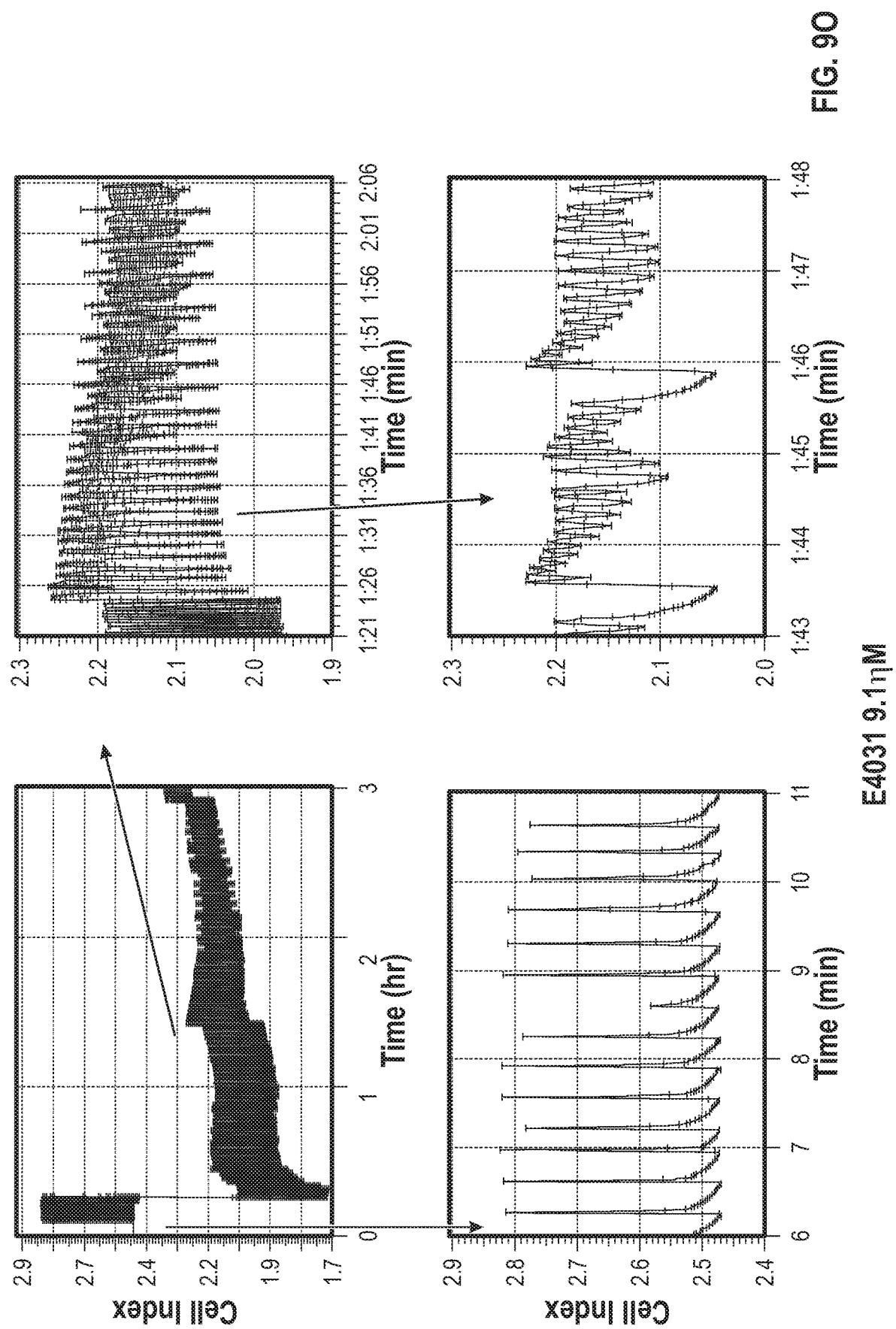
Figure 9P:
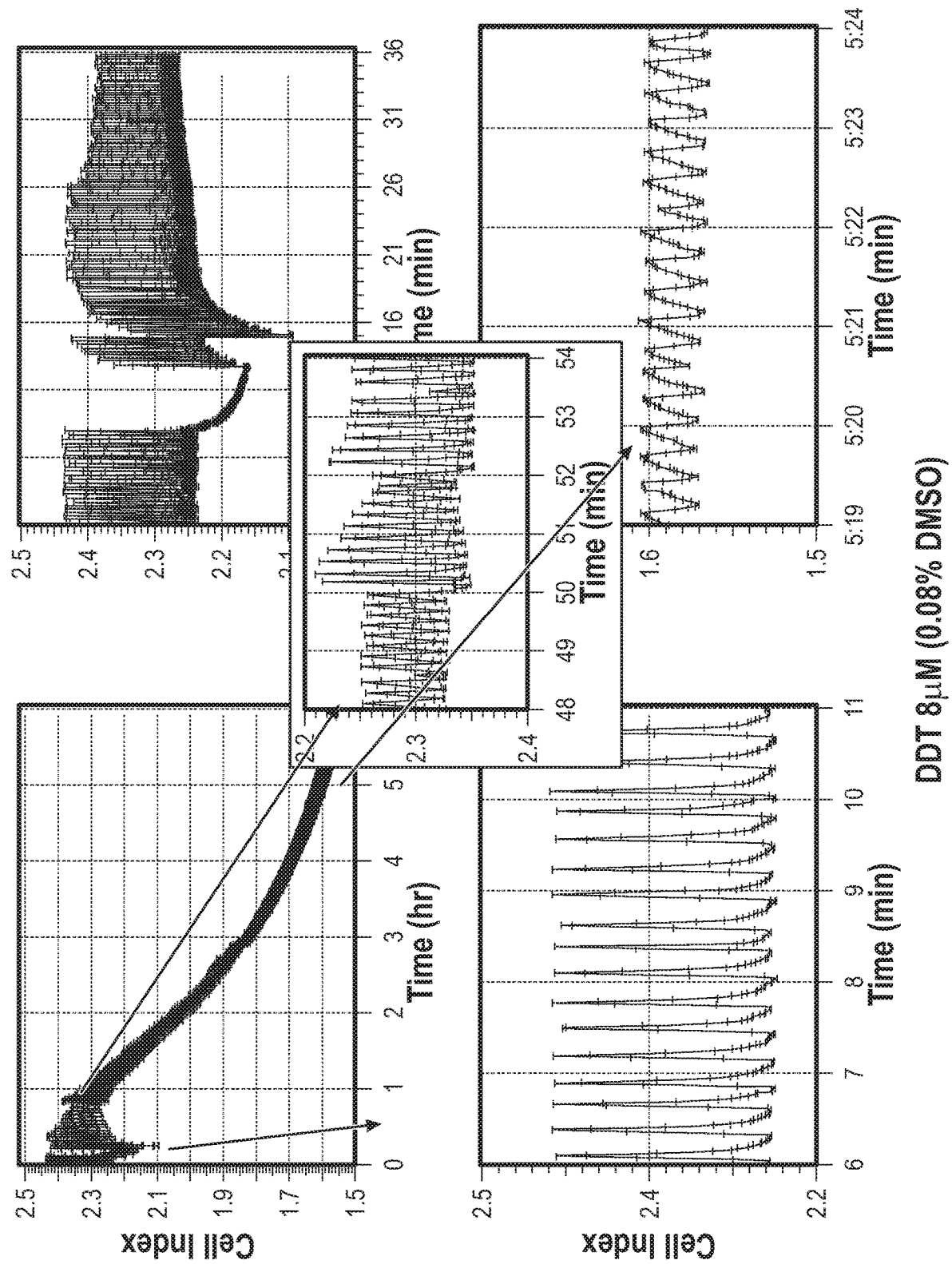
Figure 9S:
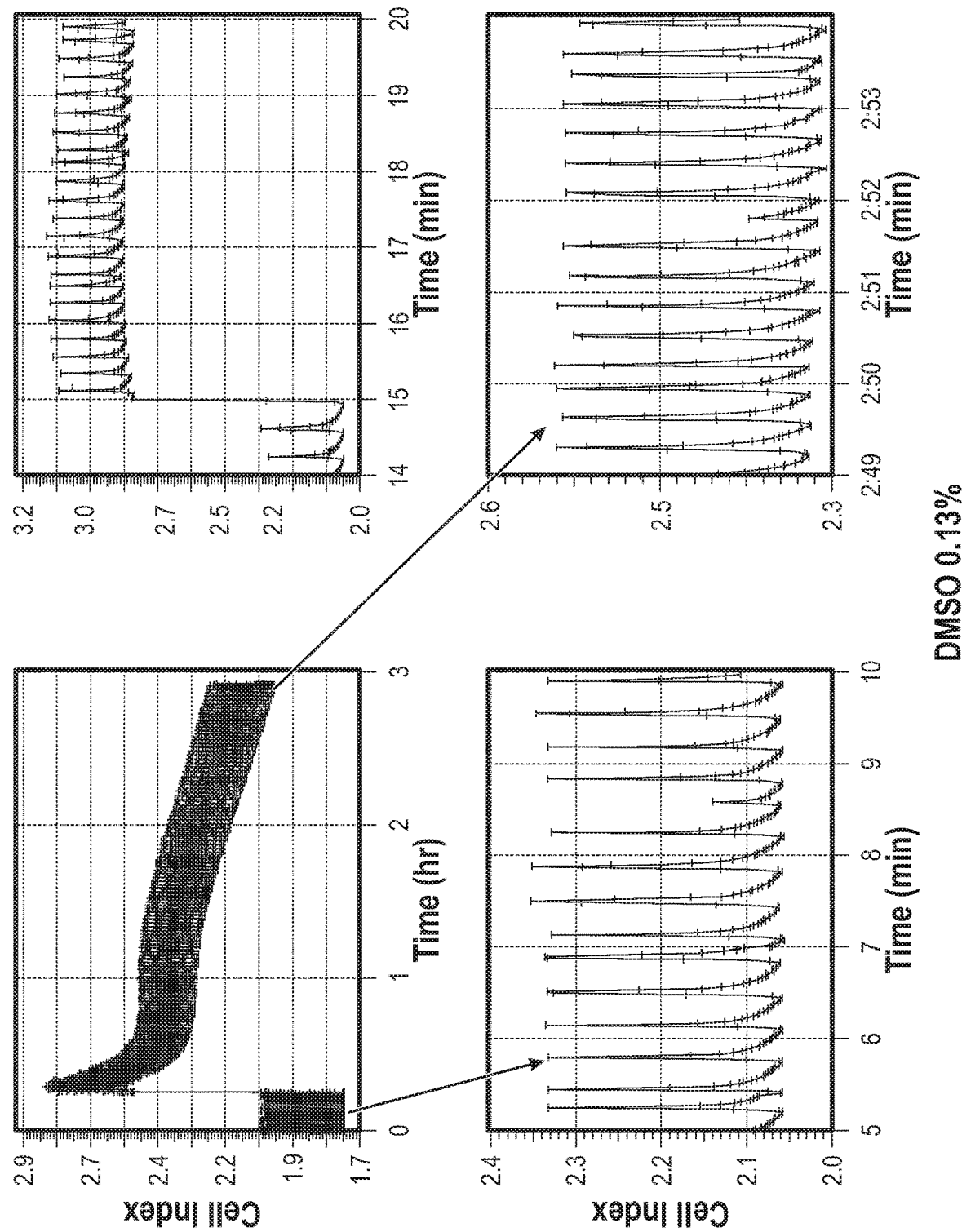

In order to demonstrate the utility of the millisecond kinetic measurements, we first used two pharmacological agents, one known to suppress the heart rate and consequently cardiomyocyte beating and the other known to increase the heart rate and consequently the rate of cardiomyocyte beating. As Mouse ES cells were seeded in FN-coated E-PLATES and monitored for about 72 hours when the cells differentiated into beating cardiomyocytes, as described in Section E. A baseline of the cardiomyocyte was taken for approximately 40 seconds using the specially designed fast kinetic data acquisition hardware and software which is capable of millisecond data acquisition and display. An agonist of muscarinic receptors, carbachol, which is known to slow down the heart rate was added to one well at a final concentration of 333 nM and cardiomyocyte beating was monitored for 10 minutes (FIG. 8A). The data clearly shows that carbachol significantly slows down the rate of cardiomyocyte beating from ~80 beats/min prior to carbachol addition to ~60 beats/min after carbachol addition (Table I). Alternatively, addition of isoproteranol at a final concentration of 4.4 uM significantly increased the rate of cardiomyocyte beating from ~65 beats/min to 115-135 beats/min (FIG. 8B and Table I). These data clearly show that the readout system and the fast kinetic software are sufficiently robust and sensitive to detect these changes in rate of cardiomyocyte beating even at very low compound concentrations. Similar to the cell index plot shown in FIGS. 7C and 7D, the time resolution between two adjacent points in FIGS. 8A and 8B is 40 milli-seconds. In other words, a second in FIGS. 8A and 8B is equivalent to 40-milli-second.

TABLE I

| Compound | Mechanism | Concentration | Beat Rate | Amplitude | Pattern Change |
|---|---|---|---|---|---|
| Carbachol | Muscarnic receptor agonist | 333 nM | From ~80 to ~60 | From 0.07 to 0.06 | Beating rate decreased |

TABLE I-continued

| Compound | Mechanism | Concentration | Beat Rate | Amplitude | Pattern Change |
|---|---|---|---|---|---|
| Isoproteranol | b2 Adrenergic receptor agonist | 4.4 uM | From ~65 to 115-136 | From 0.19 to 0.16 | Beating rate increased |

To further demonstrate the capabilities of the impedance-based monitoring of cardiomyocyte beating in detecting drugs which may adversely affect heart function, a number of drugs which have been pulled out of the market due to cardiotoxic side effects such as ERG channel inhibition and QT elongation were compiled and tested in a dose-dependent manner. The list of these compounds, their mechanism and adverse side affects are shown in Table II. For these tests, mouse ES derived cardiomyocytes were seeded at a final density of 25,000 cells in ACEA E-PLATES and continually monitored by the improved impedance-measurement system. Approximately, 72 hours after cell seeding the fast impedance-measurement system including fast kinetic software and fast measurement hardware circuitry was used to establish a baseline reading of cardiomyocyte beating for each well for about 40 seconds. Subsequently, the cells in each well were treated with the indicated drug and dose shown in FIG. 9. Similar to the cell index plot shown in FIGS. 7C and 7D, the time resolution between two adjacent points in all the figures in FIG. 9 is 40 milli-seconds. In other words, a second in a figure in FIG. 9 is equivalent to 40-milli-second.

Figure 10:
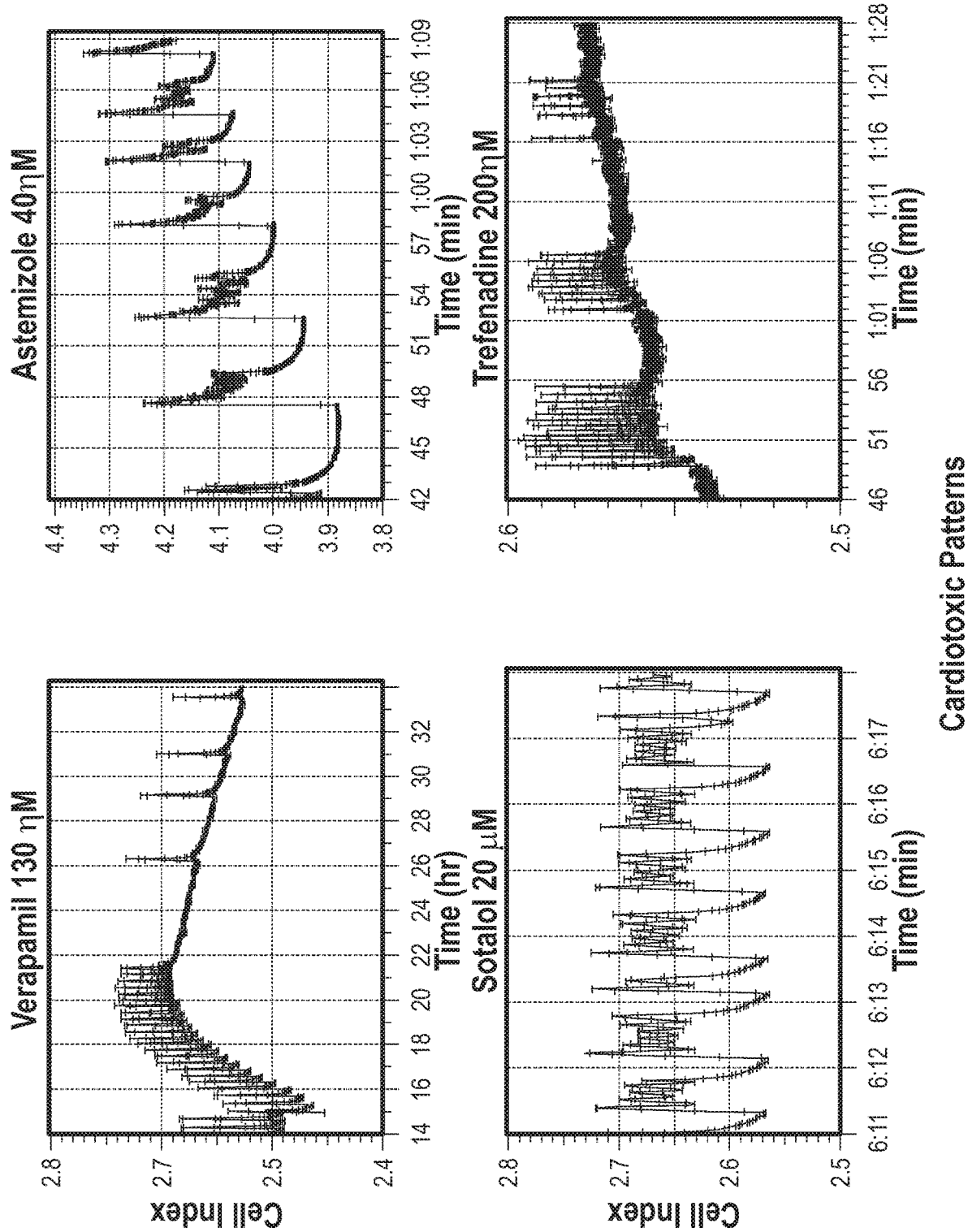
FIG. 10 shows the change of the beating pattern of mouse ES-derived cardiomyocytes as a result of treatment with different compounds as monitored by ACEA RT-CES system. The compounds being tested here include 130 nM verapamil, 40 nM astemizole, 20 uM sotalol; 200 nM trefenadine; 4 uM propranolol; 4 uM celexocib; 150 nM carbachol and 82 nM E4031.

Table II shows a summary of the results, clearly demonstrating that compounds which have been shown to affect ERG channels do affect various aspects of cardiomyocyte beating and function such as frequency of beating, magnitude of beating. Furthermore, as shown in FIG. 10 some of these compounds can lead to qualitatively different or similar patterns. For example, the compounds E4031, Astezimole and dofetilide which are ERG channel inhibitors do contain patterns with similar features. In summary these results clearly indicate that using the fast kinetic software along with the RT-CES system do lead to a sensitive and robust readout for cardiomyocyte beating that can also detect drugs which are known to be cardiotoxic. Similar to the cell index plot shown in FIGS. 7C and 7D, the time resolution between two adjacent points in all the figures in FIG. 10 is 40 milli-seconds. In other words, a second in a figure in FIG. 10 is equivalent to 40-milli-second.

TABLE II

| Compound | Mechanism | Concentration | Beat Rate | Amplitude | Pattern Change |
|---|---|---|---|---|---|
| Astemizole | anti-histamine | 400 nM | 0 | <0.01 | From 68-72 bpm to irregular being to beating stopped |
| Terfenadine | anti-histamine | 200 nM | 0 | <0.01 | From 71-78 bpm to irregular beating to beating stopped |
| Erythromycin | anti-biotic | 13.3 uM | From ~60 to ~80 | 0.09 to 0.07 | No pattern change |
| Moxifloxacin | anti-biotic | 20 uM | From ~80 to ~73 | From 0.055 to 0.060 | No pattern change |
| Pentamidine | anti-infective | 20 uM | From 71~78 to ~71 | From 0.24 to 0.21 | No pattern change |
| Amitriptyline | Serotonergic Inhibitor | 4.4 uM | From ~70 to ~90 | From 0.22 to 0.17 | No pattern change |
| Verpamil | Ca channel blocker | 130 nM | From ~65 to 0 | From 0.13 to 0.06 | From ~65 bpm to only occasional single beating. |
| Rosglitazone | PPAR agonist | 13.3 uM | From ~79 to ~75 | From 0.22 to 0.17 | No pattern change |
| Dofitlite | | 500 nM | From ~80 to ~180 | From 0.09 to 0.02 | Pattern changed, much faster |
| Rofecoxib | COX-2 Inhibitor | 13.3 uM | From ~68 to ~60 | From 0.2 to 0.19 | No pattern change |
| Rofecoxib | COX-2 Inhibitor | 40 uM | From ~62 to ~60 | From 0.16 to 0.10 | Pattern change, no beating after initial treatment, then recovers |
| Celecoxib | COX-2 Inhibitor | 4.4 uM | From ~60 to (~20~~50) | From ~0.2 to ~0.12 | Pattern change |
| Doxirubicin | Anthracycline | 40 uM | ~70 | ~0.16 | No pattern change (initially). Beating pattern changes after 2 hrs. |
| Cyclosporin A | Calcineurin inhibitor | 13.3 uM | From ~70 to ~80 | From 0.18 to 0.15 | No pattern change |
| Propalanol | β2-adrenergic receptor antagonist | 4.4 uM | From ~70 to over 150 | From 0.25 to 0.025 | Pattern changed, much faster and irregular |
| Sotalol | | 13.3 uM | From ~80 to ~160 | From 0.27 to 0.07 | Much faster, pattern changed |

TABLE II-continued

| Compound | Mechanism | Concentration | Beat Rate | Amplitude | Pattern Change |
|---|---|---|---|---|---|
| E4031 | K channel inhibitor | 120 nM | From 80 to 160 | From 0.09 to 0.03 | Pattern changed, much faster |
| DDT | Pesticide | 8 uM | From 80 to 140, then to ~80 | From 0.25 to 0.02 | Initially become faster, later irregular beating |
| PCB | Organic toxicant | 8 uM | From ~65 to o | From 0.2 to 0 | Beating stopped |
| Endosulfan | insecticide | 8 uM | From ~75 to o | From 0.2 to 0 | Beating stopped |

Figure 11:
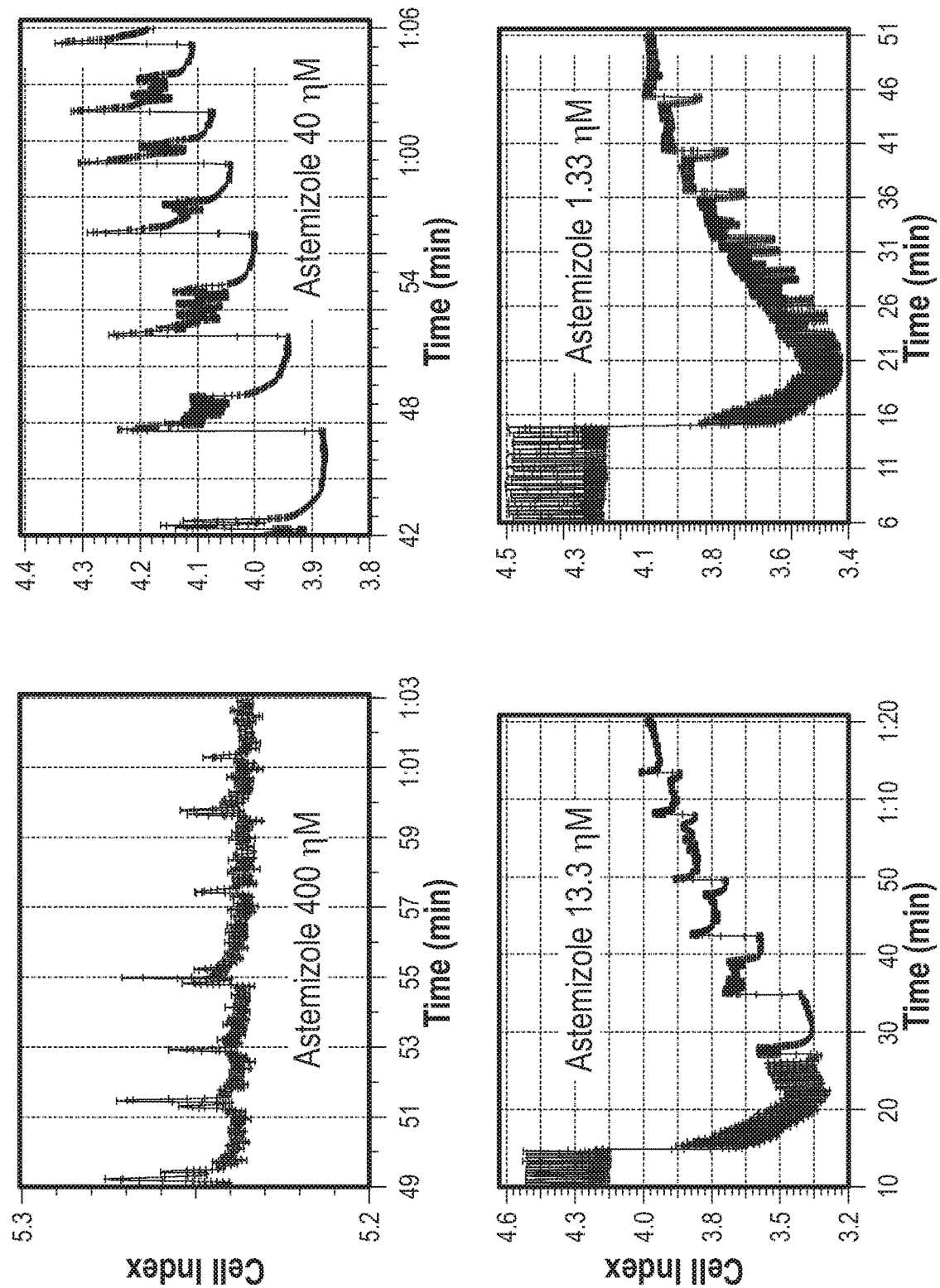
FIG. 11 shows the change of the beating pattern of mouse ES-derived cardiomyocytes as a result of treatment with compound Aztemizole as monitored by ACEA RT-CES system. The compounds concentrations being tested here include 400 nM, 40 nM, 13.3 nM, 1.33 nM, 0.133 nM and 40 µM.

To further demonstrate the capabilities of the impedance-based monitoring of cardiomyocyte beating in detecting drugs which may adversely affect heart function, compounds at different concentrations were tested to demonstrate the dose-dependent effects of these compounds on cardiomyocytes. Approximately, 72 hours after cell seeding the impedance-measurement system including software and hardware capable of milli-second measurement time resolution was used to establish a baseline reading of cardiomyocyte beating for each well for about 40 seconds. Subsequently, the cells in each well were treated with drugs at different dose concentrations. FIG. 11 shows an example of dose dependent effects of Astemizole on cardiomyocytes beating at different concentrations. At high concentration of 400 nM, Astemizole had such a strong effect on the beating of cardiomyocytes that the beating almost stopped. The effect of Astemizole on the beating of the cardiomyocytes is clearly does-dependent. At low concentration of 40 pM, its effect on the beating of the cardiomyocytes is small that the cardiomyocyte beating rate was not affected. Similar to the cell index plot shown in FIGS. 7C and 7D, the time resolution between two adjacent points in all the figures in FIG. 11 is 40 milli-seconds. In other words, a second in a figure in FIG. 11 is equivalent to 40-milli-second.

G. Method to Assess the Developmental and Functional Consequence of Specific Gene Knockout and Transgene Expression in Es-Derived Cardiomyocytes The ES cells offer a suitable experimental model system that is amenable to genetic manipulation. Therefore, specific genes can be targeted in knockout experiment as well as genes can be expressed in a developmental or stage specific manner under the control of special promoters. The impedance-based measurement system can be used to evaluate the role of these genes in cardiac viability, morphology, development and or beating function. The steps involved in assessing the developmental and functional effect of gene knockout or transgene expression include (1) Obtain ES cells harboring specific knockout of genes or which expresses a particular transgene.
(2) Provide a single-well or multi-well device that comprise microelectrode arrays in well(s) of the device, which can be used for monitoring cell-substrate impedance.
(3) Optionally coat wells of the device with either fibronectin or other matrix proteins.
(4) Seed the embryonic stem cells (ES cells) of mammalian origin or adult stem cells of mammalian origin at specific seeding densities to the wells of the device.
(5) Allow the cells to attach and spread and monitor the growth and viability of the cells using an impedance measurement system.
(6) After a specified period of time unique to ES-derived cardiomyocytes or primary cardiomyocytes, monitor cardiomyocyte beating using the impedance-monitoring system to monitor electrode impedance by using milli-second kinetic readout to resolve the individual beat cycles of the cells.
(7) If a particular gene is required for development of cardiomyocytes from ES cells, it is likely that the knockout of that gene will either affect the viability of the cells or block or delay the differentiation of ES cells to cardiomyocytes. Since the impedance-based measurement system is capable of functional monitoring of cardiomyocyte both in long term assays and short term assays, it can be used as a specific way to monitor the effect of either gene knockout or transgene expression on cardiomyocyte function.
(8) Alternatively, the ES cells can be transfected with specific siRNA to "knockdown" the product of a particular transcript and then monitor cardiomyocyte viability, differentiation and function in vitro using the impedance-based measurement system.

Similar to Section E, the milli-second kinetic readout requires that the impedance measurement system can provide impedance measurement data at milli-second time resolution. In other words, the time difference between two consecutive impedance measurement for a well shall be in the range of milli-seconds (e.g., less than 500 milli-second, less than 300 milli-second, less than 100 milli-second, less than 10 millisecond, or less than 1 millisecond or faster). The milli-second kinetic readout is required to resolve the individual beat cycles of the cells. Thus, the time resolution for the impedance measurement should allow the system to perform measurement at least two time points for each beat cycle, or at more than two points for each beat cycle.

One example of the impedance measurement systems is an improved, fast impedance-measurement system from ACEA Biosciences, where the device is ACEA E-PLATE in the form of microtiter plates whose wells comprise microelectrode structures. The steps involved in assessing the developmental and functional effect of gene knockout or transgene expression using the fast impedance-measurement system in vitro include:

(1) Obtain ES cells harboring specific knockout of genes or which expresses a particular transgene.
(2) Follow steps 1-4 of Section D for using the fast impedance-measurement system for measurement of cardiomyocytes function.
(3) If a particular gene is required for development of cardiomyocytes from ES cells, it is likely that the knockout of that gene will either block or delay the differentiation of ES cells to cardiomyocytes. Since the system is capable of functional monitoring of cardiomyocyte, it can be used as a specific way to monitor the effect of either gene knockout or transgene expression on cardiomyocyte function.

(4) Alternatively, the ES cells can be transfected with specific siRNA to "knockdown" the product of a particular transcript and then monitor cardiomyocyte differentiation and function in vitro using the fast impedance-measurement system.

H. Devices and Method for Extracellular Recording

Devices and systems of the present invention permit extracellular recording of cell populations using a variety of technical approaches. Extracellular recording may be performed alone or together with impedance monitoring of cells. As discussed in prior sections, while the present device is suitable for performing extracellular recording of various cells and/or tissues, the present invention is particularly useful for the extracellular recording of cardiomyocyte cells, cardiomyocyte precursor cells, as well as tissues that contains such cells.

The devices and systems of the present invention provide structural configurations that functionally establish cell-free zones to prevent direct interaction between cells and reference electrodes, provide enhanced measurement reliability and accuracy, and bridge the current gap between impedance monitoring and extracellular recording of cells.

For instance, in a first approach, the devices and systems provide a cell-free zone for the positioning of a reference electrode. Accordingly, while traditional systems often require stringent physical parameters for the reference electrode for enhanced measurement, such as stringent tolerances related to surface area, resistance, impedance and the like, present invention provides an alternative solution. Specifically, in one embodiment, a device for performing extracellular recording of cells, such as cardiomyocytes, is provided which includes a nonconductive substrate forming or provided as a base of one or more wells; an extracellular recording electrode positioned on the substrate within the well, wherein the recording electrode is accessible to cells when a cell sample is added to the device; and a reference electrode positioned within the well in a cell-free zone, the cell-free zone is characterized as free from contact with cells when the cell sample is added to the device, thereby preventing contact between cells and the reference electrode. That is, the reference electrode is a cell-free electrode during operation.

Figure 15:
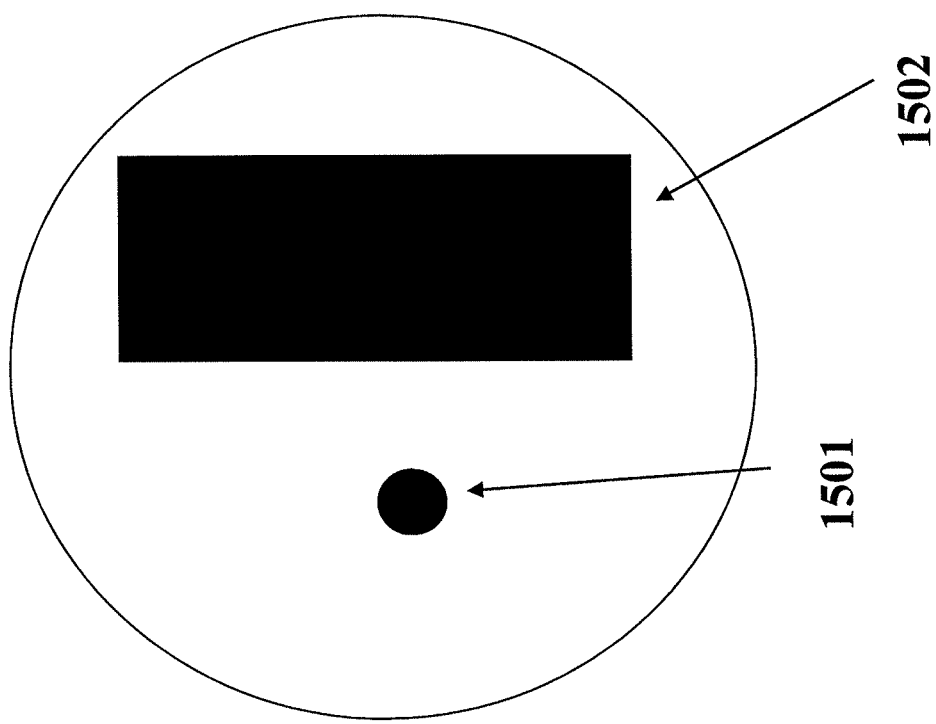
FIG. 15 shows an example of an extacellular recording device where each well of the device comprises a simple, circle-shaped recording electrode and a reference electrode (1501) having large surface area (1502).

Extracellular recording is conducted by amplifying and recording electrical voltage signals between the recording electrodes and reference electrodes. Such electrical voltages are induced on the electrodes as a result of ionic current or movement through cell culture media or solution supporting the cells during the experiment as a result of opening and/or closing of different ion channels across cell membrane during the action potential duration. Generally, it is desirable and it is recognized for the reference electrodes to have small electrode impedances. The small electrode impedance is achieved by using reference electrodes with large effective surface areas by increasing the ratio of the surface area of the reference electrodes to that of recording electrode by a factor of a hundred, even thousands of times. FIG. 15 shows a schematic representation of such electrode pairs placed on a non-conductive substrate, including a small area recording electrode 1501 and a large area reference electrode 1502. For clarity, the connection pads on the substrate for connecting the recording electrode and reference electrode to external circuitry are not shown in FIG. 15. For example, in previous extracellular recording devices, the recording electrodes and reference electrodes are all incorporated onto a substrate surface within a fluid-container well where the recording electrodes are of simple electrode geometry (e.g. circle, or square) having a diameter of 10-100 microns in diameter whereas the reference electrodes would have much larger surface areas.

For the present invention, it is recognized that the extracellular recorded voltage signals are recorded as the difference in the electrical potentials between the recording electrode and reference electrode. In order to achieve improved consistency and reproducibility of the recorded voltage signals, it is desirable to minimize the contribution of any electrical signal from the reference electrode to the recorded voltage signals and to ensure that the majority, if not all, of the recording voltage signals are derived from that on the recording electrode. As mentioned above, the previous extracellular recording devices are designed to this goal by reducing the electrode impedance of the reference electrode through using reference electrode of a large surface area and so minimizing the voltage signals on the reference electrode.

In one aspect, the present invention is directed to a device for extracellular recording of cells, the device comprising: a nonconductive substrate forming a base of one or more wells; a recording electrode positioned on the substrate within the well, wherein the recording electrode is accessible to cells when a cell sample is added to the device; and a reference electrode positioned within the well in a cell-free zone, the cell-free zone characterized as free from contact with cells when the cell sample is added to the device, thereby preventing contact between cells and the reference electrode. In one embodiment, the recording electrode has a diameter from about 10 um to about 200 um. In another embodiment, the recording electrode comprises an electrode structure comprising a plurality of electrode elements. In preferred embodiments, the reference electrode is positioned on the substrate in the cell-free zone.

Now with reference to particular configurations, the device for extracellular recording of the cells is designed and constructed so that the reference electrode is positioned in the well in a cell-free zone so that when the cells are added to the device, the cells would not be in contact with the reference electrode. In comparison with the situation where the cells are in contact with the reference electrode, no-cell-contact with the reference electrode would significantly reduce the contribution of the electrical signals from the reference electrode so that the amplified and recorded voltage signals would mainly come from the recording electrode. Consider the following. When the cells are in contact with the reference electrodes, the ionic current and ionic movement in the regions close to the cells due to the opening and/or closing of ion channels (and/or other ion transporters) in the cell membrane would directly cause an electrical potential signal on the close-by reference electrode since these reference electrodes are in direct contact with the cells. On the other hand, when there is no cell in direct contact with the reference electrode, only the ionic current and ionic movement due to the opening and/or closing of the ion channels in the membranes of other cells may result in small, if any, electrical potential on the reference electrode since these cells are not in contact with the reference electrode. The induced electrical potential on the reference electrode due to such no-contact-cells located at other regions of the wells would be significantly smaller that that induced by the cells in direct contact with reference electrode, because the ionic movement/current in the media would be much smaller in the reference electrode region which is away from the cells.

Figure 33:
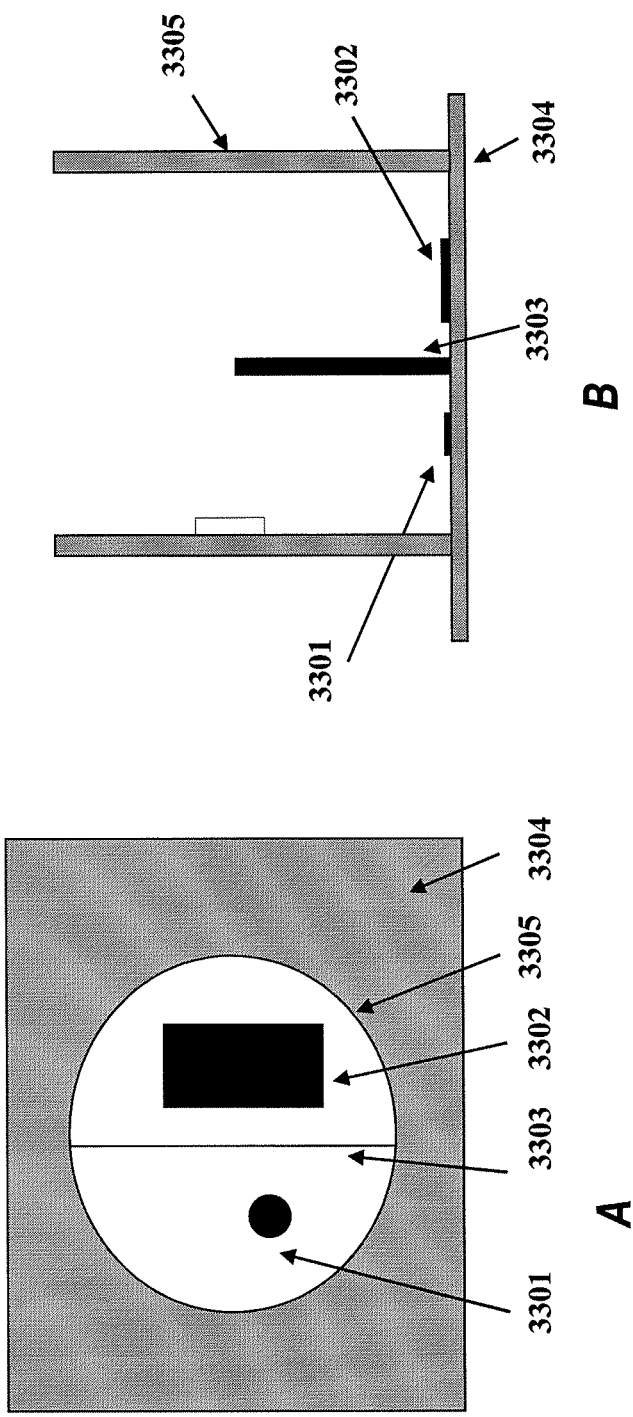
FIG. 33 shows top view and cross-sectional view of a device of the present invention.

There are different approaches to position the reference electrode within the well in a cell-free zone to prevent contact between cells and the reference electrodes. In one embodiment, the reference electrode is positioned on the substrate forming or provided as the base of the wells to which the cells are added. The reference electrode is located in a region that is separated by a barrier from the region containing the recording electrode. Preferably, for the device of the present invention, the reference electrode may be separated by a barrier from the recording electrode so that when the cells are added to the wells containing the recording electrode, the cells will be prevented from landing on and contacting with the reference electrode. When the cells are added to the recording electrode region, the cells are prevented from moving to the reference electrode region and prevented from contacting the reference electrode. Example of this embodiment is shown in FIG. 33 where both top view and cross-sectional view of a device of the present invention are shown. Here, the recording electrode 3301 and reference electrode 3302 are incorporated on the substrate 3304. The barrier 3303 is placed inside the well 3305, separating the recording electrode and reference electrode. In use, the cell culture media (or appropriate solutions for supporting the cells during the experiment) containing the cells is added first to the left half of the well 3305 to the recording electrode region, ensuring that the solution would not overflow above the barrier to the reference electrode. After all the cells settle down to the substrate (which may take some minutes to typically less than an hour), the culture media (or appropriate solutions for supporting the cells during the experiment) not-containing the cells can be added to the right half of the well and sufficient media (or appropriate solutions for supporting the cells during the experiment) is added so that the media would overflow above the barrier, the final media height in the well would be above the barrier and there would be electrical connection path between the recording electrode and reference electrode through the media. Note that for simplicity of the figure, the electrical connection traces for the reference electrode and the recording electrode to the connection pads and the connection pads on the substrate are not shown in FIG. 33. In a related embodiment, the barrier could be provided in a configuration having a series of permeable apertures that selectively permit flow of media while selectively preventing the migration or movement of cells into the cell-free zone; however, such a configuration may lend to clogging of the apertures by blocking cells. In an exemplary embodiment of this approach, the reference electrode may be located under the permeable aperture structure so that the media would flow to the reference electrodes whilst the cells would not.

In another embodiment, the barrier is in a form of a plug that is made of biocompatible materials and can be placed directly above and on the reference electrodes. When the cells are added to the well, the cells are prevented by such a plug to be in contact with the reference electrode and the cells would land on other regions of the substrate, including the recording electrode region. After the cells settle down and adhere to the substrate of the well, the plug is removed and the media or solution in the well would move into the reference electrode region. A complete circuit is formed between the recording electrode and the reference electrode through the media or solution in the well.

Barriers may take alternative forms. For example, barriers may include ledges, walls, troughs and the like to act as a structural or physical barrier to cells. In some instances, a cell repulsive gel is applied to the substrate to define the cell-free zone. The barrier should however permit the medium to contact the reference electrode such that the recording and reference electrode are operably linked through a conductive media. Barriers may be permanently fixed to the device or may be removable as the configuration permits. Similarly, the bather may be formed from any suitable material and have any suitable dimensions consistent with isolating the reference electrode from cells, while obtaining extracellular recording measurements. In some embodiments the barrier is constructed from the same material as the nonconductive substrate. In another embodiment, the reference electrode is positioned on a different plane from the recording electrode, ensuring that the cells added to the recording electrode region would not be in contact with the reference electrode. In such an embodiment the cell-free zone may be a raised surface to prevent cell migration or spreading onto the cell-free zone. In other embodiments an angled surface prevents migration upward along the angled surface and thus provides a suitable cell-free zone towards the top of a slope. In another embodiment, the cell-free zone is a region encapsulated by a porous covering, which permits passage of medium while preventing access by cells.

Figure 34:
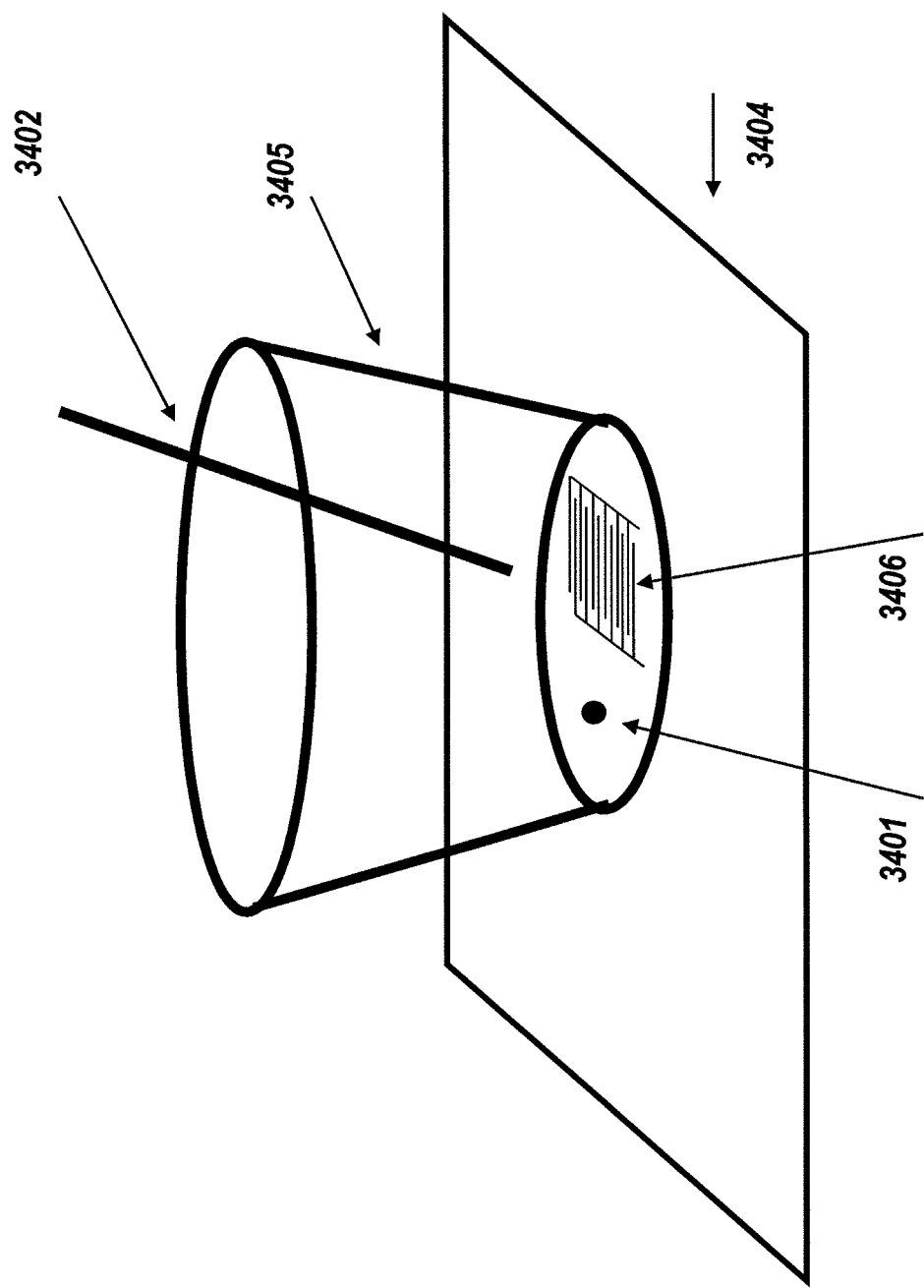
FIG. 34 shows a device of the present invention where the well of the device 3405 comprises a recording electrode 3401 and an interdigitated electrode array 3406 on the substrate 3404, and an external, reference electrode 3402.

In still another embodiment, the reference electrode is an external electrode free from contact with the substrate to which the recording electrode is positioned. For instance, a cell-free zone may be spatially positioned remote from the substrate but within a volume of the well. The schematic representation of such a device is shown in FIG. 34. A recording electrode 3401 is positioned on the substrate 3404. The reference electrode is an external wire electrode (e.g. gold wire, or Silver-silver chloride wire electrode if they are placed into the well for very short time, not causing cytotoxic effects) 3402. In FIG. 34, an impedance electrode array 3406 is also positioned on the substrate 3404. The electrode array 3406 is of straight-line, interdigitated electrode geometry and comprises two electrode structures, each of which comprise multiple electrode elements. In use, when the cells are added to the well 3405 containing the recording electrode 3401 and impedance measurement electrode array 3406, the external reference electrode 3402 can be outside of the well. After the cells are added to the wells and are settled down to the bottom, the external reference electrode 3402 can be added to the well manually or automatically and the reference electrode would not be in contact with the substrate of the well and not be in contact with the cells on the substrate. In some embodiments, the external reference electrode 3402 is fabricated to a lid or cover which may be placed over top of the well.

Thus, a cell-free zone may be spatially positioned away from the substrate. In such a configuration the cell-free zone may occupy a volume of the well that does not contact the substrate, yet does contact medium when added to the device. Accordingly, while cells do not contact the cell free zone, an electrically conductive media may still ensure operable contact between an extracellular recording electrode and a reference electrode.

For extracellular recording, the recording electrode is generally of simple geometry and consists of a single electrode element such as a circle, a square or some other geometry. The size of such recording electrode typically ranges from about 10-30 to about 100 micron in a diameter. Such small electrode geometry has advantages of recording the electrical potential generated by a small number of the cells located on the recording electrodes. Action potentials from such a small number of the cells tend to be synchronized or nearly synchronized, allowing for a better time resolution for recording extracellular potential and for resolving different features of the recorded potential. However, one limitation of such extra-cellular recording is that due to small area of such electrodes, there tends to be large variations in recorded signals between different recorded electrodes of the same geometry in the same wells (if multiple recording electrodes are positioned inside a single well) or different wells. In particular, if insufficient number of the cells is added to the well to cover all the recording electrodes, it is possible that some recording electrodes may not show any recorded signal or only show recorded signals of very small magnitude. Furthermore, depending on exact distribution or locations of the cells on the recording electrodes, different recording electrodes may show significantly different extracellular potential waveforms. For this reason, many existing devices for extracellular recording comprise multiple small-area recording electrodes. Extra-cellular potentials from each such recording electrode are amplified and recorded separately. The user would pick and choose appropriate signal waveforms recorded for some individual recording electrodes for data analysis.

To overcome such a limitation, in some embodiments of the present invention, electrode structures having larger surface areas and including multiple electrode elements are used as recording electrodes. The advantage of recording extracellular potential with such electrode structures is that the extracellular potential is an integration of the potentials from all the cells on the electrode array and would be more reproducible between different wells. The variation in recorded signals between difference electrode structures from different wells would be smaller than that recorded with small, single recording electrode elements. For such devices, each well may comprise a single electrode structure, or two electrode structures. In preferred embodiment, each well comprises a single electrode structure consisting of multiple electrode elements.

Thus, the extracellular recording electrode may be provided in a variety of configurations. In some instances the recording electrode includes a unitary, circular or unbranched configuration. In other embodiments the extracellular recording includes an electrode structure, which itself may include a plurality of electrode elements. Exemplary electrode structure and electrode element configurations may be found in U.S. Pat. Nos. 7,470,533; 4,459,303; 7,192,752; 7,560,269; and 7,468,255, each of which is incorporated by reference. However, the majority of the above listed patents refer to arrays of electrodes having at least two complementary electrode structures. Thus, when considering the configurations for use as an extracellular recording electrode structure or element, the skilled artisan would typically provide one half of the array as set forth in the patents.

Figure 13:
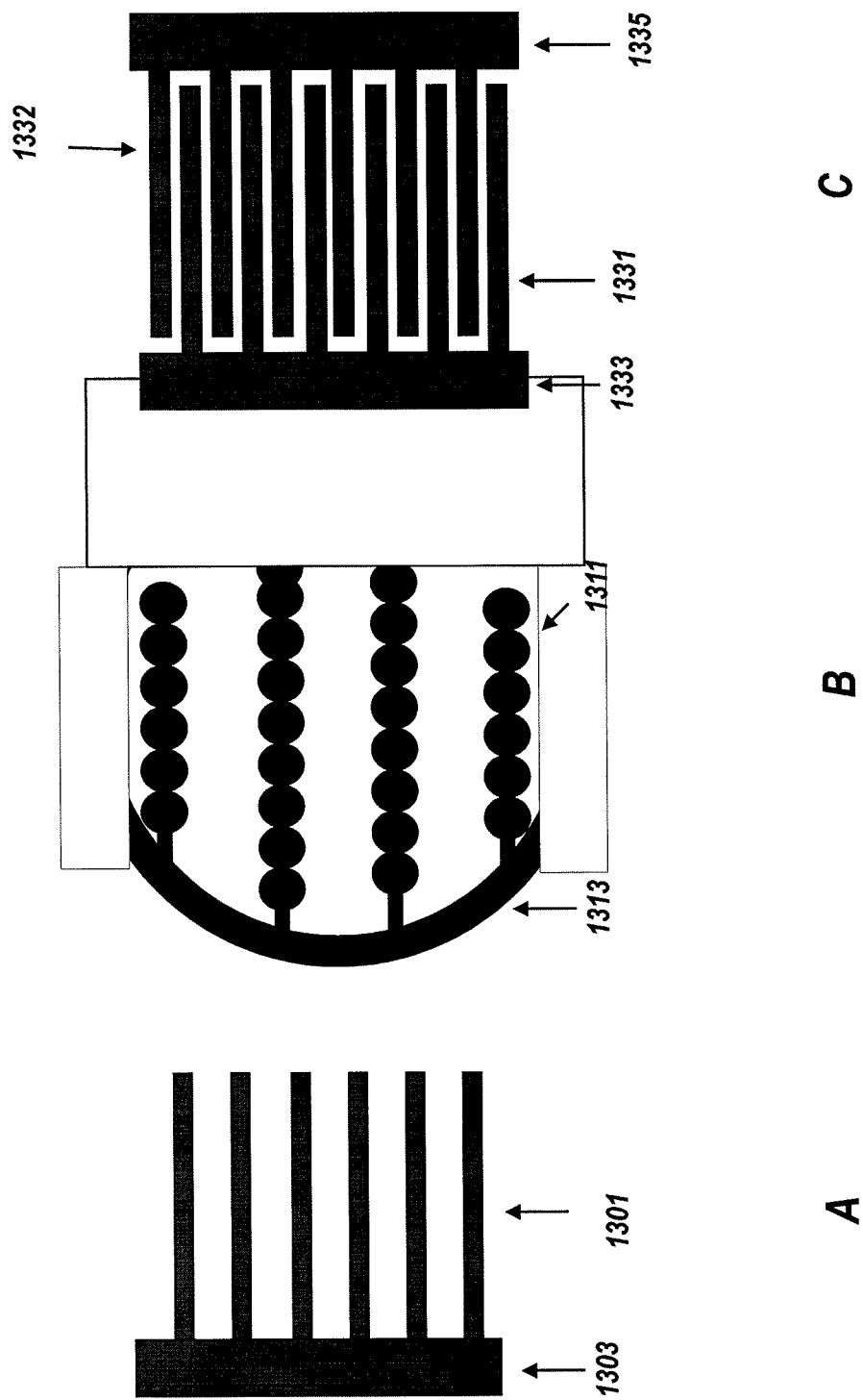
FIG. 13 shows examples of electrode structures having multiple electrode elements that can be used for extracellular recording and/or impedance measurement where 13A, 13B, 13C, 13D, 13E and 13F are the rectangular shape, circle-on-line shape, a complete interdigitated electrode array, sinuosoidal shape, castellated shapes and a complete circle-on-line electrode array, respectively.
Figure 13:
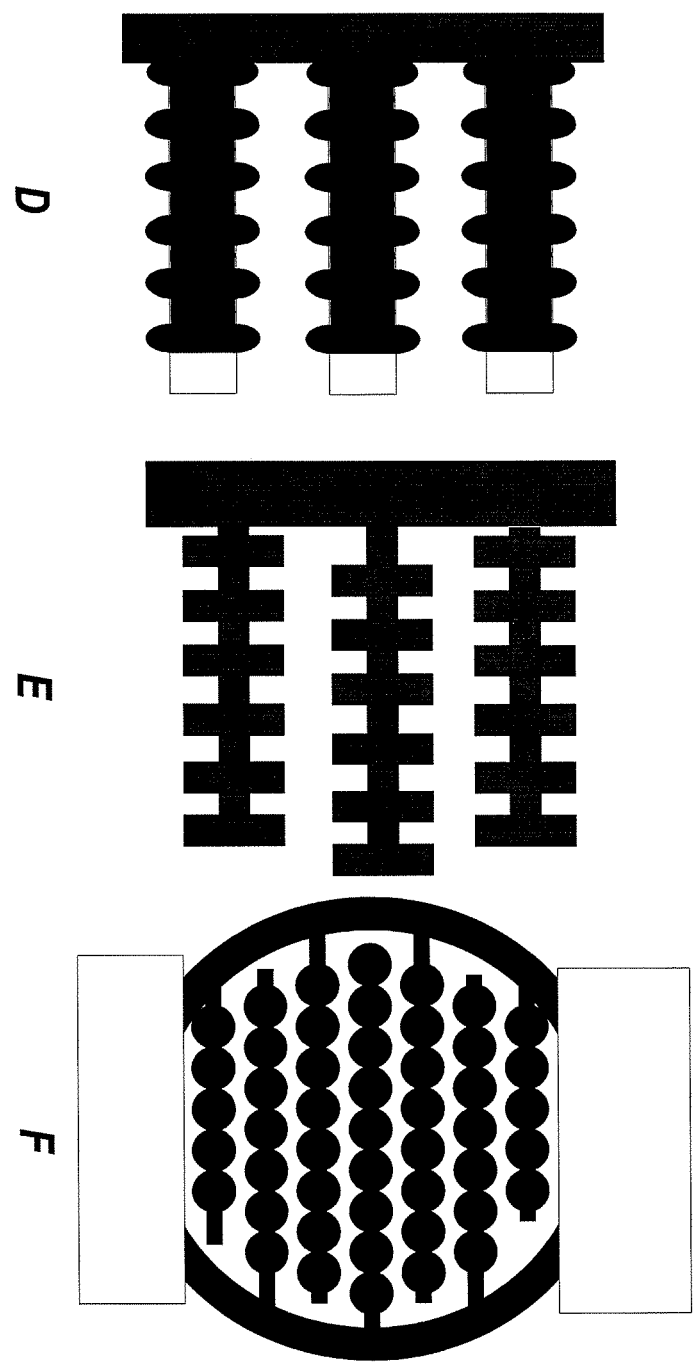
Figure 23:
FIG. 23 shows extra-cellular field potentials recorded for mouse stem-cell derived cardiomyocytes obtained using a device of the present invention, where the recording electrode is a circle-on-line electrode structure and the reference electrode is a gold wire electrode that is introduced into the well after cell seeding.

FIG. 13 shows more specific examples of such electrode structures that could be used as recording electrode for recording extracellular potentials. In FIG. 13A, a single electrode structure is shown, comprising multiple rectangular electrode elements 1301 that are connected together with an electrode bus 1303. Similarly, FIG. 13B comprises a single electrode structure, comprising multiple circle-on-line electrode elements 1311 that are connected together with an electrode bus 1313. For FIG. 13C, two electrode structures are shown, one electrode structure comprising multiple electrode elements 1331 and having electrode bus 1333, and the other electrode structure comprising electrode elements 1332 and having electrode bus 1335. The extracellular recording can be achieved using either electrode structure or both electrode structures connected together. FIGS. 22 and 23 show example of recording extracellular potentials using circle-on-line electrode structures as recording electrode and external wire electrode as reference electrode. Whilst the recorded waveform is different from those obtained with small recording electrode, the recorded signals are very reproducible between different wells.

Figure 12:
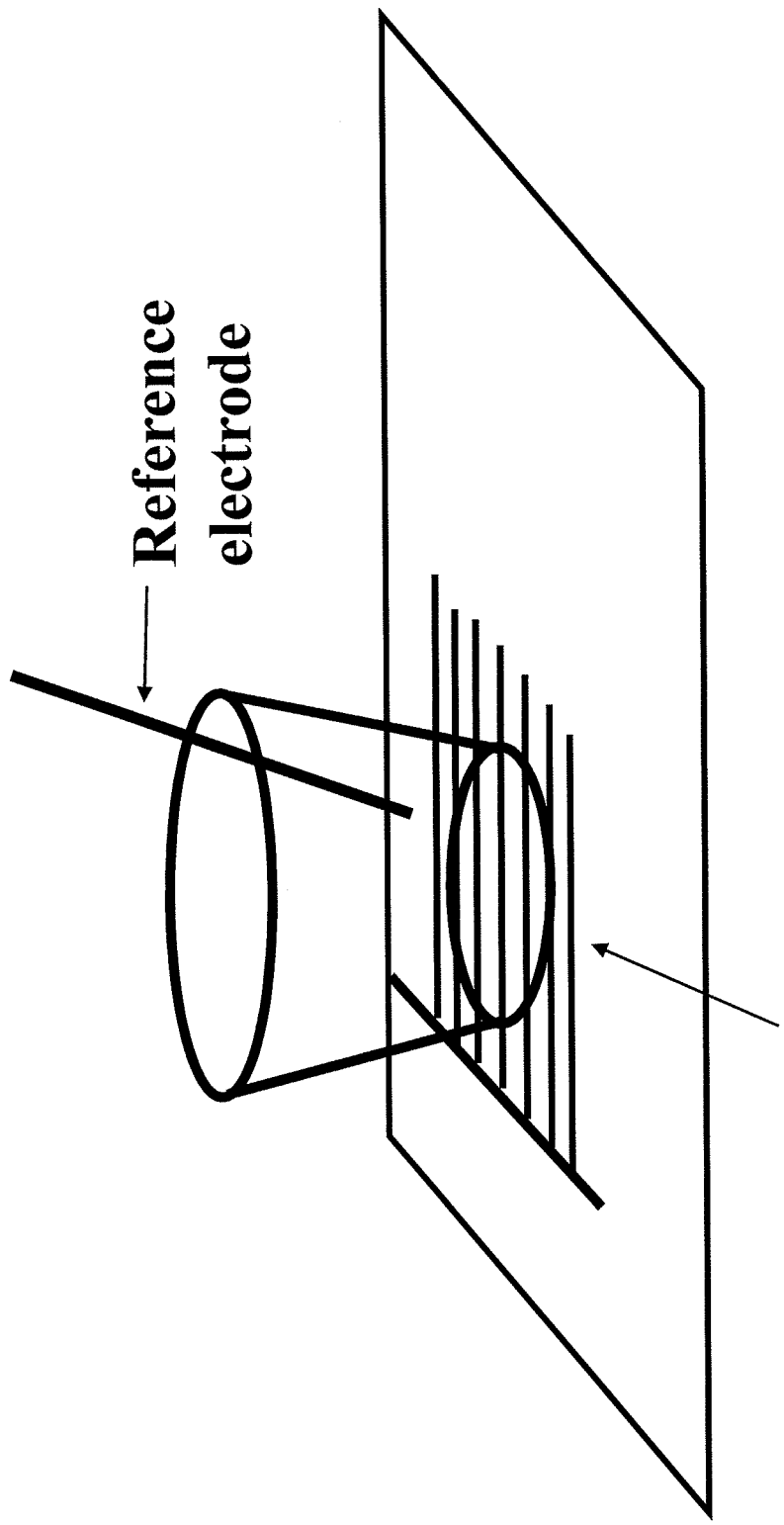
FIG. 12 shows a pair of extracellular recording electrodes, comprising a recording electrode structure on the substrate and a reference electrode external to the substrate.
Figure 14:
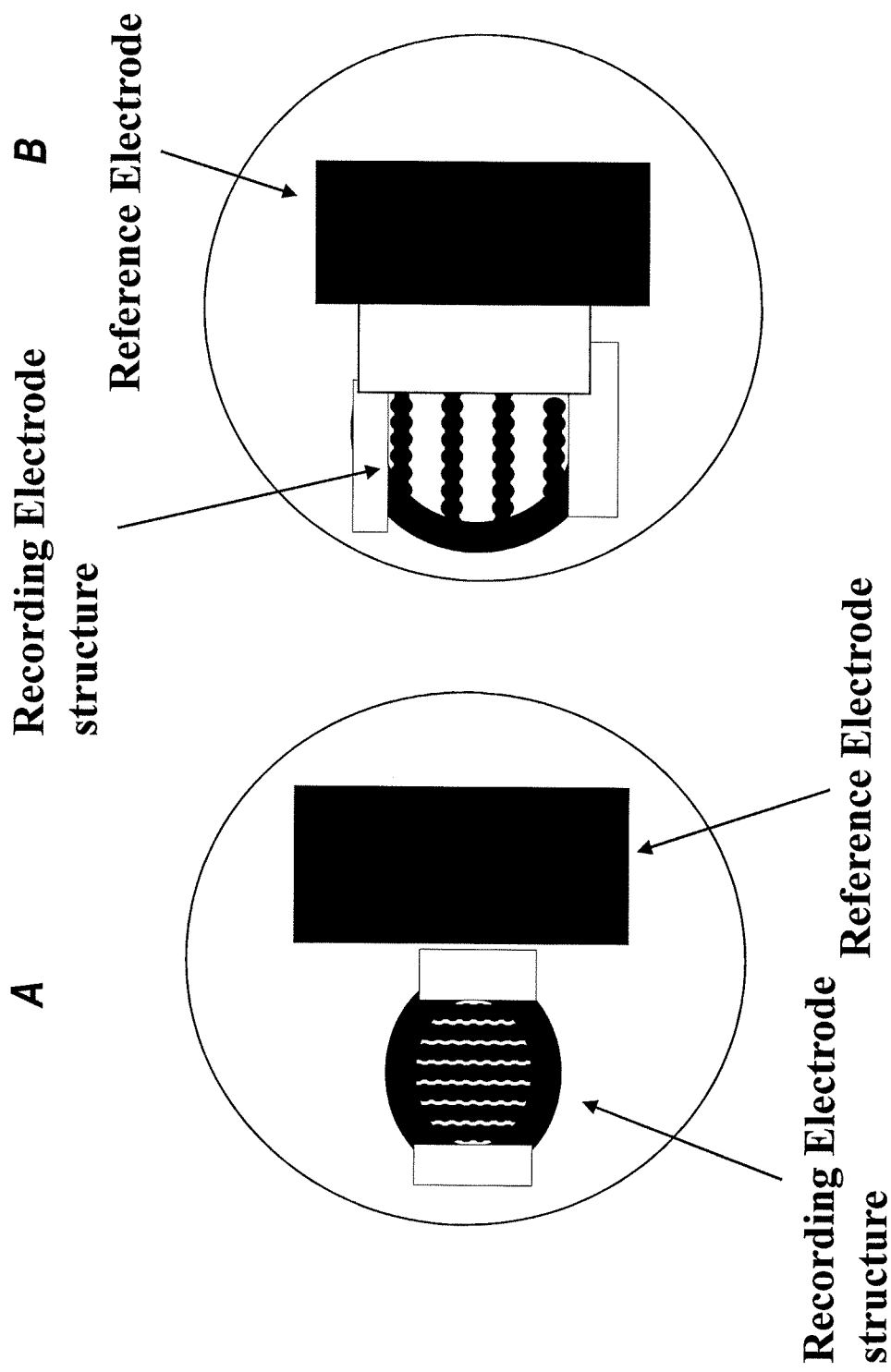
FIGS. 14A and 14B show two examples of extracellular recording devices where each well comprises one recording electrode structure comprising multiple electrode elements and a reference electrode having large surface area.

By way of yet another example, a device for performing extracellular recordings of excitable cells in vitro, may include, a) a nonconductive substrate; b) one or more wells on the substrate; c) one or more electrode structures fabricated on the substrate, each electrode structure is associated with one of the one or more wells; and d) one or more reference electrodes external to the substrate or free from contact with the substrate, each of which can be inserted into one of the one or more wells, wherein for each of the one or wells, the corresponding electrode structure and reference electrode form an electrode pair. In further embodiments, the substrate has a surface suitable for attachment of excitable cells, wherein the attachment of excitable cells on the substrate can result in detectable extracellular recording potentials between each of electrode pair. FIG. 12 shows another illustrate example of such electrode pair, comprising a recording electrode structure on the substrate and a reference electrode external to the substrate. In a particularly preferred embodiment, each electrode structure comprises multiple electrode elements. Use of such a configuration is believed to increase the sampling size and thus minimize or reduce variation between cell populations. In another preferred embodiment, each electrode structure comprises multiple electrode elements, forming half of an interdigitated electrode array (FIG. 13A). In another preferred embodiment, each electrode structure comprises multiple electrode elements so that these electrode elements form a complete interdigitated electrode array (13C) wherein during extracellular recording the electrode elements within entire interdigitated electrode array are connected together. In another preferred embodiment, each electrode structure comprises multiple electrode elements which have different electrode element shapes, including rectangular shape, or sinusoidal shape, spiral or circle-on-line shape. FIG. 13 shows examples of electrode structures having multiple electrode elements that can be used for extracellular recording where 13A, 13B, 13C, 13D, 13E and 13F are the rectangular shape, circle-on-line shape, a complete interdigitated electrode array, sinuosoidal shape, castellated shapes and a complete circle-on-line electrode array, respectively. FIG. 14 shows the examples of such electrode structures for extracellular recording where a recording electrode structure and a reference electrode are incorporated on the substrate to form a pair of electrodes. Preferably, the reference electrode is separated from the recording electrode by a barrier to the cells so that the reference electrode is in a cell-free zone when the cells are added to the electrodes. Clearly, these electrode structures are significantly different from microelectrode arrays formed by simple electrodes such as circle-shaped electrodes and/or square-shaped electrodes currently used in the field of extracellular recording.

In another preferred embodiment of the device for performing extracellular recording, each electrode structure occupies a substantial percentage of surface area of the well that the electrode structure is associated with. In some preferred embodiments, percentage of surface area of the well at the bottom being occupied by the electrode structures is more than 5%. Preferably, percentage of surface area of the well at the bottom being occupied by the electrode structures is more than 10%. More preferably, the percentage of surface area of the well at the bottom being occupied by the electrode structures is more than 20%. More preferably, the percentage of surface area of the well at the bottom being occupied by the electrode structures is more than 30%. More preferably, the percentage of surface area of the well at the bottom being occupied by the electrode structures is more than 50%. More preferably, the percentage of surface area of the well at the bottom being occupied by the electrode structures is more than 70%. More preferably, the percentage of surface area of the well at the bottom being occupied by the electrode structures is more than 85%. Clearly, such large-surface-area electrodes are significantly different from microelectrode arrays currently used in the field of extracellular recording, where recording electrodes typically have a round disc shape or a square shape of smaller size with typical dimension of 10 to 100 micron in diameter.

In another aspect of the present invention, a method performing extracellular recording of excitable cells comprises, providing a device of the present invention, adding excitable cells to the wells; providing an extra-cellular-recording amplifier that can measure and record voltage signals at microvolt levels, connecting electrodes on the devices to the extra-cellular-recording amplifier; monitoring and recording extracellular potentials at the electrodes of the devices. Preferably, the method further comprises analyzing recorded extracellular potential waveforms. More preferably, the method further comprises adding a compound to the well, measuring and recording extracellular potentials prior to and after the compound addition; analyzing extracellular potential waveforms.

I. Devices and Method for Parallel Extracellular Recording and Cell Impedance Measurement In still another aspect of the present invention, a device allowing for parallel extracellular recording and cell impedance measurement is provided. Thus, a single device or system is capable of performing both impedance monitoring of cells and extracellular recording. Thus, the device may include a means for cell impedance measuring and a means for extracellular recording operably coupled to the same substrate. In some instances, impedance monitoring occurs before extracellular recording measurements. Such an approach may permit monitoring, determining or confirming desired cell viability, morphology and the like as set forth in prior sections prior to initiating extracellular recording assays. Thus, impedance monitoring permits the user to confirm cellular phenotype or attributes prior to initiating extracellular recording. In other applications, the impedance measurement permits the monitoring of the beating of cardiomyocytes, the monitoring of the change to cell morphology, cell adhesion, cell viability or other properties after a compound treatment. Further, impedance monitoring may be conducted while performing extracellular recording or after extracellular recording. Impedance monitoring may be used to monitor cell beating, viability, morphology and the like. While impedance monitoring and extracellular recording may be performed over the same time period, the actual measurements may be obtained at different time points. That is, a switching means may permit the device to switch from an impedance monitoring mode to an extracellular recording mode. The combined approach is facilitated in part due to the increased impedance based time resolution. That is, impedance monitoring with millisecond time resolution permits such measurements to be conducted throughout a variety of time windows, without adversely affecting extracellular recording measurements.

The skilled artisan will appreciate parallel extracellular recording may be performed using a variety of configurations provided herein. In a first example, parallel recording is performed using a device that includes both a pair of electrodes for impedance monitoring and a pair of electrodes for extracellular recording, though pairs of electrodes may include a third or more electrode. Each pair is selectively operated via a switching means able to activate either an impedance monitoring mode, which allows for the connection of the impedance electrodes to external impedance measurement circuitry; or extracellular recording mode, which allows for the connection of the extracellular recording electrode and reference electrode to external voltage amplifier and signal measurement and recording circuits. In preferred embodiments, the switch is a programmed switch with adjustable parameters through a computer interface. Thus, in one example, a device for parallel impedance monitoring and extracellular recording of cells is provided, wherein the device includes: a nonconductive substrate forming or provided as a base of one or more wells; at least two impedance electrodes capable of monitoring impedance of the cells, the at least two impedance electrodes positioned within a well and on the nonconductive substrate, wherein the at least two impedance electrodes are accessible to cells when a cell sample is added to the device; an extracellular recording electrode positioned on the substrate within the well, wherein the recording electrode is accessible to cells when the cell sample is added to the device; and a reference electrode positioned within the well. In the preferred mode, the reference electrode is positioned in a cell-free zone, which is characterized as free from contact with cells when the cell sample is added to the device. When in impedance mode, the pair of impedance electrodes permits impedance monitoring of cells. When in extracellular recording mode the extracellular recording electrode and reference electrode form a pair of electrodes for extracellular recording measurements. In a related embodiment, a device is provided that includes a nonconductive substrate, having a surface suitable for attachment of excitable cells, one or more wells on the substrate; for each well, a pair of impedance measurement electrodes, wherein the attachment of excitable cells on the substrate can result in a detectable impedance change; for each well, a pair of extra-cellular recording electrodes comprising a recording electrode and a reference electrode, wherein the attachment of excitable cells on the substrate can result in a detectable extra-cellular recording potentials between the recording-electrode and reference-electrode pair. Preferably, the pair of impedance measurement electrodes is located on the substrate. Preferably the extracellular recording electrodes are located on the substrate and in the same plane as the impedance electrodes. Also, preferably in such a configuration, the reference electrode is provided in a cell-free zone. The cell-free zone prevents direct contact between cells and the reference electrode. In some instances, a physical barrier prevents contact between cells and the reference electrode. In other instances, the cell-free zone is provided on a surface that is not planar with the impedance monitoring electrodes such that the reference electrode is free from contact with cells added to the device. In still further instances, the cell-free zone is spatially positioned within the well but does not contact the substrate. In such instances, one recording electrode may be located on the substrate and another electrode may be located external to the substrate, but within a volume of the well. Positioning the reference electrode in the volume of the well free from contact with cells and the substrate permits electrically conductive medium to complete an electrical circuit between the recording electrode and reference electrode; however direct contact between cells and the reference electrode may be avoided.

Figure 16:
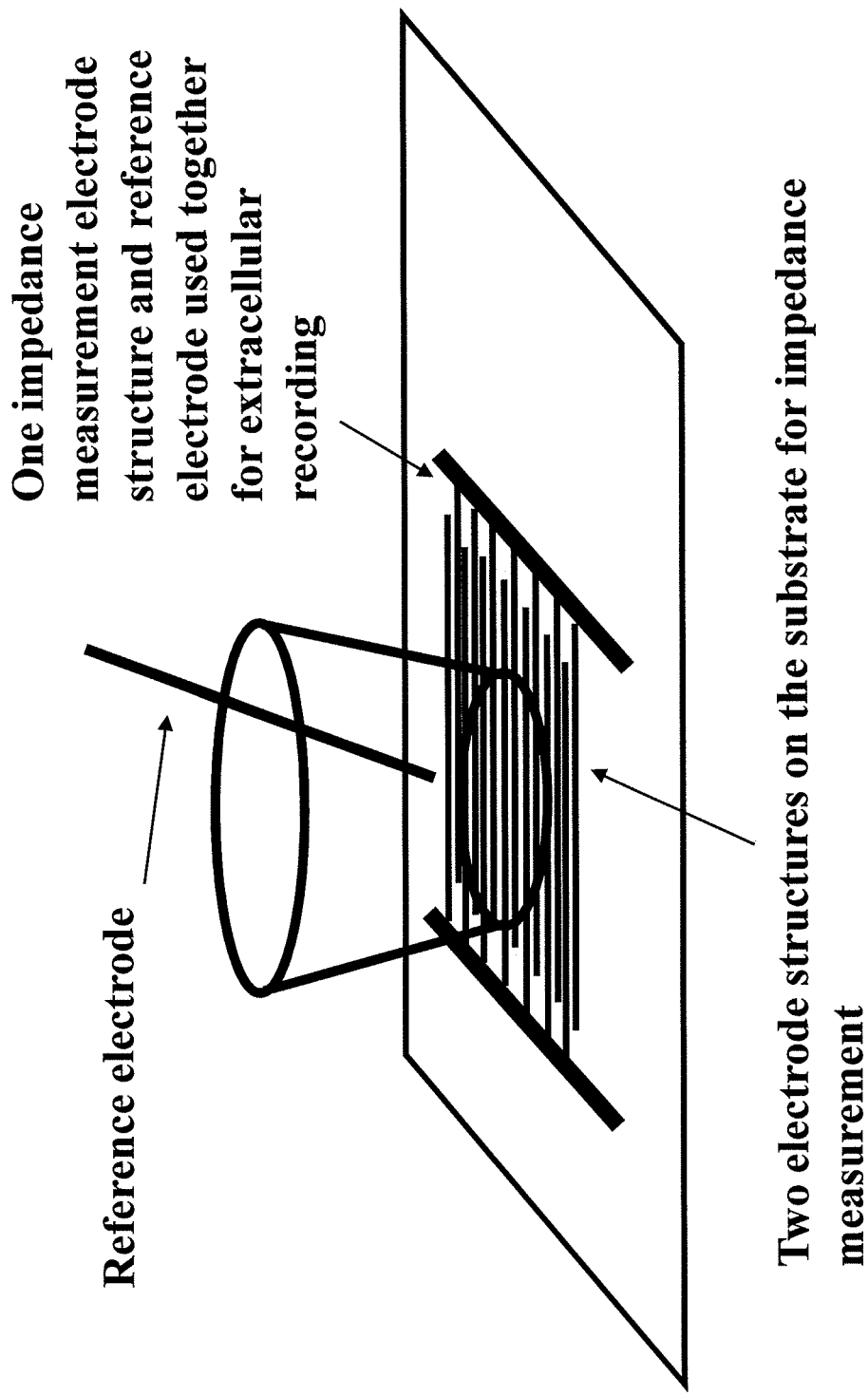
FIG. 16 shows an example of a device of the present invention where in one well, a pair of impedance measurement electrodes is located on the substrate and one of the impedance measurement electrode structures is used as an extracellular recording electrode, together with an externally applied reference electrode.

In some embodiments, the recording electrode has a diameter from about 10 um to about 200 um. In other embodiments, the recording electrode comprises an electrode structure comprising a plurality of electrode elements In other configurations, one of the impedance monitoring electrodes is provided as an extracellular recording electrode. FIG. 16 shows an example of such device where in one well, a pair of impedance measurement electrodes is located on the substrate and one of the impedance measurement electrode structures is used as an extracellular recording electrode, together with an externally applied reference electrode. In such a configuration a switching means may selectively switch between coupling signal between the two impedance electrodes in an impedance mode and between the impedance electrode and a reference electrode in an extracellular recording mode. More particularly, in one embodiment the device for parallel extracellular recording includes a nonconductive substrate forming or provided as a base of one or more wells; at least two impedance electrodes capable of monitoring impedance of the cells, the at least two impedance electrodes positioned within a well and on the nonconductive substrate; and a reference electrode, wherein a first impedance electrode from the at least two impedance electrodes is electrically coupled to the reference electrode for performing an extracellular recording measurement at the first impedance electrode. In such configurations, preferably the at least two impedance electrodes each have the same surface area and each comprise an electrode structure comprising a plurality of electrode elements. While in some embodiments the reference electrode is positioned on the substrate in other embodiments the reference electrode is an external electrode free from contact with the non-conductive substrate.

In still another aspect of the present invention a device for parallel extracellular recording includes a nonconductive substrate forming or provided as a base of one or more wells; at least two impedance electrodes capable of monitoring impedance of the cells, the at least two impedance electrodes positioned within a well and on the nonconductive substrate; and an extracellular recording electrode, wherein a first impedance electrode from the at least two impedance electrodes is electrically coupled to the extracellular recording electrode to act as a reference electrode for performing an extracellular recording measurement. That is, the impedance electrode may also operate as a reference electrode for the extracellular recording electrode. In such configurations, preferably, the at least two impedance electrodes each have the same surface area and each comprise an electrode structure comprising a plurality of electrode elements. In one specific embodiment, the recording electrode for extracellular recording is in the form of a unitary electrode structure and the reference electrode is one impedance electrode comprising multiple electrode elements. For the devices of such configuration, the cells would contact the impedance electrodes and contact the reference electrode. This is different from other embodiments of the devices used for extracellular recording described above. The advantage of this approach is that the electrode design for parallel impedance monitoring and extracellular recording is simplified. Instead of using four electrodes with two electrodes for impedance monitoring and two electrodes for extracellular recording, three electrodes are used with one impedance electrode being used for impedance monitoring and used as a reference electrode for extracellular recording. For such configuration, the extracellular recorded voltage signals would have the contributions from extracellular potential from both recording electrode and the reference electrode.

The skilled artisan will recognize the device may be operable linked to a system including an impedance analyzer, extracellular recording amplifier, electronic switches, electrical noise filtering circuits, switching means capable of switching measurement between the at least two impedance electrodes and the first impedance electrode and the reference electrode and the like. The skilled artisan will also recognize the system may include software to instruct the desired measurements or to set desired parameters for testing or operation.

In still another aspect of the present invention, the method for parallel measurement of cell-substrate impedance and extra-cellular potentials comprises a) providing a device allowing for parallel extracellular recording and cell impedance measurement; b) adding excitable cells to the wells of the device; c) providing an impedance analyzer; d) providing an extracellular potential amplifier; e) connecting electrodes of the devices to the impedance analyzer; f) connecting electrodes of the devices to the extra-cellular potential amplifier; g) performing parallel measurement of cell-substrate impedance and extracellular potentials. Preferably, the method further comprises adding compounds to the cells and monitoring cell-substrate impedance and extracellular potentials prior to and after compound addition. Preferably, the method further comprises analyzing measured time dependent impedance responses. Still preferably, the method further comprising analyzing extracellular-recording wave forms.

J. Devices and Method for Monitoring Cardiomyocyte Beating Using Label-Free Method In another aspect of the present invention, a label-free method is used to monitor cell-substrate interaction for quantifying and measuring the beating of cardiomyocytes. The label-free method refers to any method that can be monitor or measure the cells without the need of using labeling reagents or molecules. Cell impedance measurement method is one example of label-free approaches. Another label-free method includes the use of Resonant Waveguide Grating (RWG) biosensor (see reference, Y. Yang, Label-Free Cell-Based Assays with Optical Biosensors in Drug Discovery, in *ASSAY and Drug Development Technologies*, Volume 4, Number 5, 2006, 583-595; Y. Yang et al., Label-Free Cell-Based Assays for GPCR Screening, in *Combinatorial Chemistry & High Throughput Screening*, 2008, 11, 357-369; Y. Yang, Non-invasive Optical Biosensor for Probing Cell Signaling, in Sensors, 2007, Volume 7, 2316-2329).

An RWG biosensor consists of a substrate (e.g., glass), a waveguide thin film with an embedded grating structure, and a cell layer. The RWG biosensor utilizes the resonant coupling of light into a waveguide by means of a diffraction grating, leading to total internal reflection at the solution-surface interface. This type of biosensor can be used in cell-based assays to monitor changes in cell morphology, cell adhesion or other cell status parameters. The system for using such RWG biosensors can be divided into those based on angle-shift or wavelength-shift measurements. In a wavelength-shift measurement, polarized light covering a range of incident wavelengths with a constant angle is used to illuminate the waveguide; light at specific wavelengths is coupled into and propagates along the waveguide. Alternatively, in angle-shift instruments, the sensor is illuminated with monochromatic light and the angle at which light is resonantly coupled is measured. The resonance conditions are influenced by the physical properties of the cell layer that contacts with the surface of a biosensor (e.g., cell confluency, adhesion and status such as proliferating or quiescent states).

Such optical biosensor in the form of resonant waveguide, consisting of a substrate with an optical grating and a coating with a high refraction index, may be used as label-free means to monitor the beating of cardiomyocytes by monitoring the change in refractive index upon cell-substrate interaction during cardiomyocyte contraction and relaxation cycle (i.e. beating cycle). The method for such label-free monitoring of beating of cardiomyocytes includes providing a RWG biosensor for monitoring cell status operably connected to angle-shift or wavelength shift measurement system, where the device includes at least two wells optionally coated with fibronectin (or other extracellular matrix proteins) to expedite attachment; adding cells to the at least two wells, where the cells can be mouse or human or other mammalian ES cells destined to differentiate into cardiomyocytes or primary cardiomyocytes isolated directly from the heart of an experimental system including mice, rats, rabbits or dog; optically monitoring the cells of at least two wells at time intervals over a period of time via the measurement of wavelength shift or angle-shift, optionally calculating average rate of beats per unit time, average amplitude intensity in a unit time as well as the average length of time between the beats.

EXAMPLES

Extra-Cellular Recording and Cell-Substrate Impedance Measurement of Stem-Cell Derived Cardiomyocytes

Example 1

Extra-Cellular Recording on a Disc-Shaped Microelectrode Array

Medium and Reagents

The standard cell culture medium was Cor.At® Culture Medium (AXIOGENESIS AG, Cologne, Germany) supplemented with 5% of fetal bovine serum (Hyclone, Logan, USA), 100 µg/ml of puromycin. Fibronectin from bovine plasma (1 mg/mL solution, Sigma, St. Louis, USA) was used as coating (4 hrs or overnight) material before plating the mouse embryonic stem cell. E4031, a class III antiarrhythmic drug which is a specific antagonist for hERG and EAG like channels was obtained from Sigma (St. Louis, USA).

Cardiomyocyte Preparation

Cardiomyocytes (Cor.At®, AXIOGENESIS AG, Cologne, Germany) are derived from transgenic mouse embryonic stem cells. Each vial contains 1 million viable Cor.At® cardiomyocytes (>99.9% pure). These highly purified cardiomyocyte maintain the phenotype of adult mouse cardiomyocyte and express cardiac-specific connexin-43, which is an indication of the ability for excitation-contraction coupling of differentiated cardiomyocyte in vitro.

The stem cells were thawed and the suspension drop of cell density is around $10^{6-7}$/ml. The thawed stem cells were plated onto fibronectin coated multi-electrodes chip which is embed in PP dish (~130 ml volume) as the bottom. The cell plated chips were placed in 37° C. incubator (with 5% CO2, 95% humidity). The cell culture medium was changed once a day. The plated Cor.At® cell line can be grown up to 21 days post thaw with medium changes every other day.

Multichannel Recording

Figure 17:
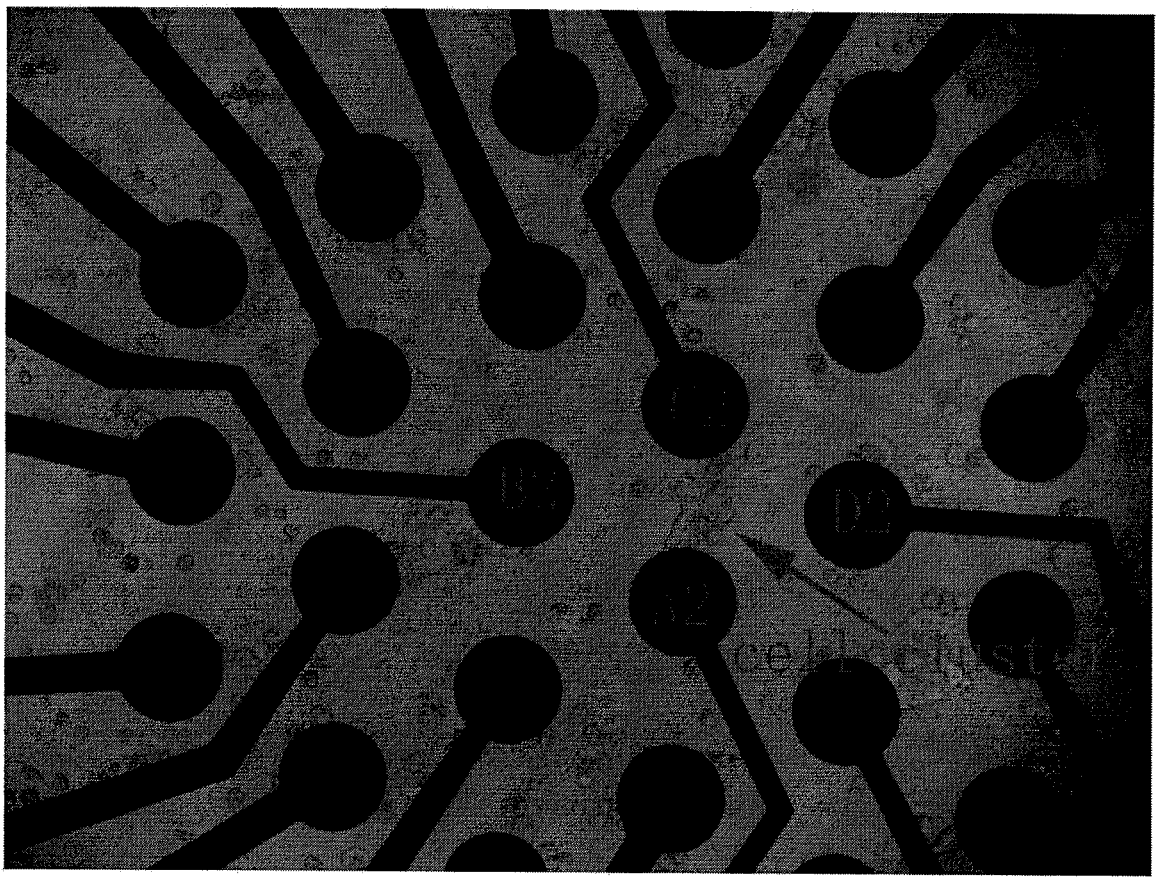
FIG. 17 shows a multi-electrode chip comprising an array of 30 electrodes where the electrode diameter is 50 µm and the interval between each two neighbor electrode tips is 50 µm.

After three to four days growing in 37° C. incubator (with 5% CO2, 95% humidity), the differentiated cells formed a monolayer onto the multi-electrode chip with some congregated cardiomyocyte showing rhythmically self-beating. The earliest onset of self beating was found on the second day after cell plating. The multichannel extracellular recording was carried out on day 3 to day 5 after cell plating using WPI ISO-DAM8A (eight channel module) amplifier (World Precision Instruments, Sarasota, USA) and Dataq DI-0720 data acquisition interface (Dataq Instrument Inc., Akron, USA). The multi-electrode chip contains an array of 30 electrodes (FIG. 17), and the diameter of the electrode tip is 50 µm and the interval between each two neighbor electrode tips is 50 µm. The signals were collected via the 4 electrodes in center which were arranged in a rectangle shape (A2, B2, C2 and D2 as shown in FIG. 17). For extracellular field potential, the field potential is measured between each of the 4-electrodes and an electrical connection that connects to all the other 26 electrodes. The extracellular field potential (FP) data were collected with following parameters being used: Low cut filter: 5 Hz; High cut filter: 1 K Hz; Sampling rate: 5 K Hz; Display sensitivity: 10 K.

Results

General Features of Field Potential

The FP signal is relatively small; the peak to peak amplitude is ≤1 mV. During the early process (day 2 to day 4 after cell plating) of growing and differentiating, the self beating frequency of cardiomyocyte cluster was increased from 60 to 90/min on day 2 (n=4) to 160 to 220/min on day 4 (n=4), and the beating frequency remain nearly-constant after day 4. In the meantime, the duration of FP was reduced and the depolarizing velocity which reflecting the upstroke of the FP was shortened while the amplitude of the FP was increased (FIG. 18). As shown in FIG. 18, the electrophysiological features were changed as the mouse derived stem cell grows and develops on day 2 and day 3. The FP amplitude and frequency were increased while the duration and depolarizing velocity were shortened.

Since the extracellular FP is the negative reflection of the intracellular voltage fluctuation, the standard shape of FP waveform consists downward depolarization peak followed by upward repolarization peak. In actual recording, we observed an initial upward peak and downward peak followed by an upward peak (FIG. 18).

Effect of E4031 on FP

Figure 19:
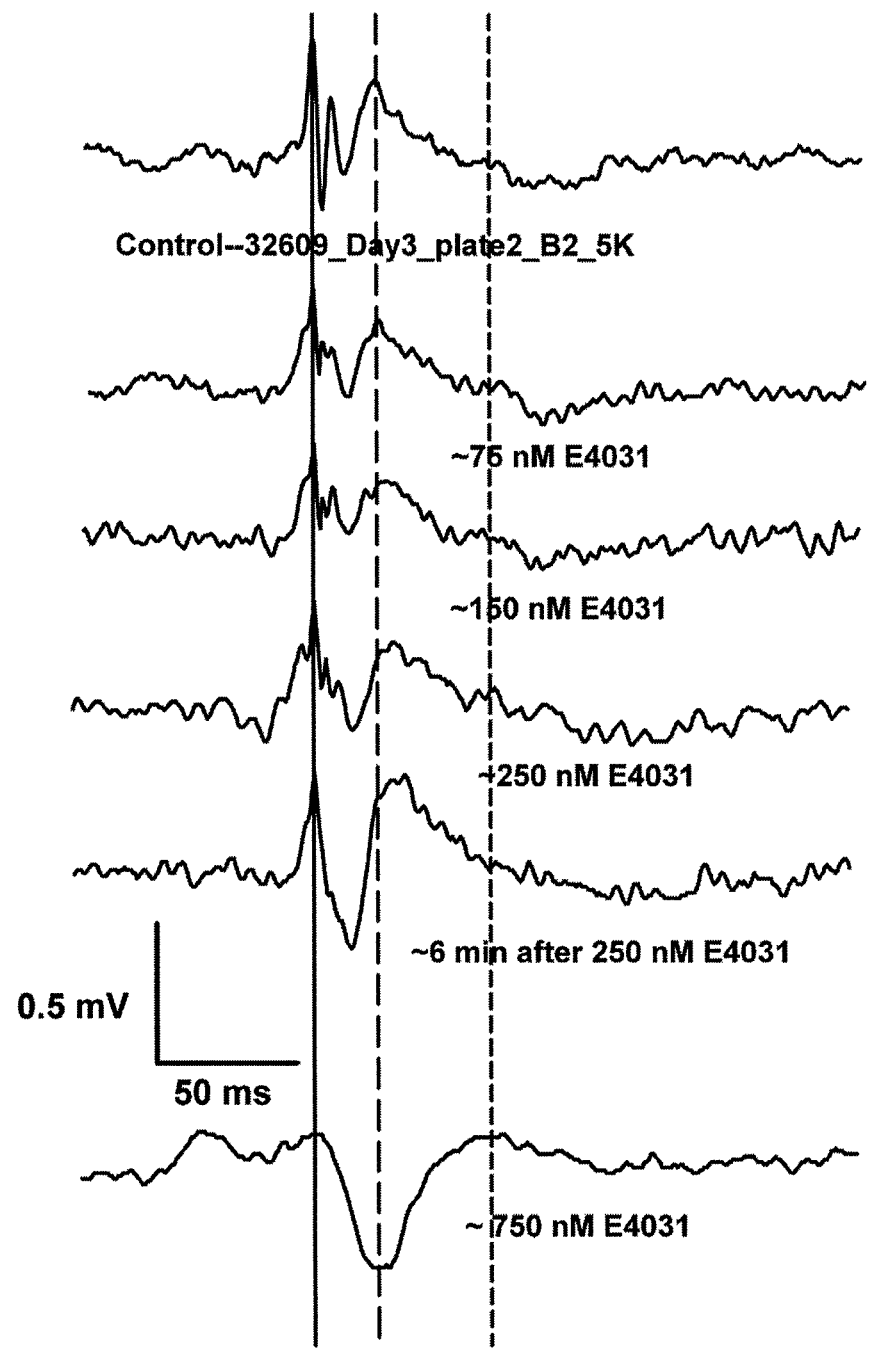
FIG. 19 shows the extracellular field potential (FP) recorded for mouse ES-derived cardiomyocytes on day 3 after cell plating using electrode array shown in FIG. 17. The cells are treated with compound E4031 at different concentrations ranging form 0 nM (control), 75 nM, 150 nM, 250 nM and 750 nM respectively.
Figure 20:
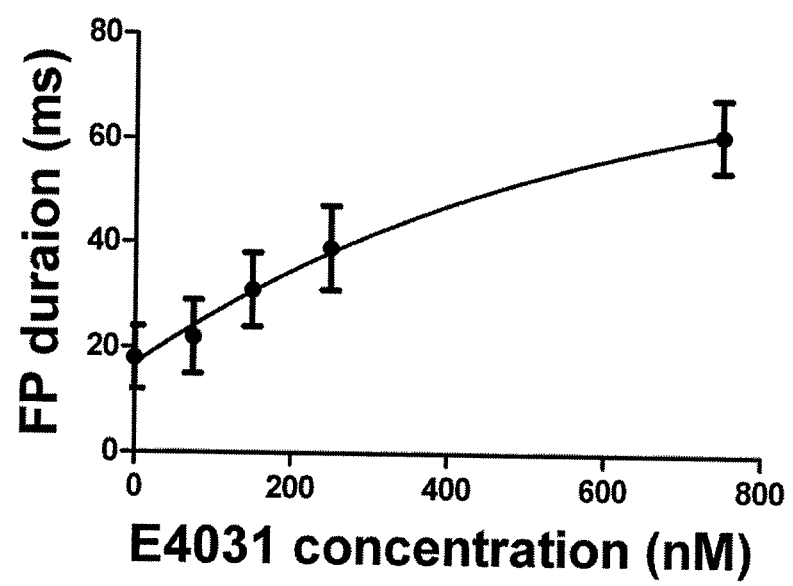
FIG. 20 shows the dependency of field potential duration in milli-seconds on the concentration of E4031.
Figure 21:
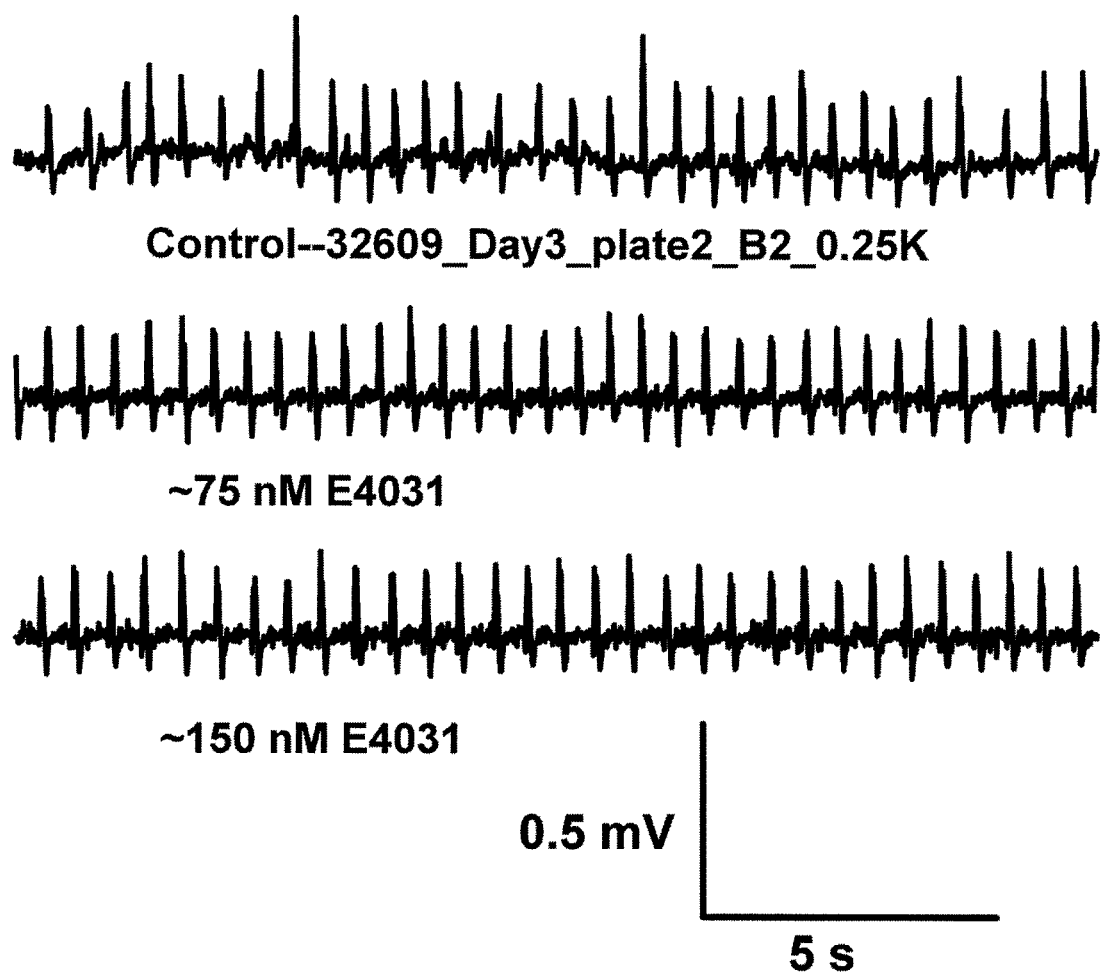
FIG. 21 shows the "anti-arrhythmic" effect of compound E4031 at 75 nM and 150 nM on field potential frequency for the mouse ES-cell derived cardiomyocytes.

E4031, antiarrhythmic agent, is a specific antagonist for hERG and EAG channel family which participate repolarization during action potential phase 3. So In present study, we picked FP duration as our main target index, and it directly correlated to the "QT interval" in clinical ECG. We found E4031 concentration-dependently delayed the depolarizing velocity and prolonged FP duration in mouse cardiomyocyte (FIG. 19) with $IC_{50}$ of 405 nM (FIG. 20). The on-site action of E 4031 on field potential is a slightly slow and it possibly due relatively the low binding affinity of E4031 to its receptor. At a concentration of 75 to 150 nM, E4031 exerted "anti-arrhythmic" action on field potential frequency in the mouse-stem-cell derived cardiomyocytes (FIG. 21).

Example 2

Extra-Cellular Recording Using One Electrode Structure on the Substrate and One External Reference Electrode FIG. 22 shows an extra-cellular field potential recording of mouse stem-cell derived cardiomyocytes obtained using a device of the present invention. The circle-on-line electrode array (with circle diameter 90 micron, line width 30 micron, the electrode gap distance 20 micron, see FIG. 13F for representation of circle-on-line electrodes) consisting of two electrode structures are fabricated on a glass substrate. During extra-cellular field potential recording, one circle-on-line electrode is used as a recording electrode and an external wire electrode is inserted into the well serving as a reference electrode. Cell preparation, reagents, cell culture and extracellular recording setup are the same as those described in to example 1.

FIG. 22A shows a field potential (after an amplification of 10,000) before treatment for a 3-day cardiomyocyte culture in a well containing circle-on-line electrodes.

Cardiomyocytes were beating at a rate of ~91 beats per minute. At the middle point of the FIG. 22A, E4031 was added to the well. No immediate effect was observed after the treatment with E4031. However, with time, the field potential gradually became irregular. The irregular field potentials at ~18 seconds and ~3 minutes after treatment were shown on FIGS. 22B and 22C. At ~5.5 minutes after treatment, the field potential magnitude was significantly reduced and later on, no field potential peaks could be detected.

Example 3

Parallel Cell-Impedance Measurement and Extra-Cellular Recording for Cardiomyocytes Prior to and after Qunindine Treatment FIG. 23A through 23E show another example of field potential change for cardiomyocytes at different time points before and after the treatment with 3 uM Quinidine, as recorded from a 3-day cardiomyocyte culture in a well containing circle-on-electrodes. Similar to the configuration for data in FIG. 22, an external wire electrode was inserted to the well serving as a reference electrode. Before treatment, cardiomyocytes were beating at a rate of ~72 beats per minute. As shown in FIG. 23 B through D, corresponding to the field potential recorded at 10 seconds, 50 seconds, 3 minutes and 9 minutes after treatment with 3 uM Quindine, Quindine has a dramatic effect on the field potential of the cardiomyocytes.

In parallel, impedance of the cardiomyocytes in such a well is monitored. FIG. 24A shows the impedance spikes as monitored on the circle-on-line electrode array before treatment. As shown in FIG. 24B through D, corresponding to the impedance spike pattern measured at ~1.5 minute, ~3 minute and ~11 minute after treatment with 3 uM Quinidine, impedance-based monitoring can readily detect the change in cardiomyocyte beating function as a result of Quindine treatment. Notably, at ~11 minutes after Quindine treatment, the amplitude of impedance spikes significantly reduced and the impedance spiking also becomes very irregular.

Example 4

Figure 25:
FIG. 25 shows extra-cellular field potentials recorded for primary cardiomyocytes obtained using a device of the present invention, where the recording electrode is a circle-on-line electrode structure and the reference electrode is a gold wire electrode that is introduced into the well after cell seeding.
Figure 26:
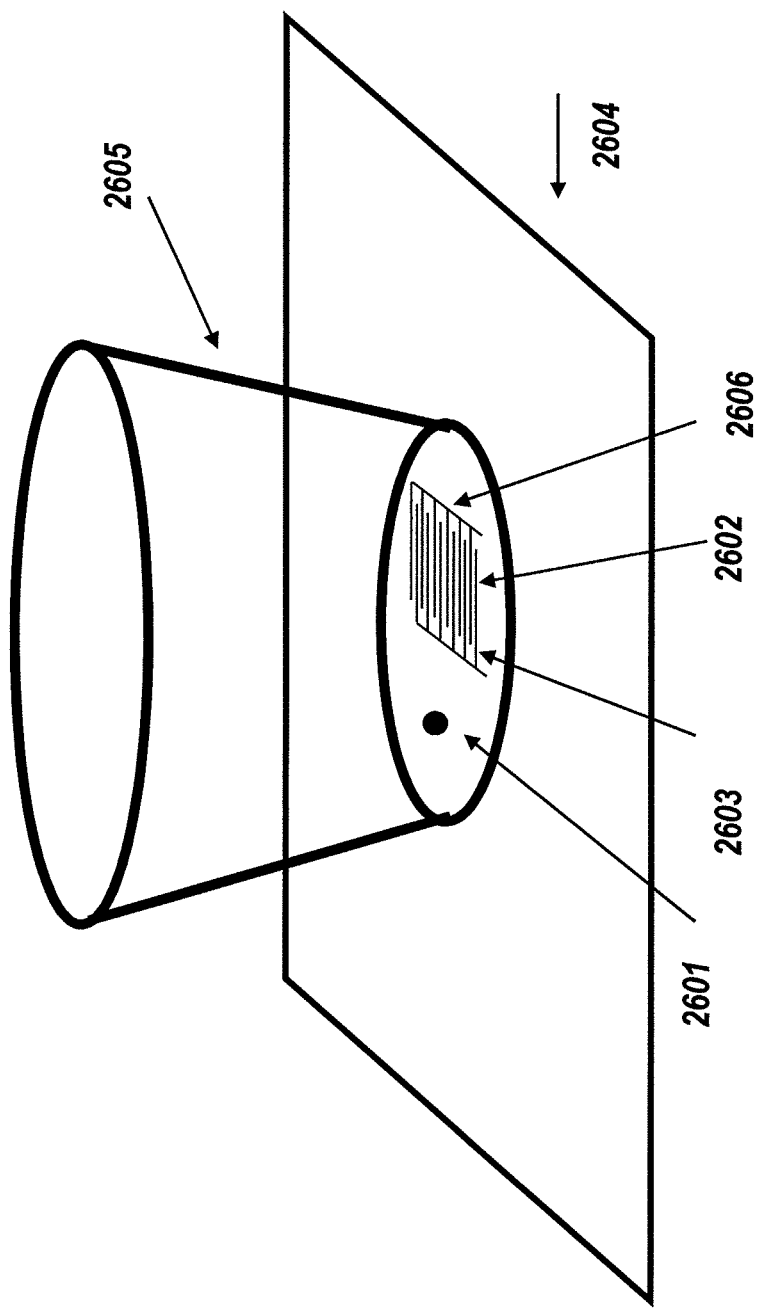
FIG. 26 shows a device of the present invention wherein the well (2605) of the device comprises a recording electrode (2601) for extra-cellular recording, an interdigitated electrode array (2602) comprising two electrode structures (2603 and 2606) each of which comprises multiple electrode elements. The electrodes are positioned on non-conductive substrate 2604. Extracellular recording of field potentials can be achieved by amplifying and recording voltage signals between the recording electrode 2601 and one electrode structure 2603 (or 2606). The impedance measurement can be conducted by monitoring impedance between electrode structures 2603 and 2606.

Extra-Cellular Recording for Primary Cardiomyocytes Between a Circle-on-Line Electrode Structure and an Externally Applied Reference Electrode Primary cardiomyocytes were prepared from by perfusing sacrificed mice' heart. The primary cardiomyocytes were added to a well containing a circle-on-line electrode array (with circle diameter 90 micron, line width 30 micron, the electrode gap distance 20 micron) on the well bottom. The electrode array is fabricated on a glass substrate. Before seeding the cells, the well was pre-coated with fibronectin. Each well was seeded with about 40,000 cells and was measured between 48 and 72 hrs after seeding. During extra-cellular field potential recording, one circle-on-line electrode structure is used as a recording electrode and an external wire electrode is inserted into the well serving as a reference electrode. The setting for extra-cellular recording is the same as those used in Example 1. FIG. 25 shows a typical field potential from such a primary cardiomyocyte culture.

Example 5

Figure 27:
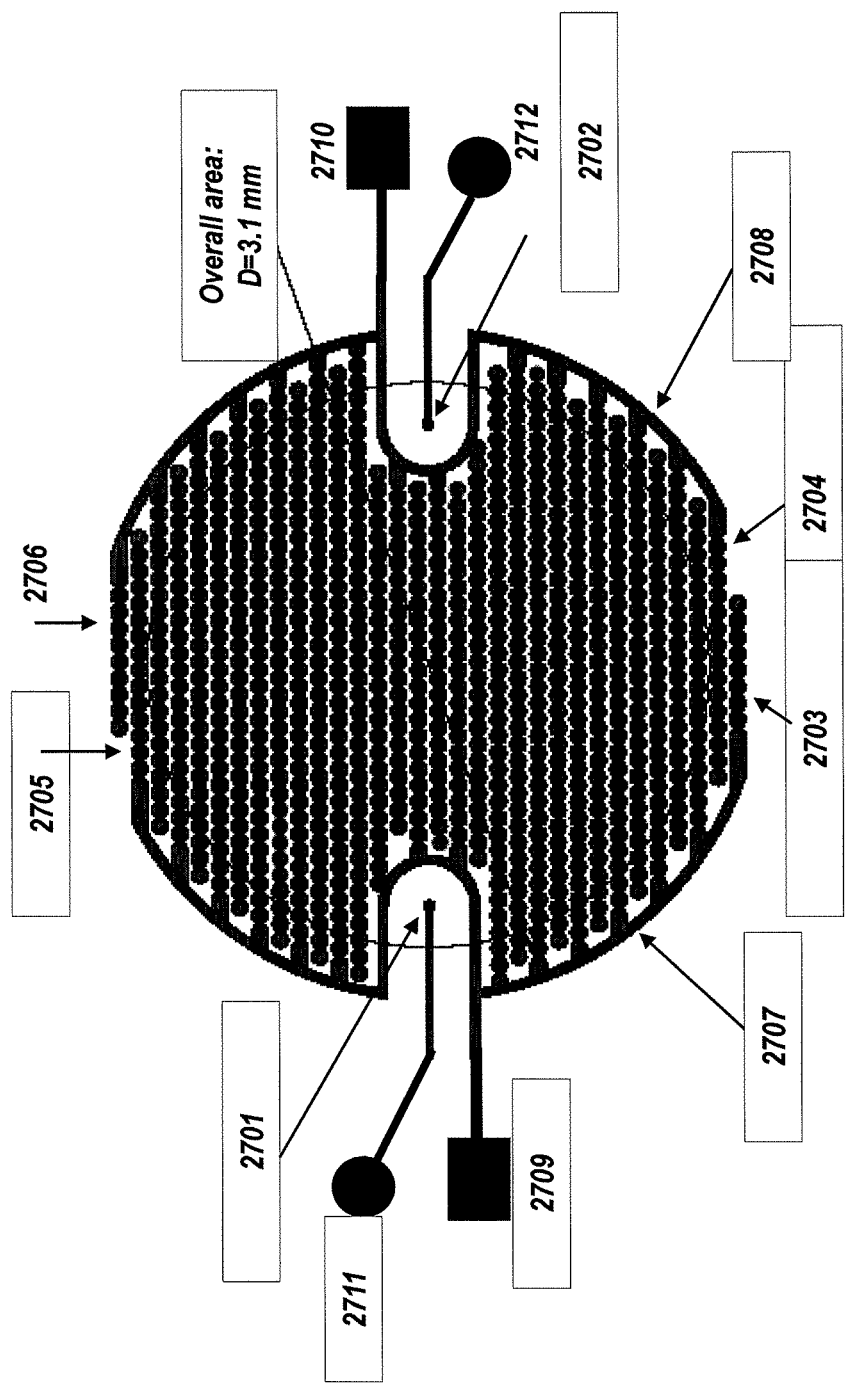
FIG. 27 shows the design of an electrode array used for combined cell-impedance measurement and extra-cellular recording.

Parallel Cell-Impedance Measurement and Extra-Cellular Recording for Cardiomyocytes FIG. 27 shows the design of an electrode array used for combined cell-impedance measurement and extra-cellular recording. For this design, the electrode array consists of two extracellular-recording electrodes 2701 and 2702 with circle geometry having diameters of 60 microns, located on either left or right side of, and in the middle section the array. Note that the recording electrode diameter could be varied from being as small as 5 micron to as large as 0.5 mm, even 1 mm, or even multiple millimeters. Electrode array further consists of two electrode structures 2703 and 2704, each comprising multiple electrode elements. Electrode elements within each electrode structure are of circle-on-line geometry and comprise interconnected circles having a diameter of 90 microns positioned along a straight line of 30 micron width (the electrode gap distance 20 micron, see FIG. 13F for representation of circle-on-line electrodes). Electrode element 2705 is the first element counting from top for electrode structure 2703. Electrode element 2706 is the first element counting from top for electrode structure 2704. Electrode elements on electrode structure 2703 are connected together through electrode bus 2707, having a width of 0.2 mm, to a connection pad 2709 which is located on the left side of FIG. 27. Similarly, electrode elements of the electrode structure 2704 are connected together through electrode bus 2708, having a width of 0.2 mm, to a connection pad 2710 which is located on the right side of FIG. 27. The overall electrode area excluding the regions consisting of electrode buses 2707 and 2708 has a diameter of 3.1 mm.

The electrode array of FIG. 27 is fabricated on glass substrate using photolithography methods for pattern-generation of thin gold electrode arrays (gold film thickness of ~100 nm on top of a Cr adhesion layer of ~10 nm). A bottomless well plate having a well-diameter of 5 mm is assembled to the electrodes-containing glass slides, with the electrode array shown on FIG. 27 being positioned at the central region of the well.

For cell impedance measurement, the impedance between two electrode structures 2703 and 2704 is measured by connecting an ACEA real-time-cell-analysis impedance analyzer capable of millisecond time resolution (e.g., 15 milliseconds or less impedance data update rate for measuring 96 wells simultaneously) to the two connection pads 2709 and 2710, connected to responding electrode buses 2707 and 2708, respectively. For extracellular recording (ECR), various recording modes can be used.

(1) ECR mode 1 is used to for monitoring electrode electrical voltage signals between an ECR electrode 2701 (or 2702) and one (impedance-measurement) electrode structure 2703 (or 2704) by connecting an ECR connection pad (2711 or 2712) and an impedance-measurement electrode connection pad (2709 or 2710) to a voltage amplifier. For this mode, extracellular signals from ECR electrodes are measured with the impedance-measurement electrode structure 2703 or 2704 used as "reference electrode". The impedance-measurement electrode structure 2703 (or 2704) has a much smaller electrode-impedance due to its much larger surface area (over 100 times larger) than ECR electrodes 2701 (or 2702).

(2) ECR mode 2 is used for monitoring electrode electrical voltage signals between an ECR electrode 2701 (or 2702) and an externally applied gold reference electrode (not shown on FIG. 27) inserted into the well by connecting an ECR connection pad (2711 or 2712) and the gold external electrode to a voltage amplifier. For this mode, extracellular signals from ECR electrodes are measured with the external gold electrode used as "reference electrode". Such external gold electrode will not have any cardiomyocytes attached and would serve as cell-free reference electrodes.

(3) ECR mode 3 is used for monitoring electrical voltage signals between impedance-measurement electrode structure 2703 (or 2704) and an externally applied gold reference electrode (not shown on FIG. 27) inserted into the well by connecting an impedance-electrode connection pad (2709 or 2710) and the external gold electrode to a voltage amplifier. For this mode, extracellular signals from impedance-measurement electrodes are measured with the external gold electrode used as "reference electrode". Such external gold electrode will not have any cardiomyocytes attached and would serve as cell-free reference electrodes.

Figure 28:
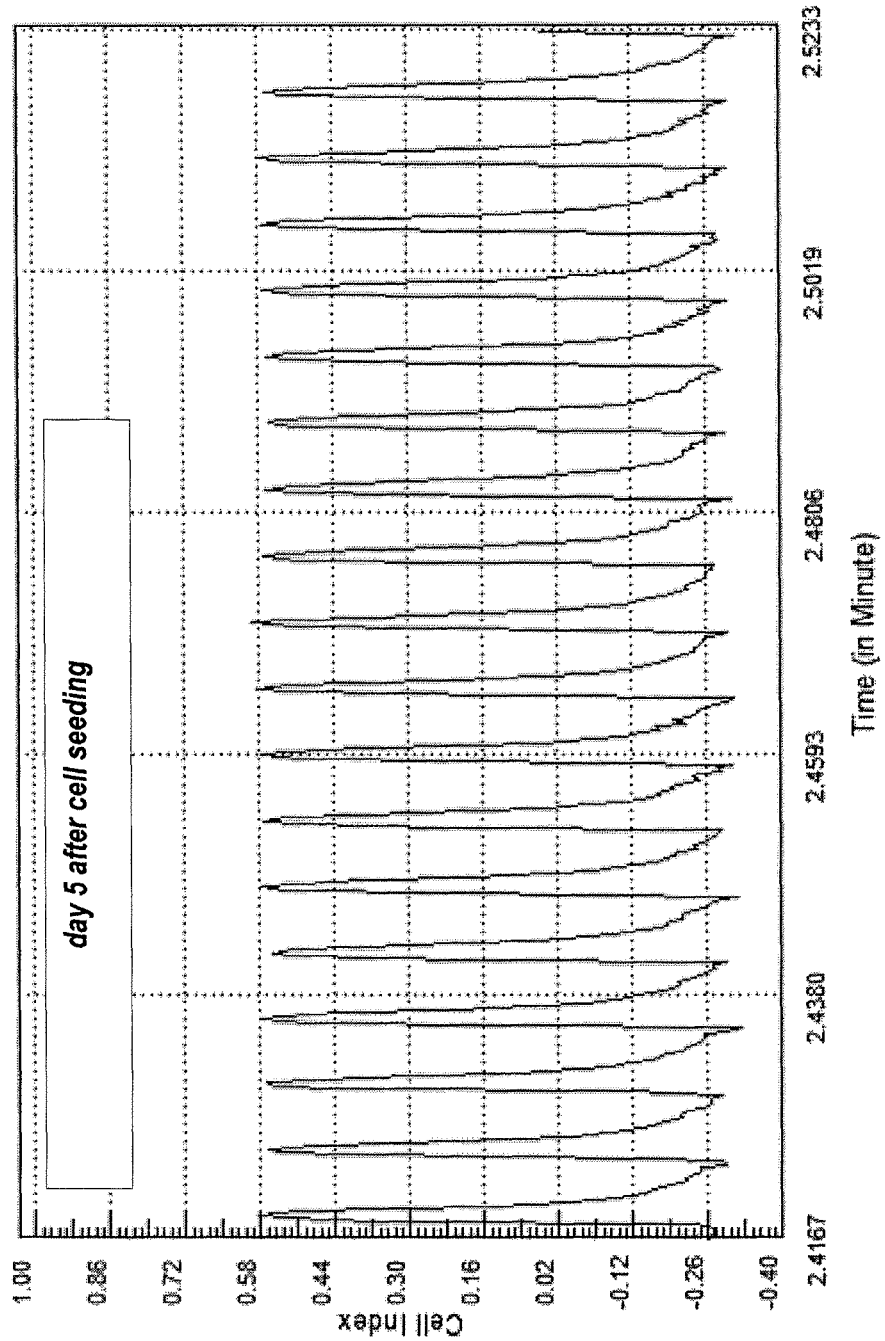
FIG. 28 shows the impedance beating result obtained for the Cor. At cells (mouse ES derived cardiomyocytes) for ~12 seconds with time-solution about 28.8 ms per data point. The impedance data is represented with cell index, a dimension less parameter.
Figure 29:
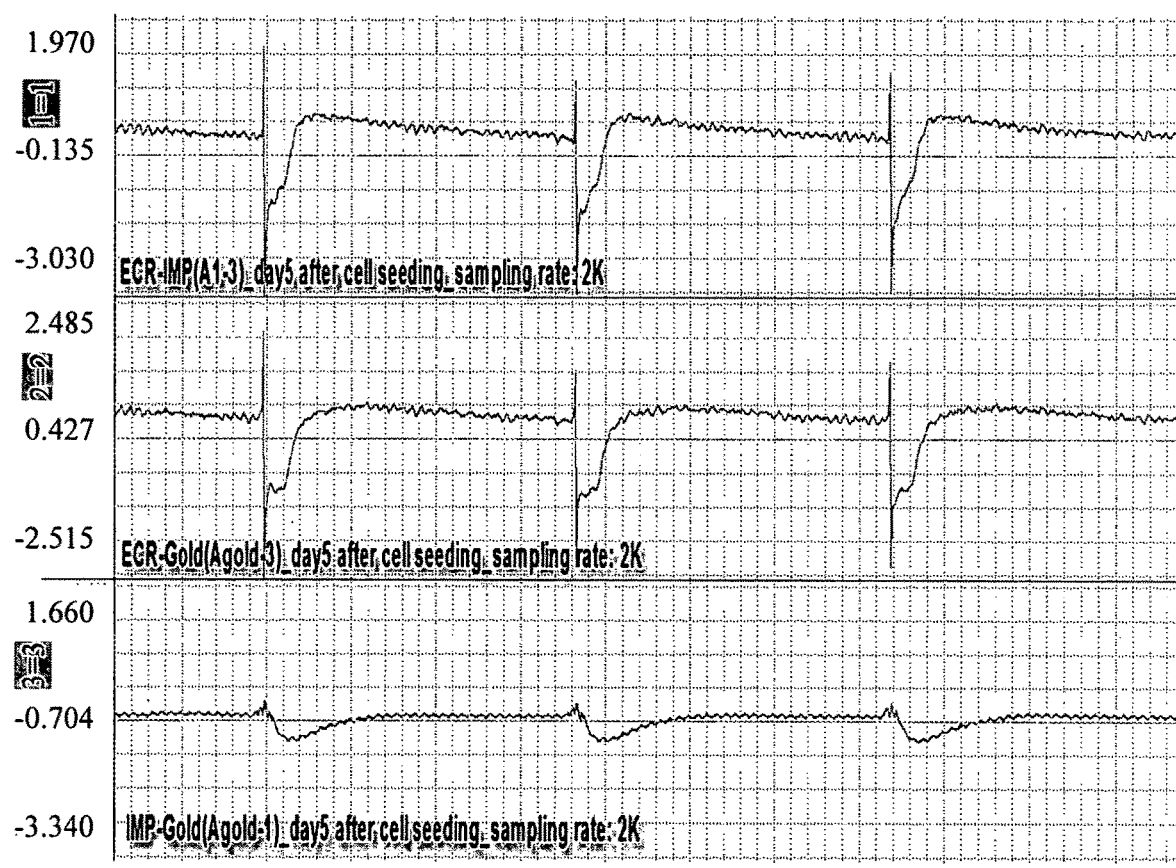
FIG. 29 shows the extracellular field potential signals obtained for the Cor. At cells (mouse ES derived cardiomyocytes) using the electrode array in FIG. 27 for three different recording modes, including: (1) ECR electrode versus impedance electrode-structure, (2) ECR electrode versus external, gold, reference electrode and (3) impedance electrode-structure versus external, gold, reference electrode.

FIGS. 28 and 29 are examples of impedance measurement and extracellular recording of Cor. At cardiomyocytes. Cor. At cells were prepared and cultured using the same method as those described in Example 1. The data on FIGS. 28 and 29 is for the Cor. At cells on day 5 after cell seeding into the electrodes-containing wells. FIG. 28 shows the impedance beating result obtained for the Cor. At cells for ~12 seconds with time-solution about 28.8 ms per data point. The impedance data is represented with cell index, a dimension less parameter. FIG. 29 shows the ECR voltage signals for the three different recording modes described above, including ECR electrode vs impedance electrode-structures, ECR electrode vs external gold electrode and impedance electrode-structure vs external gold electrode. The voltage amplifier and other ECR details are the same as those discussed in Example 1. In brief, the multichannel extracellular recording was carried out using WPI ISO-DAM8A (eight channel module) amplifier (World Precision Instruments, Sarasota, USA) and Dataq DI-0720 data acquisition interface (Dataq Instrument Inc., Akron, USA). The extracellular field potential data were collected with following parameters being used: voltage signal gain: 10,000; Low cut filter: 1 Hz; High cut filter: 1 K Hz; Sampling rate: 2-5 K Hz.

Example 6

Figure 30:
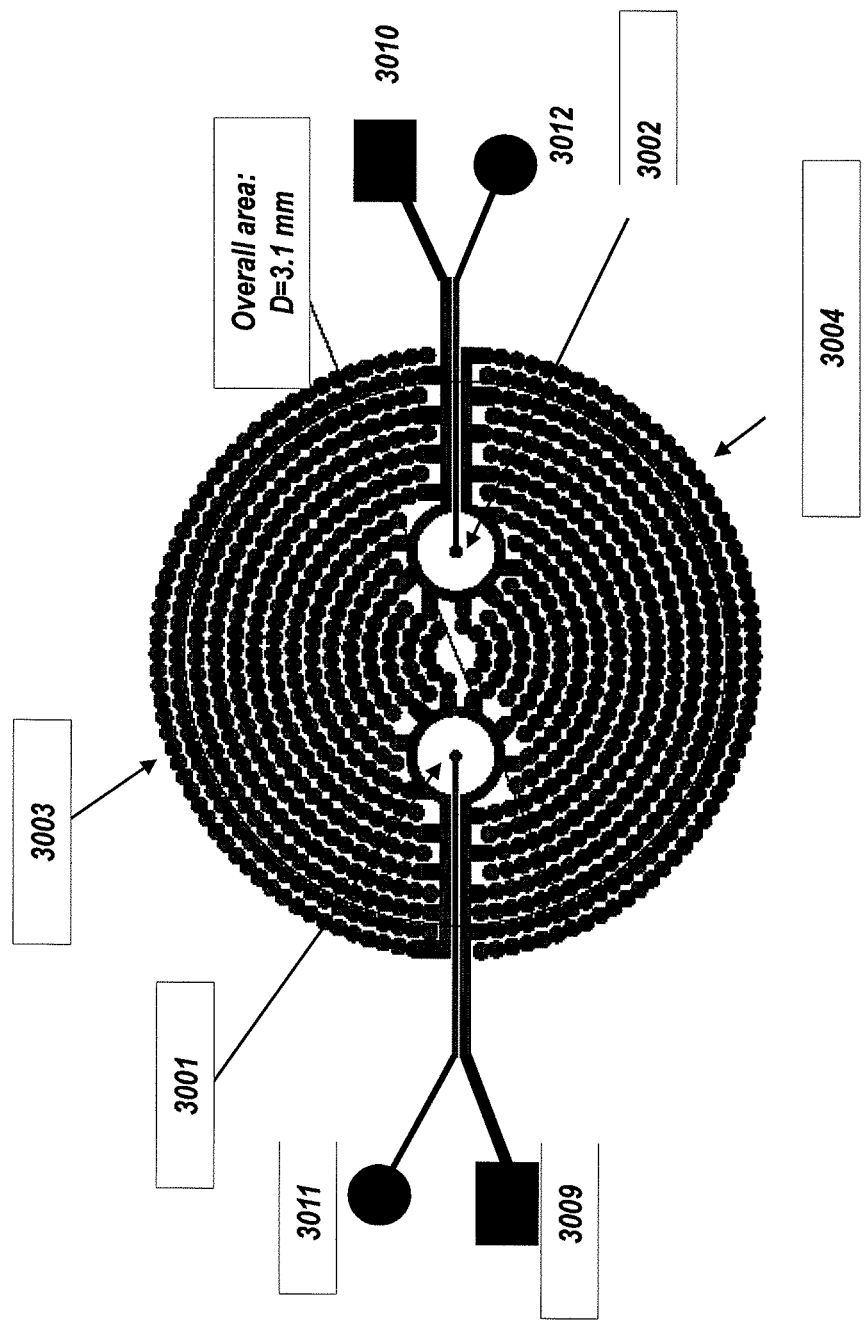
FIG. 30 shows the design of another electrode array used for combined cell-impedance measurement and extra-cellular recording.

Parallel Cell-Impedance Measurement and Extra-Cellular Recording for Cardiomyocytes FIG. 30 shows the design of another electrode array used for combined cell-impedance measurement and extra-cellular recording. For this design, the electrode array consists of two extracellular-recording electrodes 3001 and 3002 with circle geometry having diameters of 60 microns, located in the middle section the array. Note that the recording electrode diameter could be varied from being as small as 5 micron to as large as 0.5 mm, even 1 mm, or even multiple millimeters. ECR electrodes 3001 and 3002 are connected to the connection pads 3011 and 3012, respectively. The electrode array further consists of two electrode structures 3003 and 3004, each comprising multiple electrode elements. Electrode elements within each electrode structure are of circle-on-arc (curved line) geometry and comprise interconnected circles having a diameter of 90 microns positioned along curve lines of 30 micron width (the electrode gap distance 20 micron, see FIG. 13F for representation of circle-on-line electrodes). The first electrode element of the electrode structure 3003, counting from top of the electrode array, has many circles aligned-on-curved-line, forming a semi-circle arc. The first electrode element of the electrode structure 3004, counting from bottom of the electrode array, has many circles aligned-on-curved line, forming a semi-circle arc. Electrode elements on electrode structure 3005 are connected together through horizontal lines located in the middle of the electrode array to the connection pad 3009 which is located on the left side of the electrode array. Electrode elements on electrode structure 3006 are connected together through horizontal lines located in the middle of the electrode array to the connection pad 3010 which is located on the right side of the electrode array.

The electrode array of FIG. 28 is fabricated on glass substrate using photolithography methods for pattern-generation of thin gold electrode arrays (gold film thickness of 100 nm on top of a Cr adhesion layer of 10 nm). A bottomless well plate having a well-diameter of 5 mm is assembled to the electrodes-containing glass slides, with the electrode array shown on FIG. 30 being positioned at the central region of the well.

For cell impedance measurement, the impedance between two electrode structures 3003 and 3004 is measured by connecting an ACEA real-time-cell-analysis impedance analyzer capable of millisecond time resolution (e.g., 15 milliseconds or less impedance data update rate for measuring 96 wells simultaneously) to the two connection pads 3009 and 3010, connected to responding electrode structures 3003 and 3004, respectively. For extracellular recording (ECR), various recording modes can be used.

(1) ECR mode 1 is used to for monitoring electrode electrical voltage signals between an ECR electrode 3001 (or 3002) and one (impedance-measurement) electrode structure 3003 (or 3004) by connecting an ECR connection pad (3011 or 3012) and an impedance-measurement electrode connection pad (3009 or 3010) to a voltage amplifier. For this mode, extracellular signals from ECR electrodes are measured with the impedance-measurement electrode structure 3003 or 3004 used as "reference electrode". The impedance-measurement electrode structure 3003 (or 3004) has a much smaller electrode-impedance due to its much larger surface area (over 100 times larger) than ECR electrodes 3001 (or 3002).

(2) ECR mode 2 is used for monitoring electrode electrical voltage signals between an ECR electrode 3001 (or 3002) and an externally applied gold reference electrode (not shown on FIG. 30) inserted into the well by connecting an ECR connection pad (3011 or 3012) and the gold external electrode to a voltage amplifier. For this mode, extracellular signals from ECR electrodes are measured with the external gold electrode used as "reference electrode". Such external gold electrode will not have any cardiomyocytes attached and would serve as cell-free reference electrodes.

(3) ECR mode 3 is used for monitoring electrical voltage signals between impedance-measurement electrode structure 3003 (or 3004) and an externally applied gold reference electrode (not shown on FIG. 30) inserted into the well by connecting an impedance-electrode connection pad (3009 or 3010) and the external gold electrode to a voltage amplifier. For this mode, extracellular signals from impedance-measurement electrodes are measured with the external gold electrode used as "reference electrode". Such external gold electrode will not have any cardiomyocytes attached and would serve as cell-free reference electrodes.

Figure 31:
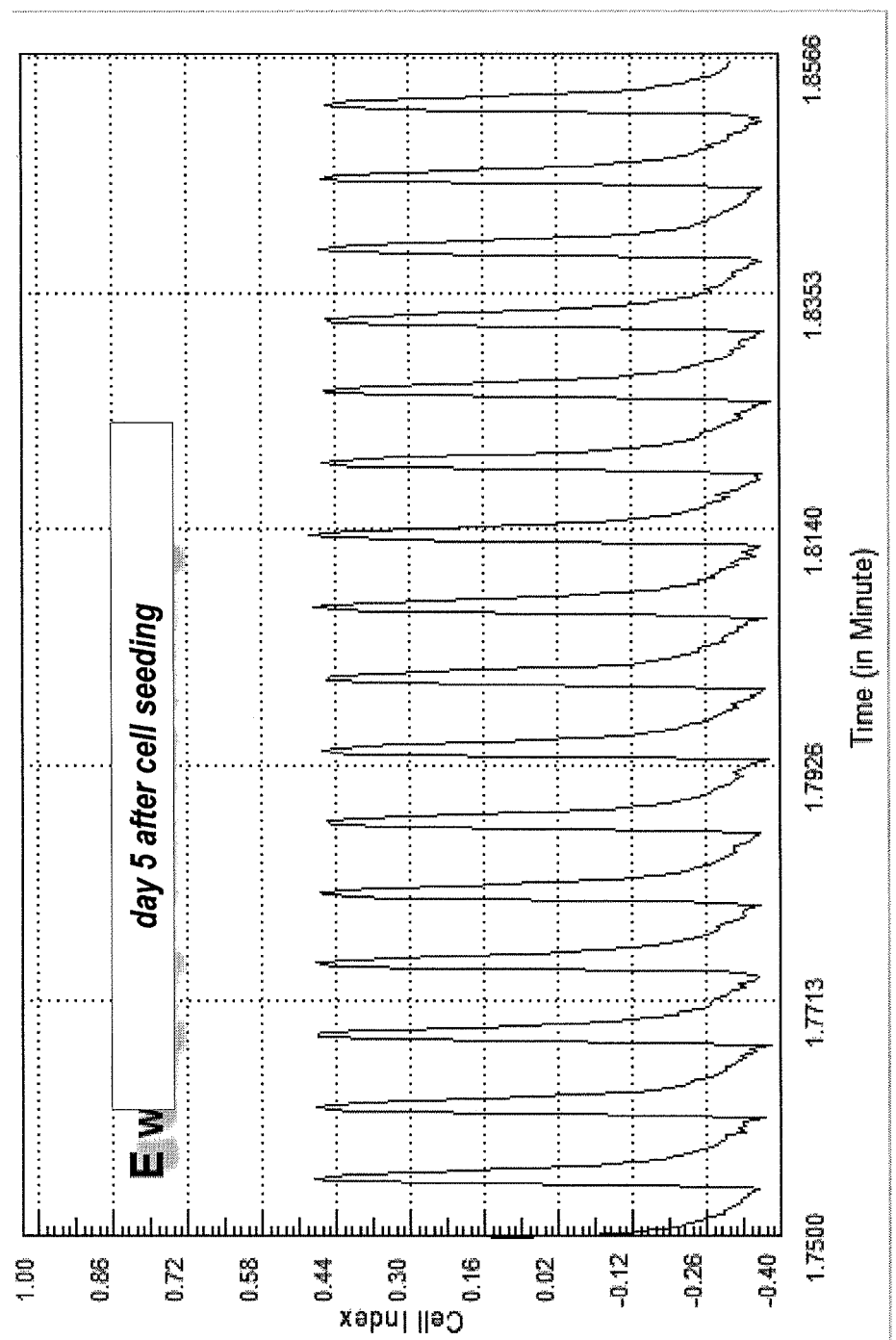
FIG. 31 shows the impedance beating result obtained for the Cor. At cells (mouse ES derived cardiomyocytes) for ~12 seconds with time-solution about 28.8 ms per data point. The impedance data is represented with cell index, a dimension less parameter.
Figure 32:
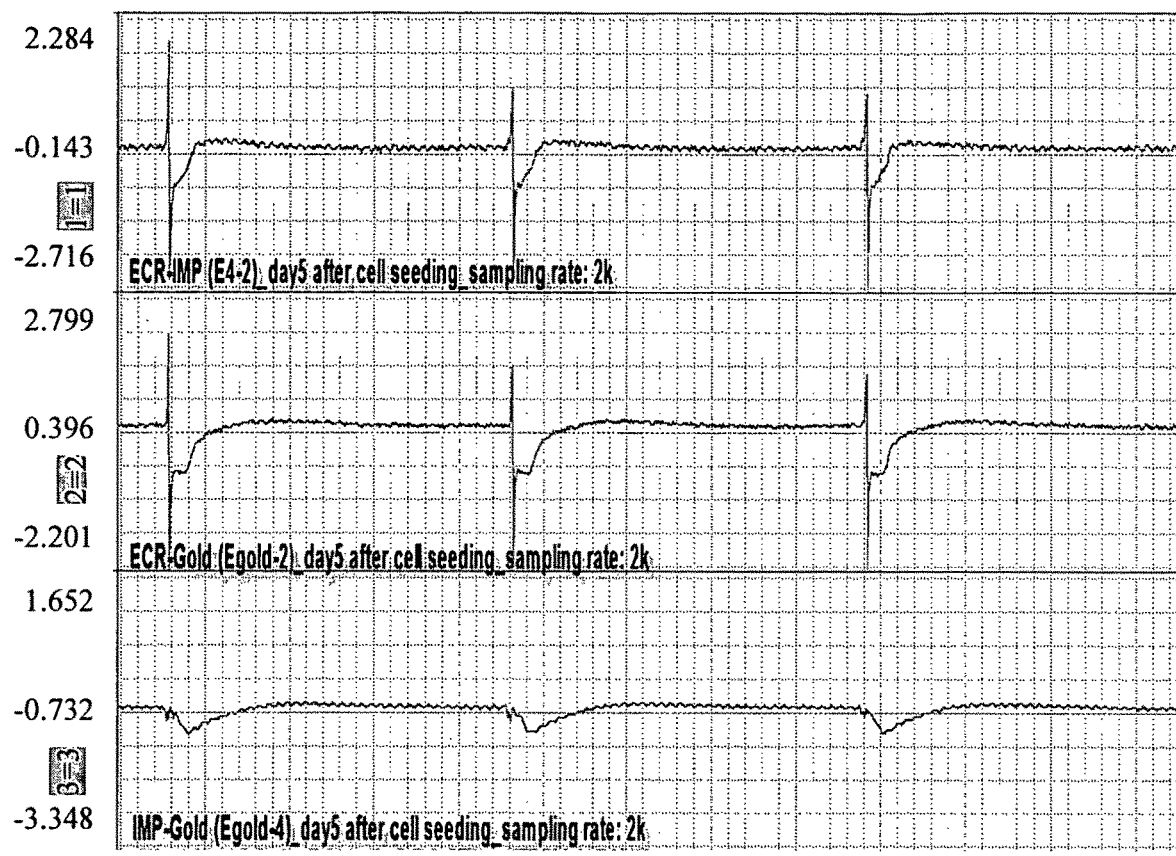
FIG. 32 shows the extracellular field potential signals obtained for the Cor. At cells (mouse ES derived cardiomyocytes) using the electrode array in FIG. 20 for three different recording modes, including: (1) ECR electrode versus impedance electrode-structure, (2) ECR electrode versus external, gold, reference electrode and (3) impedance electrode-structure versus external, gold, reference electrode.

FIGS. 31 and 32 are examples of impedance measurement and extracellular recording of Cor. At cardiomyocytes. Cor. At cells were prepared and cultured using the same method as those described in Example 1. The data on FIGS. 31 and 32 is for the Cor. At cells on day 5 after cell seeding into the electrodes-containing wells. FIG. 31 shows the impedance beating result obtained for the Cor. At cells for ~12 seconds with time-solution about 28.8 ms per data point. The impedance data is represented with cell index, a dimension less parameter. FIG. 32 shows the ECR voltage signals for the three different recording modes described above, including ECR electrode vs impedance electrode-structures, ECR electrode vs external gold electrode and impedance electrode-structure vs external gold electrode. The voltage amplifier and other ECR details are the same as those discussed in Example 1. In brief, the multichannel extracellular recording was carried out using WPI ISO-DAM8A (eight channel module) amplifier (World Precision Instruments, Sarasota, USA) and Dataq DI-0720 data acquisition interface (Dataq Instrument Inc., Akron, USA). The extracellular field potential data were collected with following parameters being used: voltage signal gain: 10,000; Low cut filter: 1 Hz; High cut filter: 1 K Hz; Sampling rate: 2-5 K Hz.

What is claimed is:

1. A system for parallel impedance monitoring and extracellular field potential recording of cells, the system comprising:
   a) a device comprising:
      i) a nonconductive substrate forming a base of one or more wells,
      ii) a set of at least two impedance electrodes capable of monitoring cell-substrate impedance of cells, the at least two impedance electrodes positioned on the nonconductive substrate within the one or more wells configured for cell-substrate impedance monitoring at 10 millisecond resolution,
      iii) a set of extracellular recording electrodes positioned on the substrate within the one or more wells and configured for extracellular field recording of the cells, wherein the set of at least two impedance electrodes and the set of extracellular recording electrodes are different sets of electrodes, further wherein all of the electrodes are on a same surface;
   b) an impedance analyzer for measuring cell-substrate impedance at 10 millisecond resolution;
   c) an extracellular field potential amplifier for extracellular field potential recording; and
   d) a switch that switches the one or more wells between measuring impedance and extracellular field potential recording modes.

2. The system according to claim 1, wherein the at least two impedance electrodes are interdigitated electrodes.

3. The system according to claim 2, wherein each of the at least two impedance electrodes comprises an electrode structure comprising a plurality of electrode elements, wherein the electrode elements of different electrode structure are interdigitated.

4. The system according to claim 2, wherein the at least two impedance electrodes and set of extracellular recording electrodes share a same electrode.

5. The system according to claim 1, wherein the at least two impedance electrodes and set of extracellular recording electrodes share a same electrode.

6. The system according to claim 1, wherein impedance may be monitored for cells positioned at either of the at least two impedance electrodes, further wherein one of the at least two impedance electrodes is configured as a reference electrode in the set of extracellular recording electrodes.

7. A method of extracellular field potential recording and impedance monitoring of a cell population, the method comprising:
   a) providing the system according to claim 1;
   b) adding a cell sample to the device;
   c) performing extracellular field potential recording measurements of the cell sample by amplifying the voltage signals between the set of extracellular recording electrodes and monitoring the amplified signals; and
   d) performing impedance measurements by monitoring cell-substrate impedance between the two impedance electrodes at 10 millisecond resolution.

8. The method according to claim 7, wherein the cells comprise cardiomyocytes or cardiomyocyte precursor cells, the method further comprising adding a compound suspected of affecting a beating cycle of the cells.

9. The method according to claim 8, further comprising resolving polarization and depolarization of beating cells.

10. The method according to claim 8, further comprising determining whether or not the compound affects cell beating.

11. The method according to claim 9, further comprising resolving a beating cycle of the cells from the impedance measurements.

12. The method according to claim 9, further comprising determining a beating rate from the impedance measurements.

13. The method according to claim 9, further comprising determining a beating amplitude from the impedance measurements.

14. The method according to claim 9, wherein the step of performing impedance measurements is performed at 5 millisecond resolution.

15. The method according to claim 9, wherein two consecutive impedance measurements are performed at 1 millisecond or faster.

16. The method according to claim 7, further comprising calculating a cell index parameter from measured impedance values.

17. The method according to claim 7, wherein the cells comprise cardiomyocytes or cardiomyocyte precursor cells, the method further comprising resolving a beating cycle of the cells from the impedance measurements.

18. The method according to claim 7, wherein the cells comprise cardiomyocytes or cardiomyocyte precursor cells, the method further comprising determining a beating rate from the impedance measurements.

19. The method according to claim 7, wherein the cells comprise cardiomyocytes or cardiomyocyte precursor cells, the method further comprising determining a beating amplitude from the impedance measurements.

20. The method according to claim 7, wherein the step of performing impedance measurements is performed at 5 millisecond resolution.

21. The method according to claim 7, wherein two consecutive impedance measurements are performed at 1 millisecond or faster.

* * * * *